United States Patent [19]
Busch et al.

[11] Patent Number: 5,473,162
[45] Date of Patent: * Dec. 5, 1995

[54] INFRARED EMISSION DETECTION OF A GAS

[75] Inventors: Kenneth W. Busch, Waco, Tex.; M. Keith Hudson, Little Rock, Ark.; Marianna A. Busch, Waco; Sidney W. Kubala, Jr., Angleton, both of Tex.; David C. Tilotta, Grand Forks, N. Dak.; Christopher K. Y. Lam, Central, S.C.; Ravishankar Srinivasan, Houston, Tex.; Yunke Zhand, Columbia, S.C.

[73] Assignee: Baylor University, Waco, Tex.

[*] Notice: The portion of the term of this patent subsequent to Sep. 21, 2010, has been disclaimed.

[21] Appl. No.: 123,733

[22] Filed: Sep. 20, 1993

Related U.S. Application Data

[63] Continuation-in-part of Ser. No. 415,141, Sep. 29, 1989, Pat. No. 5,246,868, which is a continuation-in-part of Ser. No. 263,089, Oct. 26, 1988, abandoned, which is a continuation-in-part of Ser. No. 120,050, Oct. 26, 1987, abandoned.

[51] Int. Cl.$^6$ ............................ G01N 21/71; G01N 21/62
[52] U.S. Cl. ................................ 250/341.6; 250/339.08; 250/339.13; 356/311
[58] Field of Search ........................ 356/311, 312, 356/313, 314; 250/339.13, 339.14, 341.6, 339.08

[56] References Cited

U.S. PATENT DOCUMENTS

| | | | |
|---|---|---|---|
| 2,302,554 | 11/1942 | Kingsbury | 88/22.5 |
| 2,349,715 | 5/1944 | Francis . | |
| 2,458,973 | 1/1949 | Barnes . | |
| 2,562,525 | 7/1951 | Cary . | |
| 3,080,483 | 3/1963 | Jaffe et al. . | |
| 3,210,546 | 10/1965 | Perron . | |
| 3,516,745 | 6/1970 | Schuman | 356/85 |
| 3,539,807 | 11/1970 | Bickel . | |
| 3,561,846 | 2/1971 | Kingsland | 250/219 |
| 3,594,658 | 7/1971 | Cason | 331/94.5 |
| 3,679,899 | 7/1972 | Dimeff . | |
| 3,689,225 | 9/1972 | White | 23/253 |
| 3,696,247 | 10/1972 | McIntosh et al. . | |
| 3,723,831 | 3/1973 | Rogers | 317/234 |
| 3,749,495 | 7/1973 | Wilkins et al. | 356/51 |
| 3,836,255 | 9/1974 | Schuman | 356/85 |

(List continued on next page.)

FOREIGN PATENT DOCUMENTS

| | | |
|---|---|---|
| 90915999 | 10/1992 | European Pat. Off. . |
| 89900090 | 5/1993 | European Pat. Off. . |
| 2101655 | 7/1972 | Germany . |
| 1332203 | 8/1987 | U.S.S.R. . |
| WO89/03980 | 5/1989 | WIPO . |
| WO91/95241 | 4/1991 | WIPO . |

OTHER PUBLICATIONS

Johansson et al, "A Multiple Grating Flame Photometer for the Simultaneous Determination of Five Elements", Spectrochimica Acta, 31B(7), 1976, pp. 419–428.

Plyer et al., Optical Systems for Increasing the Available Intensity from Flames, *J. Opt. Soc. Amer.*, 42:360, 1952.

Bernard, B. B., *A Summary of TOC Developments*, O.I. Corporation, Jun. 1985.

(List continued on next page.)

*Primary Examiner*—Carolyn E. Fields
*Attorney, Agent, or Firm*—Arnold, White & Durkee

[57] ABSTRACT

Apparatus and method for qualitatively and quantitatively analyzing infrared emission from excited molecules in the determination of, for example, total inorganic carbon, chloride and available chlorine in aqueous samples. Methods of exciting the gas-phase, infrared-active molecules to emit radiation include flame excitation, furnace excitation, excitation by electron impact in a gas discharge or excitation by collisions with a vibrationally excited diatomic molecule. The detector is optimized by use of dual beam system with background subtraction capabilities thereby eliminating background noise and fluctuations therein.

34 Claims, 47 Drawing Sheets

OTHER PUBLICATIONS

Busch and Busch, "Signal–to–Noise Comparison of Flame Furnace Infrared–Emission (FIRE) Spectrometry with Room–Temperature, Nondispersive Infrared–Absorption Spectrophotometry," *Applied Spectroscopy*, 47(7):912–921, Jul. 1993.

Freeman and Hieftje, "Near–infrared Nonmetal Atomic Emission from a Helium Microwave–Induced Plasma. Element Ratio Determinations," *Spectrochim Acta*, 40B(4):653–664, 1985 (abstract only).

McGraw–Hill, Encyclopedia of Science and Technology, pp. 116–117 (1977).

Griffiths, "Infrared Emission Spectroscopy. I. Basic Considerations," *Applied Spectroscopy*, vol. 26, No. 1, 1972, 73–76.

Hudson et al. "Infrared Emission from a Flame as the Basis for Chromatographic Detection of Organic Compounds," *Anal. Chem.*, 1987, 59, 2603–2609.

Davidchuck et al., "Unit for Investigating the Radiation Spectrum of the Combustion Products of Condensed Systems in the Range of 0.5–8uM," *Combustion Explosion & Shock Waves*, 10(5):683–685, 1974.

Hylton et al., "System for the Measurement of Spectral Emittance at High Temperature," *AIAA Journal*, 14(9):1303–1310, 1976.

Herget et al., "Remote Fourier Transform Infrared Air Pollution Studies," *Optical Engineering*, 19(4):508–514, 1980.

Gaydon, A. G., *The Spectroscopy of Flames*, Chapman and Hall, London, pp. 221–243, 1974.

Gaydon et al., *Flames, Their Struction, Radiation and Temperature*, 4th Ed., Chapman and Hall, London, pp. 238–259, 1979.

Plyler et al., "Infrared Radiation from a Bunsen Flame" *J. Res. Nat. Bur. Stand.*, 40:113, 1948.

Nakamoto, K., *Infrared Spectra of Inorganic and Coordination Compounds*, John Wiley, New York, p. 77, 1963.

Curcio et al., "Transmission of Infrared Radiation from Flames by $CO_2$", *Appl. Opt.*, 5:231–233, 1966.

Putley, *Optical and Infrared Detectors*, Keyes (ed.) Springer–Verlag, Berlin, Chapter 3, 1980.

Boyd, *Radiometry and the Detection of Optical Radiation*, John Wiley, New York, Chapter 10, 1983.

Busch et al., "Simultaneous Determination of Electrolytes in Serum Using a Vidicon Flame Spectrometer", Busch et al., *Anal. Chem.*, 46:1231, 1974.

Garrett, R. L., *J. Pet. Tech.*, p. 860, Jun. 1978.

Small et al., *International Laboratory*, "Oxidation and Detection Techniques in TOC Analysis", May, 1986.

Small, "All About TOC Analyzers" *Pollution Engineering*, p. 53, Sep. 1980.

Capelle et al., *Review of Scientific Instruments*, 49(8):1124–1129, Aug., 1978.

Karger et al., *An Introduction of Separation Science*, Wiley, New York, pp. 232–236, 1973.

Greenberg et al., Eds, *Standard Methods for the Examination of Water and Wastewater*, American Public Health Association, Washington, D.C., pp. 286–294, 1985.

Manahan, S. E., *Environmental Chemistry*, 3rd Ed., Willard Grant Press, Boston, Massachusetts, p. 29, 1979.

Busch et al., "Flame/Furnace Infrared Emission Spectroscopy: New Ways of Playing with FIRE," *Spectroscopy*, 4(8):22–36, 1989.

Busch et al., "A High–Efficiency Light–Collection System for Energy–Limited Infrared Emission Radiometers," *Applied Spectroscopy*, 45(6):964–968, 1991.

Busch and Busch, "Analytical Applications of Flame/Furnace Infrared Emission Spectrometry," *Spectrochimica Acta Rev.*, 14(4):303–336, 1991.

Busch and Busch, "Signal–to–Noise Considerations in Flame/Furnace Infrared Emission Spectroscopy," *Applied Spectroscopy*, 45(4):546–554, 1991.

Busch and Busch, "Flame Infrared–Emission—An Element–/specific Detector for GC," *American Laboratory*, 23(11):18, 1991. Abstract only.

Crane, "Selection of a TOC Analyzer," *American Laboratory*, pp. 51–58, 1988.

Hudson and Busch, "Flame Infrared Emission Detector for Gas Chromatography," *Anal. Chem.*, 60:2110–2115, 1988.

Hudson and Busch, "Infrared Emission from a Flame as the Basis for Chromatographic Detection of Organic Compounds," *Anal. Chem.*, 59:2603–2609, 1987.

Hudson and Busch, "Studies on the Feasibility of Using Infrared Emission from a Flame as the Basis for a Non–Selective Detector for Liquid Chromatography," *Southwest Regional Meeting of ACS*, Nov. 19, 1987, Abstract No. 234.

Kubala et al., "Determination of Total Inorganic Carbon in Aqueous Samples with a Flame Infrared Emission Detector," *Analytical Chemistry*, 61:1841–1846, 1989.

Kubala et al., "Determination of Chloride and Available Chlorine in Aqueous Samples by Flame Infrared Emission," *Anal. Chem.*, 61:2785–2791, 1989.

Kubala et al., "Design and Performance of a Direct–Reading, Multichannel Spectrometer for the Determination of Chlorinated Purgeable Organic Compounds by Flame Infrared–Emission Spectrometry," *Talanta*, 38(6):589–602, 1991.

Lam et al., "An Investigation of the Signal Obtained from a Flame Infrared Emission (FIRE) Detector," *Applied Spectroscopy*, 44(2):318–325, 1990.

Lam et al., "Design and Performance of a New Continuous–Flow Sample–Introduction System for Flame Infrared–Emission Spectrometry: Applications in Process Anslysis, Flow Injection Analysis, and Ion–Exchange High–Performance Liquid Chromatogrphy," *Talanta*, 40(6):867–878, 1993.

Ravishankar et al., "Dual–Channel Flame Infrared Emission Detector for Gas Chromatograph," *Anal. Chem.*, 62:1604–1610, 1990.

Ravishankar et al., "An Element–Specific, Dual–Channel, Flame Infrared Emission, Gas Chromatography Detector for Chlorinated and Fluorinated Hydrocarbons," *Applied Spectroscopy*, 44(8):1247–1258, 1990.

Ravishankar et al., "Spatial Emission Characteristics of a Capillary–Burner Excitation Source for a Flame Infrared Emission (FIRE) Radiometer," *Applied Spectroscopy*, 45(10):1684–1694, 1991.

Thayer, "Analytical Instrumentation Market Growing Rapidly," *C&EN*, pp. 17–20, Nov. 21, 1988.

Tilotta et al., "Fourier Transform Flame Infrared Emission Spectroscopy," *Applied Spectroscopy*, 43(4):704–709, 1989.

Tilotta et al., "A Miniature Electrical Furnace as an Excitation Source for Low–Temperature, Gas–Phase, Infrared Emission Spectroscopy," *Applied Spectroscopy*, 45(2):178–185, 1991.

Tilotta et al., "Evaluation of Thermospray and Cross–Flow Pneumatic Nebulization a Means of Interfacing a Flame Infrared Emission (FIRE) Radiometer to a High–Performance Liquid Chromatograph," *Applied Spec-*

*troscopy*, 47(2):192–200, 1993.

Whitlock et al., "Continuous Monitoring of Gaseous Carbon Impurities in Electronic Grade Bulk Gases," *Microcontamination*, pp. 43–45, May, 1988.

Zhang et al., "Pre–Excitation, Catalytic Oxidation of Analytes over Hopcalite in Flame/Furnace Infrared Emission (FIRE) Spectrometry," *Applied Spectroscopy*, 46(4):631–639, 1992.

Zhang et al., "Evaluation of an Improved Burner Design for a Flame Infrared Emission (FIRE) Gas Chromatography Detector," *Applied Spectroscopy*, 46(6):930–939, 1992.

Zhang et al., "Terminal and Intermediate Combustion Products Observed from 2.0 to 5.0 µm in Flame/Furnace Infrared Emission Spectrometry," *Applied Spectroscopy*, 46(11):1673–1684, 1992.

Freiberg and Weaver, "Effects of Lasering Upon the Electron Gas and Excited–State Populations in Xenon Discharges," *Journal of Applied Physics*, 38(1):250–262, 1967.

U.S. PATENT DOCUMENTS

| Patent No. | Date | Inventor | Class |
|---|---|---|---|
| 3,854,881 | 12/1974 | Cohen | 23/253 PC |
| 3,871,768 | 3/1975 | Belcher et al. | 356/87 |
| 3,902,808 | 9/1975 | Young | 356/74 |
| 3,902,809 | 9/1975 | Sparks | 356/85 |
| 3,926,522 | 12/1975 | Andreotti | 356/51 |
| 4,068,125 | 1/1978 | Bell | 250/340 |
| 4,147,431 | 4/1979 | Mann | 356/72 |
| 4,167,334 | 9/1979 | Phillips | 356/315 |
| 4,249,168 | 2/1981 | Muggli | 340/578 |
| 4,255,051 | 3/1981 | Imamura et al. | 356/313 |
| 4,260,884 | 4/1981 | Lovelock | 250/324 |
| 4,311,485 | 1/1982 | Saltzman et al. | 23/230 R |
| 4,408,878 | 10/1983 | Fischbach | 356/43 |
| 4,466,943 | 9/1984 | Murase et al. | 422/91 |
| 4,467,435 | 8/1984 | Warnke et al. | 364/497 |
| 4,553,152 | 11/1985 | Nishitani | 357/24 |
| 4,572,668 | 2/1986 | Auth | 356/318 |
| 4,579,461 | 4/1986 | Rudolph | 374/9 |
| 4,698,314 | 10/1987 | Tao | 436/171 |
| 4,716,293 | 12/1987 | Harrick | 250/340 |
| 4,730,925 | 3/1988 | Chiba et al. | 356/311 |
| 4,810,875 | 3/1989 | Wyatt | 250/227 |
| 4,849,636 | 7/1989 | Fertig, Sr. | 250/343 |
| 5,007,428 | 4/1991 | Watmough | 128/660.04 |
| 5,153,673 | 10/1992 | Amirav | 356/315 |
| 5,246,868 | 9/1993 | Busch et al. | 436/101 |

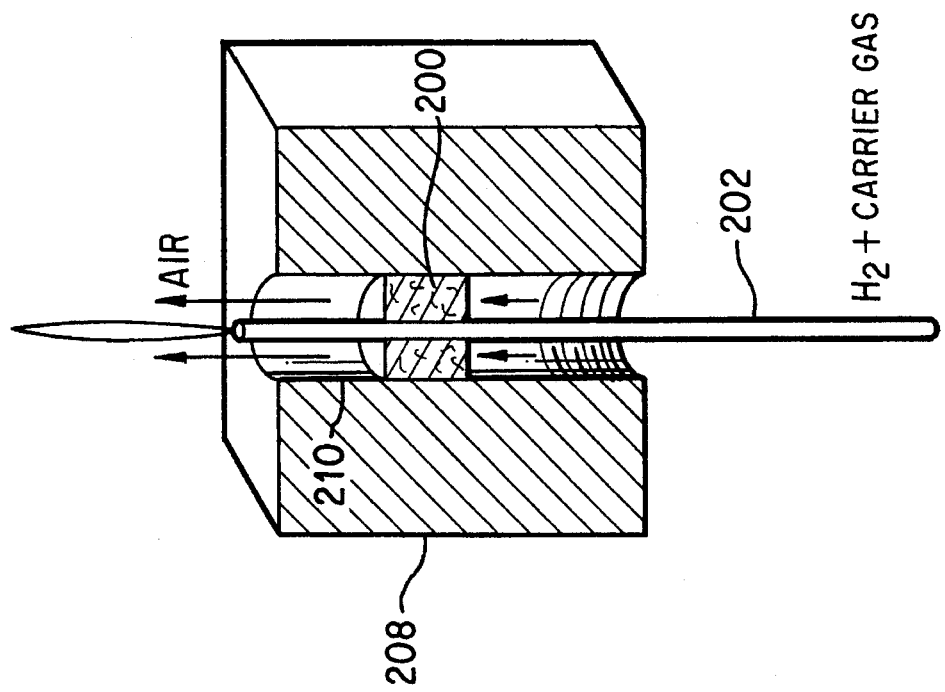
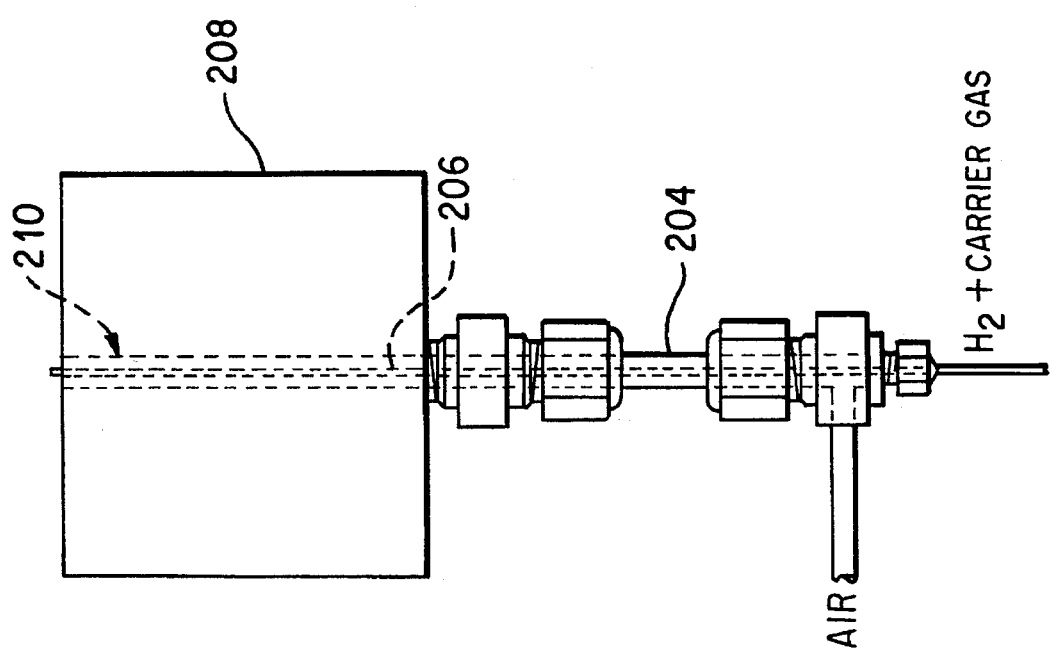

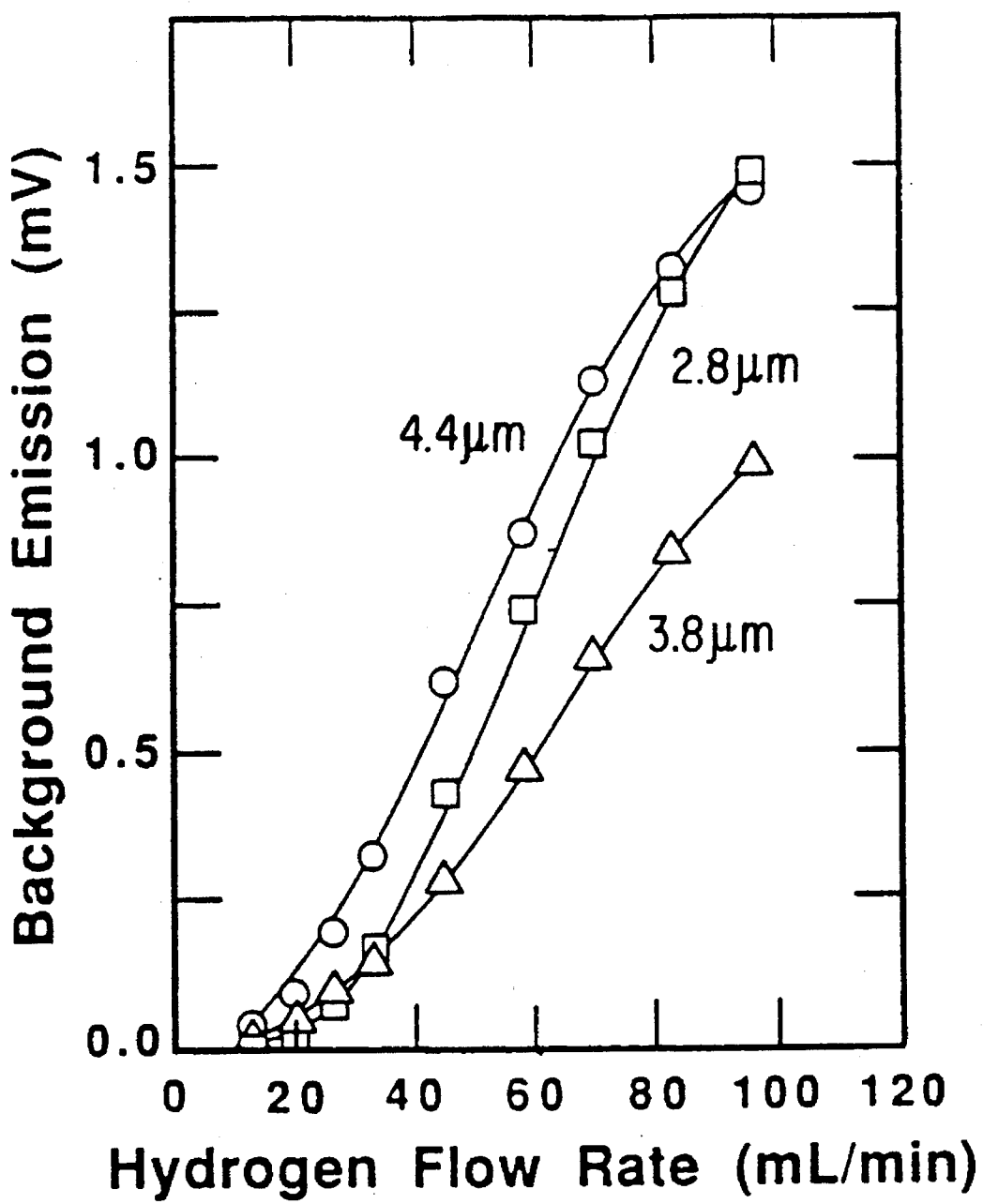
F I G. 4

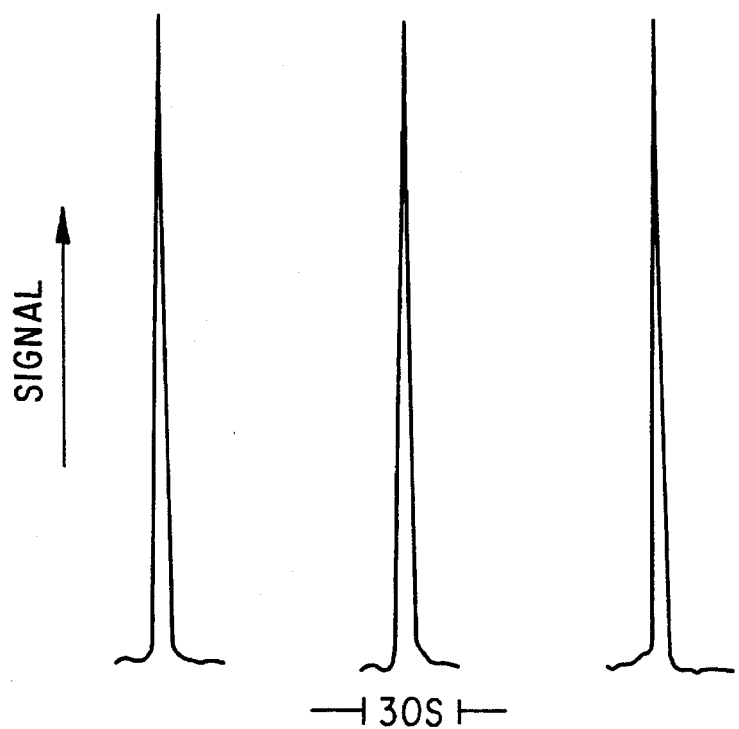
F I G. 25A
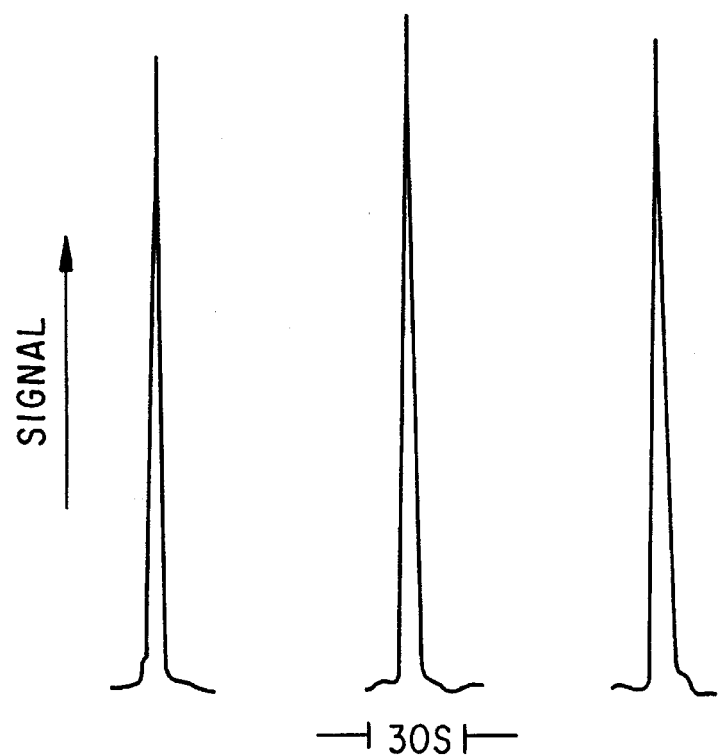
F I G. 25B

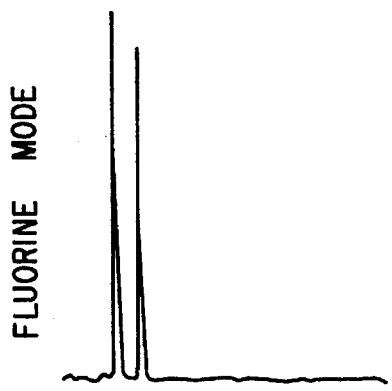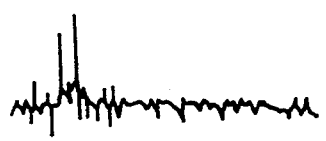
FIG.33A
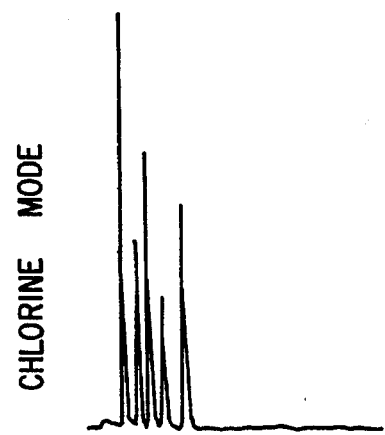
FIG.33B
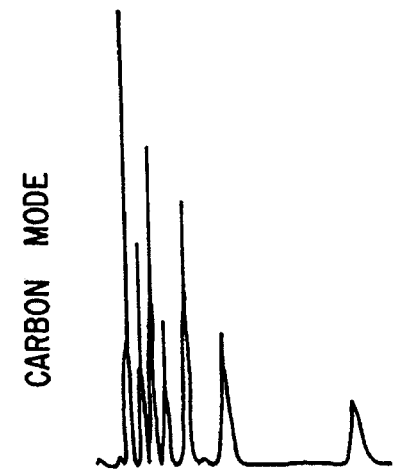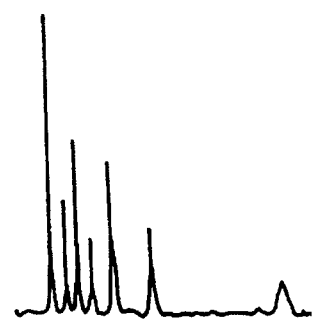
FIG.33C
SUBTRACTED MODE          UNSUBTRACTED MODE

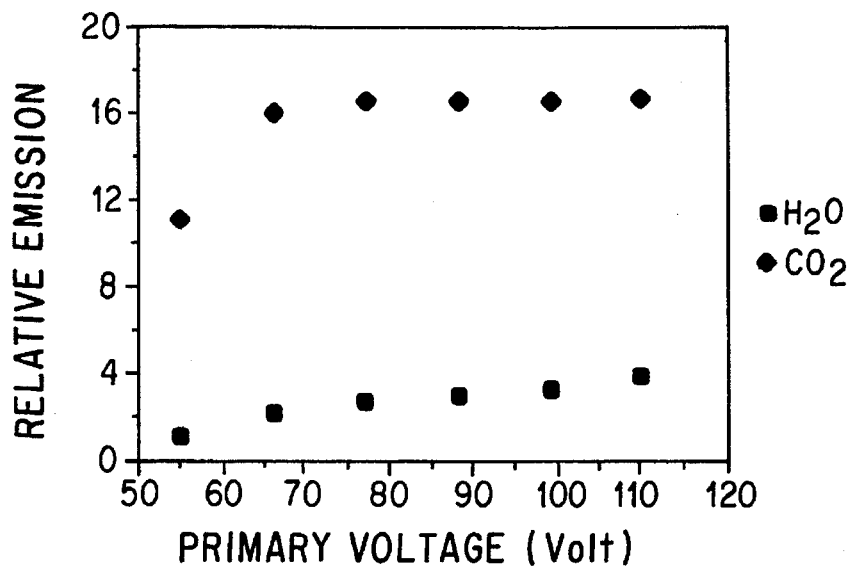
F I G. 43A
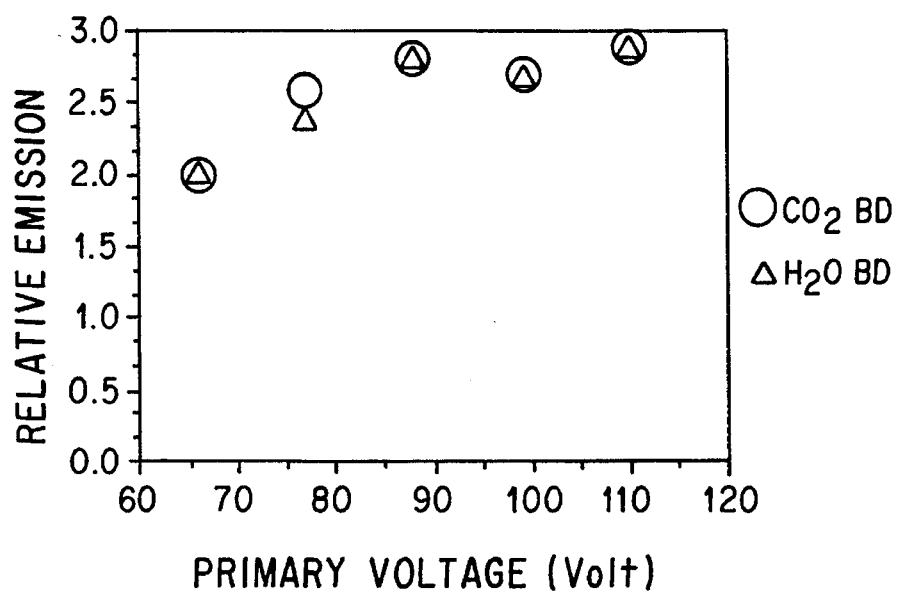
F I G. 43B

INFRARED EMISSION DETECTION OF A GAS

This application is a continuation-in-part application of Ser. No. 07/415,141 filed Sep. 29, 1989. Ser. No. 07/415,141, now U.S. Pat. No. 5,246,868. was a continuation-in-part application of Ser. No. 07/263,089 filed Oct. 26, 1988, now abandoned, which is a continuation-in-part of application Ser. No. 120,050, filed Oct. 26, 1987, now abandoned. These applications are incorporated by reference herein.

DESCRIPTION

1. Technical Field

This invention relates to infrared emission detection means and method for detecting selected molecules of interest in a gaseous sample or samples which can be converted to the gas phase. The invention is particularly applicable to the fields of gas chromatography, liquid chromatography, $CO_2$ detection, total organic carbon analysis, total inorganic carbon analysis, water analysis, environmental analysis, chlorofluorocarbon analysis, $SO_2$ analysis, process analysis and $NO_x$ analysis.

2. Prior Art

Combustion flames have long been employed analytically as spectroscopic sources. Although, the analytical application of combustion flames as spectroscopic sources has been studied in great depth, the work, to date, has been confined almost entirely to studies of the radiant emissions falling within the UV-visible region of the electromagnetic spectrum.

U.S. Pat. No. 3,836,255 describes a spectro-metric substance analyzer which monitors both emission and absorption. In this analyzer a fluid is cyclically heated and cooled wherein the radiation variation is characteristic of the substance of interest in the fluid.

U.S. Pat. No. 3,516,745 describes a method for observation of gas spectral emissions. The gas is contained in a chamber where it is cyclically compressed and allowed to expand. The variation in spectral emission can be correlated to the concentration of gas within the piston. The oscillation excites or energizes the gas contained in the chamber to give off spectral emissions.

U.S. Pat. No. 3,749,495 describes an IR emission analyzer where the sample is periodically compressed and expanded. The compressed gas becomes heated due to increased molecular collision and thereby produces infrared emissions. Comparison of the emissions of the compressed and expanded gas produces a differential emission dependent upon gas concentration.

Despite the fact that a sizable fraction of the total radiation emitted from combustion flames lies in the infrared region of the spectrum, the use of this emission for analytical purposes does not appear to have been studied.

In terms of optical radiation, the energy radiated from a combustion flame extends from the ultraviolet region of the spectrum to the far infrared region. Of the total energy radiated by the flame, emission from the ultraviolet and visible regions of the spectrum accounts for only about 0.4% (Gaydon, A. G., 1974). By contrast, it is estimated that infrared emission from a combustion flame may account for as much as 20% of the total energy radiated (Gaydon, A. G., 1979) For transparent flames such as the hydrogen/air flame, the visible emission is negligible and most of the radiated energy falls in the infrared region of the spectrum. In spite of these facts, the analytical applications of infrared emissions from combustion flames have not been studied.

Despite the lack of analytical studies, a great deal of work has been done on the infrared emissions from hot gases, primarily for the purpose of tracking jet aircraft and rockets for military applications. In much of this work, ordinary combustion flames have been employed as models for exhaust gases from airborne vehicles. Plyler (Plyler, E. K., 1948), in particular, has studied the infrared emission from a Bunsen flame over the wavelength range from 1 to 22 μm. In the wavelength interval from 1 to 5 μm, Plyler found that two bands predominate as a result of infrared emission from molecules of $CO_2$ and $H_2O$ (Plyler, E. K., 1948). One band is located at 2.7 μm (3704 cm$^{-1}$) while the other is located at 4.4 μm (2273 cm$^{-1}$).

Studies of the infrared emission of carbon dioxide have shown that $CO_2$ emits strongly at 2.8 and 4.4 μm (Gaydon, A. G., 1974) The longer wavelength band corresponds to the asymmetric stretch of the carbon dioxide molecule (Nakamoto, K., 1963). Water, on the other hand, emits at 2.5 and 2.8 μm. The infrared spectrum observed from a typical combustion flame is a result of the superposition of these two emissions as modified by atmospheric absorption. Since the position of the $CO_2$ absorption band is shifted slightly with respect to the emission band, only a portion of the emission band undergoes atmospheric absorption (Curcio, J. A., 1966). The observed band at 4.4 μm is due exclusively to carbon dioxide emission and appears shifted from the true 4.3 μm $CO_2$ emission due to an alteration in the true band shape by atmospheric absorption by $CO_2$. The band observed from the flame at 2.8 μm is a result of the overlap of the water bands at 2.5 and 2.8 μm with the carbon dioxide band at 2.8 μm and is also attenuated by atmospheric absorption by water vapor. Although other bands have been observed over the wavelength range from 1 to 22 μm, the bands at 2.7 and 4.4 μm are the two most intense emissions.

The amount of infrared emission observed from flames is also dependent on a number of other parameters. Studies of flames have shown that most of the energy is lost by conduction and convection occurring upon mixing with the cooler atmospheric air (Gaydon, A. G., 1974). In addition, turbulent flow has been observed to decrease the amount of infrared radiation emitted (Gaydon, A. G. et al., 1979). Self absorption is another factor which can reduce emission. Thus, the size, shape, and nature of the flame are important parameters when considering the amount of radiation from the flame.

In addition, the region of observation within the flame is an important consideration. Spatially, the emission of infrared radiation is observed to be a maximum in the outer cone and the surrounding gases with little or no emission from the inner conal area (Gaydon, A. G., 1974). Previous studies have shown that approximately one-seventh of the infrared emission comes from the inner conal area with the remaining six-sevenths originating in the outer cone/hot gas layer (Gaydon, A. G., 1974). The hot gaseous combustion products formed in the flame continue to emit above the visible portion of the outer cone until they are cooled by the entrainment of atmospheric air.

Finally, and most importantly from an analytical standpoint, the amount of infrared radiation emitted from the flame is a function of the number of $CO_2$ and $H_2O$ molecules present in the hot gases. Thus both quantitative and qualitative analyses are possible.

BRIEF DESCRIPTION OF THE DRAWINGS

FIGS. 2A and 2B show schematic diagrams of the concentric, two-tube burner. (2A) Side view of burner showing tubing connections. (2B) Cross-section of burner body showing arrangement of the two concentric tubes and glass wool plug; 200— glass wool plug, 202—1/16" stainless steel tubing, 204—3/16" stainless steel tubing, 206—central capillary, 208—aluminum block, 210—outer stainless steel sheath.

FIG. 4 shows the background emission intensity (mV) in the 4.4-µm (o), 3.8-µm (Δ), and 2.8-µm (□) channels as a function of hydrogen flow rate for the concentric, two-tube burner when used in conjunction with the 15-m×0.53-mm SPB-20 silica capillary column. Other operating conditions identical to those of FIG. 3.

FIGS. 25A and 25B are hydrogen chloride signal profiles obtained by (A) treatment of an acidified aliquot of an NaCl solution with saturated $KMnO_4$ and (B) addition of concentrated sulfuric acid to a bleach sample.

FIGS. 33A to 33C are flame infrared emission chromatograms illustrating the relative performance of the subtracted and unsubtracted modes of operation in three selective modes.

FIGS. 43A and 43B show the primary voltage effect on emission from hexane in air arc discharge (32A) and the primary coil voltage effect on background emission (32B).

SUMMARY OF THE INVENTION

Figure 1:
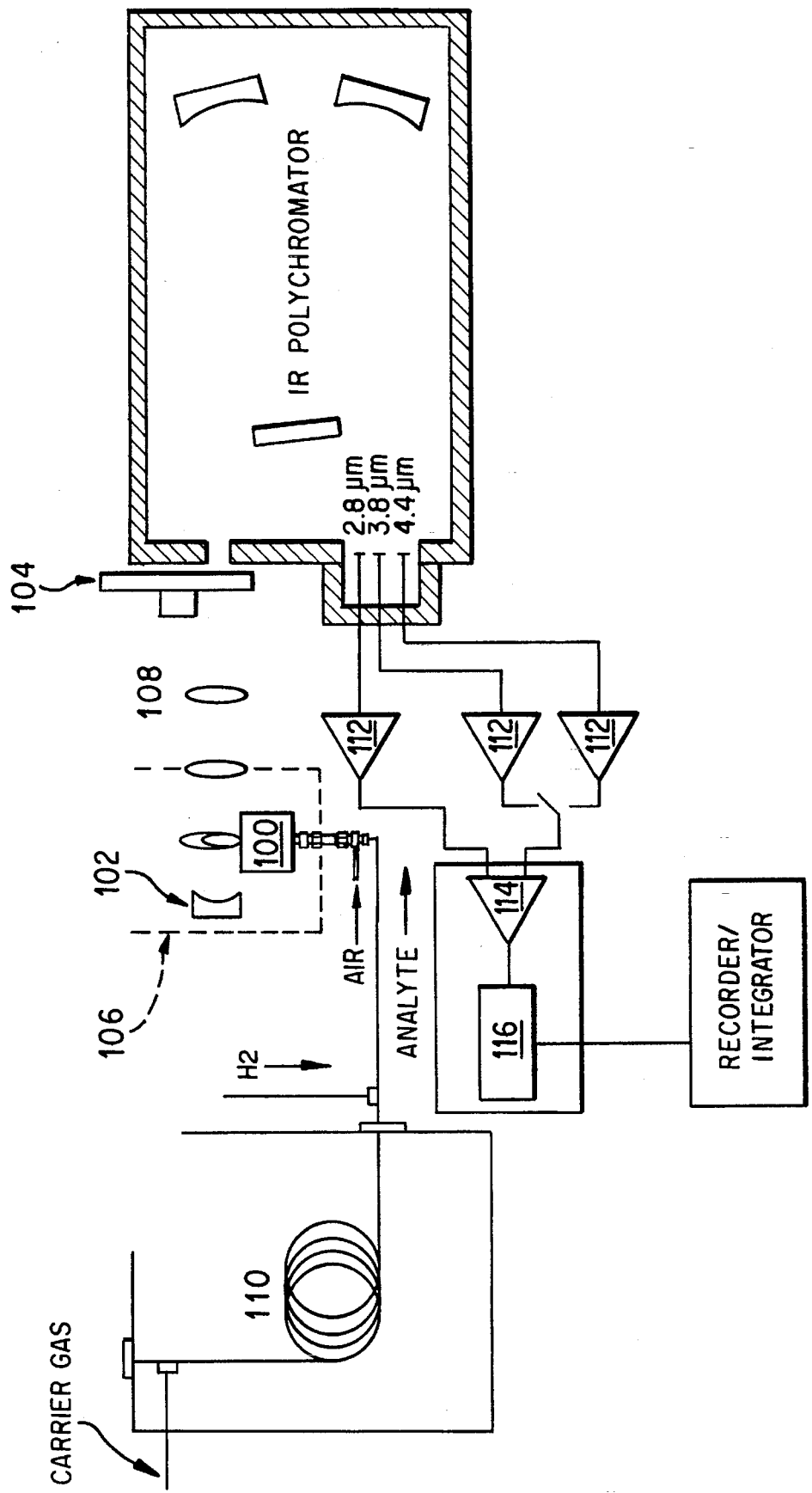
FIG. 1 shows a schematic diagram of the FIRE-GC detection system showing placement of the new, concentric, two-tube burner. Key: 100, concentric, two-tube burner; 102, back-collection mirror; 104, chopper; 106, chimney; 108, collection optics; 110, gas chromatograph; 112, detector preamplifiers; 114, differential input of lock-in amplifier; 116, phase-sensitive detector.

The present invention relates to infrared emission detection means and method whereby the infrared emission of excited molecules of interest in a sample is used as a basis for detection of compounds.

In one aspect of the invention, infrared emission is observed as a means of detection for chromatography. Organic compounds introduced into an excitation means result in the production of carbon dioxide which allows observation of two strong emission bands over the wavelength range from 1 to 5 μm. Other infrared active species could be produced as well over the entire infrared region.

Both total organic carbon (TOC) and total inorganic carbon (TIC) determinations in aqueous samples can be made. Total inorganic carbon and total organic carbon are important analytical parameters in the environmental characterization of water. Total organic carbon determinations are performed routinely as a non-specific measure of the organic content of water in pollution monitoring. Inorganic carbon exists in water as bicarbonate and carbonate ions and as dissolved carbon dioxide. The sum of these carbon species is called Total Inorganic Carbon (TIC). TIC can be determined directly by acidification of the sample to convert bicarbonate and carbonate ions into dissolved $CO_2$, purging of the sample with a suitable gas to remove the dissolved $CO_2$, and measurement of the $CO_2$ (usually by infrared absorption). Total inorganic carbon determinations by infrared emission detection can be used in place of alkalinity titrations to determine the amount of inorganic carbonate present in a water sample.

Infrared emission detection can be used to monitor carbon impurities in electronic grade gases. Carbon/hydrogen characterization of compounds by infrared emission detection is possible by observing the two strong emission bands, one associated with carbon dioxide and one with both water and carbon dioxide. Molecules or molecular fragments containing heteroatoms can be observed by Fourier transform infrared emission spectroscopy. In that many biochemical reactions result in the release of carbon dioxide as a by-product, infrared emission detection can provide the basis for a variety of clinical and biochemical assays.

The infrared emission detection system finds application in the determination of chloride and available chlorine in aqueous samples. The chlorine analysis method includes means for pretreating the sample to evolve chlorine gas. Samples containing aqueous chloride are pretreated with a strong oxidant such as permanganate ion, peroxide ion or $MnO_2$ thereby forming chlorine gas. Samples containing available chlorine due to dissolved molecular chlorine, hypochlorous acid and/or hypochlorite ion are pretreated with acid thereby rapidly generating molecular chlorine gas. The molecular chlorine gas is then liberated from the sample and reacted with hydrogen to form HCl which is excited to emit a characteristic infrared radiation pattern which is detected. In a preferred embodiment, the infrared emission detector is a flame infrared emission detector wherein the flame is a hydrogen/entrained-air flame. In this preferred embodiment, the chlorine gas reacts with hydrogen from the flame to form HCl. The HCl is excited by the flame and exhibits a strong, well-resolved emission band which lies between those for water and carbon dioxide. A 3.8 μm bandpass filter in the infrared emission detector is used to monitor the emission band and subsequently determine the concentration of chloride and available chlorine in the sample.

The performance of the basic infrared emission detector is improved substantially by the use of a dual beam system with background subtraction capability. The selectivity ratio and detection limits are optimized by adjusting the detector bias voltage, using an optical filter in the reference channel for background compensation and balancing the Wheatstone bridge network. The improved detector can therefore detect smaller quantities of species of interest. A preferred embodiment is the use of the improved detector for the detection of carbon compounds, chlorinated compounds, fluorinated compounds as well as chlorofluorocarbons.

An electrical furnace may serve as an excitation source. Compared to the hydrogen/air flame, a variable-temperature electrical furnace greatly reduces background emission from water vapor and allows emission from the parent analyte in addition to emission from combustion products.

Electrical excitation means includes electron impact in a gas discharge and excitation by collisions with a vibrationally excited diatomic molecule. This means of excitation does not increase the kinetic energy of the gases involved and emission is achieved at near room temperature.

The present invention provides an apparatus for detecting and making quantitative measurements of at least one selected component in a sample, in which at least one selected component of the sample, or at least one selected substance produced from the at least one selected component in the sample and characteristic of the at least one selected component, is introduced into an exciting means. When the at least one selected component is present in the sample, gas-phase infrared-active molecules emit infrared radiation at at least one characteristic wavelength in proportion to the quantity of the at least one selected component in the sample. This first embodiment comprises means for exciting the gas-phase, infrared-active molecules to emit radiation over a given path and infrared discriminating and detector means located on said given path for detecting infrared radiation at the at least one characteristic wavelength and for generating an output signal representative thereof, and thereby determining the quantity of the at least one selected component in the sample. When the at least one selected component is present in the sample, the gas-phase infrared-active molecules emit radiation at the at least one characteristic wavelength with an intensity proportional to the quantity of the at least one selected component in the sample.

The infrared discriminating and detector means may include a wavelength discriminating means located on said path, between the exciting means and the infrared detector means, for allowing the at least one characteristic wavelength to pass from the exciting means to the detector means while inhibiting the passage of other wavelengths, means for separating the wavelengths of the emitted radiation into an infrared spectrum, or a monochromator. Multiple infrared discriminating and detector means may be used in the apparatus. The apparatus may further include a computer means, responsive to an output signal from the infrared detector means, for performing signal processing thereon to provide an output indicative of the quantity of the at least one selected component present in the sample. The infrared discriminating and detector means may include an interferometer or an interferometer and a computer means, coupled to the interferometer, for performing a Fourier transform analysis on an output signal from the interferometer to thereby obtain a spectral analysis characteristic of the sample. The apparatus may include vaporizing means for vaporizing a liquid sample and for conducting the resultant vapors into the exciting means. The means for exciting the gas-phase, infrared-active molecules may include furnace excitation, excitation by electron impact in a gas discharge or excitation by collisions with a vibrationally excited diatomic molecule. The infrared detector means may include a thermal infrared detector or a quantum detector.

The at least one selected component or the at least one selected substance may contain carbonates or calcinates, and in that case, the apparatus further includes means for acidifying the at least one selected component or the at least one selected substance to generate $CO_2$ which is then introduced into the exciting means. The at least one selected component or the at least one selected substance may contain carbon-containing compounds, and in that case, the apparatus further includes means for oxidizing the at least one selected component or the at least one selected substance to generate $CO_2$ which is then introduced into the exciting means. The means for oxidizing may be included in the exciting means. The at least one selected component or the at least one selected substance may contain hypochlorous acid or hypochlorite ions, and in that case, the apparatus further includes means for acidifying the at least one selected component or the at least one selected substance with HCl to generate $Cl_2$ which is then introduced into the exciting means. The at least one selected component or the at least one selected substance may contain chloride ions, and in that case, the apparatus further includes means for oxidizing and acidifying the at least one selected component or the at least one selected substance to generate chlorine $Cl_2$ which is then introduced into the exciting means. The at least one selected component or the at least one selected substance may include chlorine-containing or fluorine-containing organic compounds, and in that case, the exciting means includes a means for combusting the at least one selected component or the at least one selected substance to thereby generate HCl or HF, respectively, which is then introduced into the exciting means.

A second embodiment of the present invention is an apparatus comprising means for exciting the gas-phase, infrared-active molecules to emit radiation along a first path, beam splitting means disposed on said first path for directing a portion of the emitted infrared radiation over a second path; first and second infrared detector means located on said first and second paths respectively, first wavelength discriminating means located on said first path between said beam splitting means and said first detector means, and second wavelength discriminating means located on said second path between said beam splitting means and said second detector means, and means connected to the first and second detector means for combining the first and second electrical signals to thereby cause a cancellation of fluctuations in intensity at the at least one characteristic wavelength caused by fluctuations in the background radiation.

When the at least one selected component is present in the sample, the gas-phase, infrared-active molecules emit radiation at at least one characteristic wavelength with an intensity proportional to the quantity of the at least one selected component in the sample, and the exciting means simultaneously emits fluctuating background radiation along said first path at the at least one characteristic wavelength of the gas-phase, infrared-active molecules and at other wavelengths. The first detector means generates a first electrical signal responsive to emitted radiation at the at least one characteristic wavelength, and the second detector means generates a second electrical signal responsive to the simultaneously emitted background radiation. The first wavelength discriminating means allows passage of radiation at the at least one characteristic wavelength and inhibits the passage of other wavelengths, and the second wavelength discriminating means allows passage of the emitted background radiation and inhibits the passage of radiation at the at least one characteristic wavelength. The means for combining includes means for subtracting the second electrical signal from the first electrical signal. This embodiment may further include optical attenuating means, located on the second path between the beam splitting means and the second detector means, for adjusting the level of the second output signal. The first and second detector means may be coupled to a biasing circuit means for achieving equalization of the first and second output signals. The means for exciting the gas-phase, infrared-active molecules may include furnace excitation, excitation by electron impact in a gas discharge or excitation by collisions with a vibrationally excited diatomic molecule.

A method for using the first embodiment of the present invention includes the steps of i) exciting the gas-phase, infrared-active molecules to emit radiation, and ii) selectively detecting infrared radiation emitted at the at least one characteristic wavelength and generating an output signal representative thereof, and thereby determining the quantity of the at least one selected component in the sample. The method may include the step of discriminating the at least one characteristic wavelength by allowing only the at least one characteristic wavelength to be detected in the detecting step while inhibiting the detection of other wavelengths. The discriminating step may include separating the wavelengths of the emitted radiation into an infrared spectrum and may use a monochromator or an interferometer. The discriminating step may include use of a computer coupled to the interferometer for performing a Fourier transform analysis on an output signal from the interferometer to thereby obtain a spectral analysis characteristic of the sample. The method may further include the step of utilizing a computer for performing signal processing on the output signal produced by said detecting step to provide an output indicative of the quantity of the at least one selected component present in the sample or the step of vaporizing a liquid sample and utilizing the resultant vapors in said exciting step.

The exciting step may include thermal excitation, excitation by electron impact in a gas discharge or excitation by collisions with a vibrationally excited diatomic molecule.

A method for using the second embodiment of the present invention includes the steps of i) exciting the gas-phase, infrared-active molecules to emit radiation, ii) splitting the emitted radiation into first and second beams; iii) first detecting radiation in the first beam at the at least one characteristic wavelength, and generating a first electrical signal representative of the emitted radiation at at least one characteristic wavelength, and secondly detecting radiation in the second beam having the emitted background radiation and generating a second electrical signal representative of the simultaneously emitted background radiation; and iv) combining the first and second electrical signals to cancel fluctuations in intensity at the at least one characteristic wavelength caused by fluctuations in the background radiation.

The first detecting step includes discriminating the at least one characteristic wavelength by allowing passage of radiation at the at least one characteristic wavelength and inhibiting the passage of other wavelengths, and the second detecting step includes discriminating against the at least one characteristic wavelength by allowing passage of the emitted background radiation and inhibiting the passage of radiation at the at least one characteristic wavelength. The combining step includes subtracting the second electrical signal from the first electrical signal. The method may further include attenuating the second beam to adjust the level of the second output signal. Exciting the gas-phase, infrared-active molecules may occur by furnace excitation, excitation by electron impact in a gas discharge or excitation by collisions with a vibrationally excited diatomic molecule.

DETAILED DESCRIPTION OF THE INVENTION

The present invention relates to an infrared detection means and a method for detecting selected molecules of interest in a gaseous sample or samples which can be converted to the gas phase. The infrared detection means includes a detector means and a means for exciting molecules of interest in the sample to emit a characteristic infrared radiation pattern. In one embodiment, heating by a flame is employed to combust and excite the molecules of interest in the sample to produce vibrationally excited molecules such as carbon dioxide which can emit infrared radiation. A pre-determined wavelength of infrared radiation emitted by the molecules of interest is observed with a detector that generates an electrical signal in response to the emission at the observed wavelength. The observation wavelength is preselected from the characteristic infrared radiation pattern of the molecule of interest. The means for isolating a preselected wavelength of infrared radiation is mounted between the exciting and detector means.

A factor necessary for successful implementation of infrared emission is to achieve a useful level of contrast between the source and the background, that is the source should be at a higher temperature than the surrounding background, and the temperature of the source should be greater than the temperature of the detector. For this reason, one would not expect to see infrared emission from a gas at room temperature if the background and the detector are also at room temperature. Therefore, the first requirement for the successful implementation of this technique is in most cases a means to heat the gas above room temperature. This does not necessarily mean that a flame is required. However, within the limits of molecular stability, the hotter the gases, the greater the radiant emissivity, and the more sensitive the detection system. Since flames typically have temperatures on the order of 1000–3000 K, they represent potentially good emission sources for this application if a low-background flame in the vicinity of the selected emission band can be found.

It should be stressed, however, that other means could be used to excite the gases so that they would emit infrared bands. Other excitation means include: 1) other thermal excitation such as a furnace excitation; 2) excitation by electron impact in a gas discharge; 3) excitation by collisions of the second kind with a vibrationally excited diatomic molecule (similar to the mechanism used in the carbon dioxide laser); and 4) photo-excitation with an appropriate source. Photoexcitation can be accomplished from the 000 level of $CO_2$ (resonance excitation) or from the 010 level which is appreciably populated even at room temperature (non-resonance excitation). Such infrared fluorescence could be conveniently excited with a carbon dioxide laser emitting radiation at 10.6 µm. Absorption of such radiation would cause the transition from 010 to 001.

A second requirement for high sensitivity is the avoidance of the use of any form of solid containment such as a sample cell. In order to see infrared emission, there must be some contrast between the infrared emitting source (i.e., the gas in this case) and the background as a result of a thermal gradient. When a heated gas is introduced into a solid sample container, however, the gas immediately begins to heat the container and the thermal gradient and the contrast gradually disappear with time as the system reaches thermal equilibrium. As a result of this process, the emission signal, which is initially present from the gas because it is hotter than the walls of the cavity, gradually fades into the background until it disappears. As a result of this phenomenon, previous experiments had to employ complicated recirculating systems so that hot gases and cold gases could be alternately admitted into the sample cell at a rate sufficiently great that the system would not have time to reach thermal equilibrium (i.e., use of thermal cycling). If no sample containment is used, as with a flame, there is no blackbody radiator to heat up in the vicinity of the emitting gases, and a steady-state emission signal can be observed. This emission signal is present as long as sample is introduced into the flame, and does not decay away with time as would be the case with the previous systems where the background gradually increases. For this reason, thermal cycling is unnecessary with the present system.

Use of a high temperature excitation source is also beneficial in reducing the effects of atmospheric absorption (i.e., telluric absorption when observing $CO_2$ emission) due to carbon dioxide in the atmosphere. As a gas is heated, various upper level vibrational states become populated, and transitions between upper levels occur. Thus, the emission band observed for a hot gas contains components arising from upper level vibrational transitions (say, v=4 to v=3) and is therefore broadened and shifted somewhat to longer wavelengths as the temperature is increased. By contrast, carbon dioxide at room temperature is present mainly in the lowest vibrational level (v=0). Since the emission band is shifted with respect to the absorption band (because the emitters are at a higher temperature than the absorbers), atmospheric absorption by carbon dioxide is not a significant problem.

Finally, when $CO_2$ emission is being observed in a flame, a flame must be chosen which does not itself produce or contain carbon dioxide. This excludes the use of all carbon-containing fuels, and suggests the use of hydrogen-fueled flames. Two possibilities exist—the hydrogen/air flame and the hydrogen/oxygen flame. Of the two, the hydrogen/air flame is more convenient because it has a lower burning velocity which makes it easier to design a burner which will not flash-back (i.e., explode). The hydrogen/oxygen flame may produce a larger signal because of its higher temperature. Although one of the carbon dioxide emission bands is overlapped with two water emission bands in the hydrogen/air flame (producing a composite band at 2.7 µm), the region at 4.4 µm where the only other carbon dioxide emission occurs is clear of any other potentially interfering flame background. For these reasons, the hydrogen/air flame was selected as an excitation source for preliminary studies of flame infrared $CO_2$ emission.

Many detectors sensitive in the infrared are also sensitive in the UV/visible, although they are generally not used in this region because they are considerably less sensitive than other available detectors such as the photomultiplier. The photomultiplier is based on the external photoelectric effect whereby a photon absorbed by a suitable photoemissive material is ejected from the material into the surrounding vacuum. To give the electron sufficient energy to escape the surface of the photoemitter, the photon absorbed must possess an energy greater than the sum of the energy bandgap and electron affinity of the photoemitter. Detectors based on photoemission of electrons as a result of the photoelectric effect can be made very sensitive by the use of electron multiplication with a dynode chain. Thus, photomultipliers can be made so sensitive that they are often limited by the fluctuation in the arrival rate of photons rather than fluctuations arising within the detector itself. Unfortunately, the energy requirement for external photoemission is sufficiently large that the use of photomultipliers is confined essentially to the UV/visible region of the spectrum. By reducing the electron affinity of certain photoemitters, photomultipliers that respond to longer wavelengths beyond the visible (out to about 950 nm) have been produced.

Detectors which respond to infrared radiation can be classified into two basic categories: thermal detectors and quantum detectors. Thermal detectors respond to the heating effect of the infrared radiation and include thermocouples, thermistors, and pyroelectric detectors. Quantum detectors make use of the internal photoelectric effect whereby an electron is promoted from the valence band to the conduction band but is not ejected from the material. As a result, these detectors respond out to wavelengths whose energies correspond to the semiconductor bandgap. These detectors include photovoltaic and photoconductive detectors. Neither category of detector discussed above employs any form of internal amplification comparable to the photomultiplier and for this reason, IR detectors are less sensitive than detectors commonly used for the detection of UV/visible radiation. Since the major source of noise with these detectors originates within the detector itself and is not due to fluctuations in the radiation field, these detectors are frequently cooled to reduce detector noise, and spectrometers which employ them are termed detector-noise limited.

Of the various infrared detectors which are available, quantum detectors generally have a higher specific detectivity than thermal detectors, although thermal detectors have the advantage of flat response over a wide wavelength range. For simplicity, a detector which did not require cooling to dry ice or liquid nitrogen temperatures was desired. For the wavelength region under consideration (2–5 µm), the lead selenide and indium antimonide detectors were two possibilities. Of the two, the indium antimonide had the higher specific detectivity but generally required cooling. For this reason, the PbSe detector was selected as the most appropriate for preliminary studies on the basis of spectral response and cost. Even with the PbSe detector, however, some thermoelectric cooling may be beneficial to shift the maximum response of the detector to longer wavelengths.

To detect the 4.4 µm emission band from carbon dioxide without interference from other emission bands (such as the one at 2.7 µm), some form of wavelength discrimination or isolation was needed. Because the radiation throughput of a conventional grating monochromator can be relatively small, these systems have not been completely satisfactory in the infrared region, and for this reason, Fourier-transform methods are often useful. However, for single molecule response a filter is satisfactory, and therefore a bandpass filter which would transmit the desired band was selected. In this way, the desired band was isolated without reducing the radiation throughput to the detector.

In the visible region of the spectrum, the advantage of emission measurements over absorption measurements is well known among spectroscopists. In view of this, it is surprising that no one thought to exploit this advantage in the infrared. The reason, no doubt, lies in the intuitive, but completely erroneous, notion prevalent among chemists that emission is less sensitive than absorption because emission is based on monitoring excited state populations whereas absorption employs ground state populations. Since everyone knows that the ground state is more populated than any excited states, it follows, ergo, that absorption must be more sensitive than emission. The great fallacy in this argument is the fact that it is irrelevant.

In fact, the reason that absorption measurements are less sensitive than the corresponding emission experiment is due to the fact that as the detection limit is approached, the absorbance, which is the logarithm of the ratio of the incident beam intensity to the transmitted beam intensity, approaches zero. This means that the magnitude of the transmitted beam intensity approaches the magnitude of the incident beam intensity. The question of detection then revolves around whether it is possible statistically to tell the difference between these two large numbers. It is well known from statistics, that differences between two large numbers, which are close to one another in magnitude and which fluctuate, are often not significant. In emission, by contrast, the detection limit occurs when the signal cannot be statistically distinguished from the background. Since the background is hopefully small, this situation is equivalent to the difference between two small numbers which is statistically more reliable. In addition, emission measurements are usually linear over a much wider range of concentrations. Thus, use of emission measurements rather than absorption measurements is based on sound analytical reasoning and is not simply an alternative way of accomplishing the same thing (Busch and Busch, 1991c).

It is instructive to point out that, if a flame is used to combust and convert the sample into carbon dioxide, the sensitivity with which this carbon dioxide could be monitored by absorption measurements is likely to be poor. Again, the reason is based on an understanding of Kirchoff's law. Ideally, for greatest sensitivity, if the carbon dioxide produced by the flame were to be monitored by absorption measurements, a blackbody emission source hotter than the temperature of the flame gases would be required. Since flame temperatures are often 2300 K., finding a solid blackbody source which is hotter than the flame is unlikely to say the least.

Process gases are those gases used in manufacturing and electronic-grade gases in particular are those gases used in the manufacture of electronic devices. Impurities such as CO, $CO_2$, and trace hydrocarbons in gases used in the manufacture of semiconductor devices must be controlled to assure reliable manufacturing conditions. Concentrations of impurities as low as 0.5 to 1 ppmv in nitrogen and argon have been reported to cause difficulties (Whitlock, W. H. et al., 1988). Currently, one method for determination of the above impurities is carried out using a flame-ionization detector (FID) in conjunction with instruments based on gas chromatography. Because the FID does not respond to either CO or $CO_2$, a catalyst system using nickel as the catalyst must be employed to convert the CO and $CO_2$ to methane. The need for the catalytic methanator and complex valving makes the current technology less than ideal.

By contrast, the infrared emission detector has good sensitivity to CO, $CO_2$, and the light gaseous hydrocarbons. Since the catalytic methanator is not needed, problems with the methanation catalyst and complex valving are not encountered. Furthermore, a continuous-monitoring technique is possible with the infrared emission system. In such a system, three gas streams can be analyzed simultaneously. One stream is fed into a flame directly. This stream measures the total impurity concentration (i.e., CO, $CO_2$, and hydrocarbons) ($S_1$). A second stream passes first through a bed of a CO absorbent prior to entering a second infrared emission detector. This stream measures the sum of the $CO_2$ and hydrocarbons ($S_2$). A third stream passes first through a bed of $CO_2$ absorber (Ascarite) prior to entering a third infrared emission detector. This stream measures the sum of the CO and hydrocarbons ($S_3$). The signals from the three streams relate to the impurity concentrations as follows:

$$S_2+S_3-S_1=\text{hydrocarbons}$$

$$S_1-S_3=CO_2$$

$$S_1-S_2=CO$$

By measuring combinations of components simultaneously, the infrared emission system has a multiplex advantage over systems which measure one component at a time.

Another major application of infrared emission technology is for water analysis. This includes drinking water (potable water), environmental samples, wastewater, and even clay-based drilling muds used in petroleum production (i.e., oil rigs). This application falls into two major categories: total inorganic carbon- and organic carbon determinations.

The presence of carbonates in water and other fluids often has a deleterious effect on the use of these liquids. For example, the presence of dissolved carbonates along with dissolved calcium can lead to scale formation in both domestic and industrial plumbing systems. Scale formation in plumbing systems not only impedes fluid flow but reduces the heat transfer efficiency of the fluid when used for cooling purposes. In petroleum production, the presence of carbonates adversely affects the performance of deflocculated clay-based drilling muds (Garrett, R. L., 1978).

In current water technology practice, the carbonate concentration is determined indirectly by means of alkalinity titrations. The alkalinity of a water sample is determined from the proton condition of the solution as $$C_B-C_A=[\text{Alk}]=[HCO_3^-]+2[CO_3^{2-}]+[OH^-]-[H^+]$$

$$[\text{Alk}]=\alpha_1 C_T+2\alpha_2 C_T+[OH^-]-[H^+]$$

where $C_A$=concentration of strong acid
$C_B$=concentration of strong base
$C_T=[H_2CO_3]+[HCO_3^-]+[CO_3^{2-}]$
$D=([H^+]^2+K_1[H^+]+K_1K_2)$
$\alpha_1=K_1[H^+]/D$
$\alpha_2=K_1K_2/D$ and $K_1$ and $K_2$ are the first and second dissociation constants of carbonic acid. The alkalinity of a water sample is also a measure of the acid neutralizing capacity of the solution.

By titrating a water sample with strong acid ($H_2SO_4$) to a methyl orange endpoint, the total alkalinity of a water sample is determined. The total inorganic carbon or $C_T$ is determined from a knowledge of the alkalinity by rearranging the alkalinity relationship:

$$C_T=([Alk]-[OH^-]+[H^+])/(\alpha_1+2\alpha_2) \; C_T \sim [Alk]/(\alpha_1+2\alpha_2)$$

Thus, as long as there are no other alkaline materials in the water besides carbonate, the alkalinity and the pH of the solution are all that is needed to determine $C_T$. In certain determinations, however, such as drilling muds, there are appreciable amounts of other alkaline materials present which make alkalinity titration data unreliable as a means of determining $C_T$. Even in the absence of other interferences, the alkalinity titration is difficult to perform because the indicator endpoint is not sharp. Even when potentiometric titrations are performed, the endpoint is still not sharp because the sample is being titrated back to carbonic acid.

By contrast, the infrared emission TIC determination is simple, convenient and direct. By direct, it is meant that the infrared emission measures $C_T$ directly rather than a property which is related to $C_T$ (i.e., the acid neutralizing capacity). The use of a direct measurement technique leads to more reliable data on the actual parameter of interest. The direct measurement does not require a knowledge of the dissociation constants for carbonic acid to calculate the desired parameter from the measured quantity.

In the infrared emission procedure, sulfuric acid (0.5 mL) is introduced into a fitted sparging tube where it is subsequently degassed. A water sample (1 mL) is added to release carbon dioxide gas which is flushed with helium into a hydrogen/air flame. The infrared emission from carbon dioxide is measured with an infrared emission detector as described previously. A calibration curve prepared from standard carbonate solutions is used to determine the total inorganic carbon concentration in the sample.

Infrared emission detection is also useful in determining the carbon dioxide content in carbonated beverages such as soft drinks and beer.

Organic materials in water samples may arise from naturally occurring compounds produced by living organisms or from anthropogenic sources. The sum of the naturally occurring organic materials and the synthetic organic materials is referred to as the total organic carbon in the water sample. Thus, the total organic carbon content of a sample is a non-specific (i.e., doesn't determine the actual individual compounds present) measure of the organic content of the sample. Total organic carbon (TOC) determinations are performed on a wide range of samples, including ground water, drinking water, semiconductor process water, municipal wastewater, and industrial wastewater (Small, R. A. et al., 1986). Industrial applications of TOC determinations include determination of organic contamination in mineral products such as acids, caustic solutions, as well as aluminum-, nickel-, and cobalt chlorides. Power generation plants use TOC measurements to determine organic contaminants in cooling water and steam-generation water. Even small amounts of formic- and acetic acid can cause corrosion of turbine blades and heat exchanger equipment (Bernard, B. B., 1985). Since an increase in the organic content of water can be an indication of pollution, TOC determinations have been used to monitor surface water, ground water (i.e., wells), and other water sources for wastewater contamination and industrial effluents.

Currently, TOC determinations are performed by first oxidizing the organic material to carbon dioxide by a variety of methods (Small, R. A. et al., 1986). The carbon dioxide gas generated by this oxidation is then determined by non-dispersive infrared (NDIR) absorption spectrophotometry. Although a variety of NDIR procedures have been employed, a primary problem with absorption measurements is the concomitant absorption by water vapor and acid gases. Partial elimination of the water vapor interference has been achieved through humidity control of the reaction gases flushed into the infrared absorption cell. Because measurements are made in absorption, all TOC analyzers require an infrared emission source to produce the infrared radiation.

With the infrared emission system, carbon dioxide is produced by the same methods currently used to oxidize organic materials to $CO_2$ (Lam et al., 1993). These oxidation methods include one or a combination of the following: chemical methods such as the use of peroxydisulfate, heating such as in a furnace with copper oxide and the use of UV radiation. After oxidation, the $CO_2$ is flushed out of the sample to the infrared emission detector.

Alternatively, for some compounds if the infrared emission detector uses a flame for exciting the molecules of interest in the sample, the sample may be combusted directly in the flame to generate $CO_2$. By utilizing infrared emission instead of absorption of $CO_2$ the interference by other concomitants produced by the oxidation process is avoided. Since the infrared emission detector is not affected by water vapor and acid gases, these interferences are absent with the infrared emission TOC analyzer. Since the infrared emission system employs a filter, it falls in the category of non-dispersive infrared analysis (only in emission rather than absorption).

Since two strong emission bands are observed in the flame, one corresponding to the asymmetric stretching vibration of carbon dioxide and the other to water and carbon dioxide combination bands, carbon/hydrogen characterization of compounds is possible by using both bands. In the combustion of any organic material, carbon dioxide, water vapor, and other combustion products are produced. The presence of carbon dioxide and water alters the intensities of the water band at 2.0–3.5 µm in addition to the carbon dioxide band at 4.25–4.8 µm. Thus, a chromatography infrared emission detector monitoring both of these bands provides additional information about the compound beyond that available with an FID or thermal conductivity detector. Although this system may not be able to determine the carbon/hydrogen ratio with the same precision as conventional combustion analysis, it distinguishes different alkanes, alkenes, aromatics, et cetera. A carbon to hydrogen ratio instrument is useful for combustion monitoring, as in smoke stack and rocket engine firing monitoring.

The infrared emission detector is useful as a detector in conventional carbon/hydrogen analyses (as opposed to using it as a detector in chromatography). As with the TOC analyses, the infrared emission system is used as the detection means in the analysis. Thus, an instrumental carbon/hydrogen analyzer can use conventional combustion tube techniques to transform the organic material into water and carbon dioxide. The infrared emission is then used to detect the amounts of these materials which have been generated.

Various other emission bands are emitted when organic compounds containing heteroatoms are introduced into the hydrogen/air flame (Tilotta et al., 1989). Fluorine and chlorine containing compounds produce characteristic emission spectra of HCl and HF. Silicon and sulfur containing compounds produce emission characteristic of Si-O vibrations and $SO_2$ vibrations. Freon 113 produces a very interesting emission spectrum with HF, HCl, $CO_2$, $H_2O$, and a number of bands attributed to other decomposition products.

The element chlorine is widely distributed in nature and is used extensively in its various oxidation states. Aqueous elemental chlorine ($Cl_2$) and hypochlorite ($OCl^-$), for example, are employed as bleaching agents and as disinfectants to prevent the spread of waterborne diseases. Because of the reactivity of the higher oxidation states of chlorine, the element occurs in nature primarily as the chloride ion ($Cl^-$) and is one of the major inorganic constituents of surface waters, groundwaters, and wastewaters. In seawaters, chloride levels, expressed as chlorinity, are approximately related to salinity and can be used to determine the concentrations of all other bio-unlimited elements present in a sample. Chloride concentration is also used as an indicator of water condition. For example, elevated chloride concentrations in the sewerage of coastal areas may signal seawater intrusion into the system, while in potable water they are often associated with wastewater contamination. In process waters, chloride concentrations are monitored regularly since elevated levels are generally associated with increased deterioration of metallic pipes and structures, while in cooling water, they are used to indicate the cycles of concentration.

Because of the widespread use and occurrence of the many forms of chlorine, analytical methods for their determination are of great importance. A large number of methods exist for the determination of chloride ion and chlorine in aqueous samples. These include chromatographic, spectrometric, potentiometric and titrimetric procedures, with the most widely used methods involving titration of the sample.

For the titrimetric determination of aqueous chloride, various argentometric methods exist which use either indicators or potentiometers to detect the endpoint. Alternatively, mercuric nitrate can be used to titrate chloride ion using diphenylcarbazone as an indicator.

For the determination of chlorine in bleach bath liquors and natural and treated waters in concentrations greater than 1 mg/L, iodometric titration is the method of choice. For chlorine levels less than this amount, amperometric titrations are preferred, but require greater operator skill to avoid loss of chlorine through mechanical stirring. Poor endpoints are also a problem unless the electrodes are properly cleaned and conditioned. Alternatively, N,N-diethyl-p-phenylenediamine (DPD) can be used to determine dissolved chlorine colorimetrically or titrimetrically using ferrous ammonium sulfate.

All of these titrimetric methods suffer severe interference by a variety of species including, bromide, iodide, cyanide, sulfide, and orthophosphate (for chloride) and other oxidizing agents (for chlorine). Because of the problems associated with existing procedures, new analytical methods for the determination of chloride ion and chlorine in aqueous samples could be of great importance in a number of disciplines.

In that the combustion of chlorine-containing compounds in the flame produces HCl, infrared emission detection under high resolution conditions provides spectra wherein the P and R branches of the HCl infrared emission can be easily detected above the flame background in the region from 3200–2400 cm$^{-1}$. Since the HCl emission band lies between the water emission band at 3800–3200 cm$^{-1}$ and the carbon dioxide emission band centered at approximately 2262 cm$^{-1}$, the strong, well-resolved infrared emission from HCl should also be useful analytically for the determination of Cl in a variety of chlorine-containing samples (Kubala et al., 1989b).

Since chlorine gas reacts rapidly with hydrogen under flame conditions to form HCl $$H_2+Cl_2=2HCl$$

any reaction that generates elemental chlorine in a quantitative manner could serve as the basis of an analytical procedure employing flame infrared emission as a highly specific means of detection. As one example, samples containing dissolved chloride ion could be oxidized to elemental chlorine according to the following half-cell ($E°=-1.36$ V), $$2Cl^-=Cl_2(aq)+2e^-$$

using such strong oxidants as permanganate ion ($E°=+1.51$ V in acid solution), peroxide ion ($E°=+1.77$ V in acid solution) or peroxydisulfate ion ($E°=+2.01$ V). The resulting chlorine gas could then be purged from solution using an inert gas and introduced into a hydrogen-air flame to form excited HCl which could be detected by means of its infrared emission.

A second example of an analysis that could be carried out in this manner is the determination of available chlorine in bleaches prepared from elemental chlorine and hypochlorite. In solution these species produce hypochlorous acid ($pK_a=7.60$ at 25° C.) according to the following two equations, respectively, $$Cl_2+2H_2O=HOCl+H_3O^++Cl^-$$

$$OCl^-+H_2O=HOCl+OH^-$$

and the term available chlorine refers to the total oxidizing power of the solution due to chlorine, hypochlorous acid and hypochlorite ion, expressed in terms of an equivalent quantity of $Cl_2$. (The distribution of Cl between these three species is temperature and pH dependent). Since the following equation $$Cl_2+2H_2O=HOCl+H_3O^++Cl^-$$

is readily reversible ($K^{-1}_{eq}=2.2\times10^3$ at 24° C.), addition of acids leads to the rapid generation of dissolved molecular chlorine which can be purged from solution, converted to HCl in the flame, and detected by infrared emission as described previously.

This application reports the development of a new chlorine-specific method for the direct determination of chloride and available chlorine in aqueous samples based on the principle of infrared emission. The flame infrared emission-chlorine analyzer described in Example 4 consists of two commercially available purge devices coupled to a flame infrared emission detector. Aqueous chlorine-containing samples are treated chemically to convert the chloride or hypochlorous acid present into molecular chlorine ($Cl_2$) which is then liberated from the sample cell using an inert carrier gas and introduced into a hydrogen/entrained-air flame to produce vibrationally excited HCl.

A substantial improvement in detection capabilities results when a dual beam system is used as the detector of a flame infrared emission detection method. The dual beam system allows subtraction of the background and most importantly the fluctuations in the background (i.e. the noise). The signal-to-noise ratio is improved substantially with the use of the improved dual beam system. The selectivity ratio and detection limits can be optimized by varying the detector bias voltage, by use of a 3.0 μm filter for background compensation, an optical attenuation method to balance the bridge network, and a variable bridge resistor.

Many biochemical reactions release carbon dioxide as a by-product of the reaction (for example, fermentation of sugar by yeast). Infrared emission is therefore useful for a variety of clinical and biochemical assays involving carbon dioxide, such as the clinical determination of carbon dioxide in blood and respiratory gases.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

The following experimental embodiments are illustrative.

EXAMPLE 1

An Improved Burner Design for a Flame Infrared Emission Gas Chromatography Detector Flame infrared emission measurements made with the use of a new capillary burner described herein have shown that FIRE-GC sensitivity has been improved by approximately one to 1.5 orders of magnitude, primarily as a result of changes in burner design (Zhang et al., 1992b). The new burner consists of two stainless steel tubes of different diameters, mounted concentrically. Air is introduced through the outer tube, while a mixture of GC effluent and hydrogen gas is introduced through the inner capillary tube. Pre-mixing the analyte with hydrogen promotes uniform, complete combustion and reduces mixing and condensation of analytes in the transport line between the GC column and burner.

In comparison with the burner described in the parent application Ser. No. 07/415,141, the new burner design requires considerably less hydrogen to produce a stable flame. Consequently, flame water background emission is greatly reduced, and background subtraction is no longer required. Since a beam splitter and other components associated with the background subtraction procedure are no longer necessary, the instrumental complexity of the FIRE radiometer is considerably simplified, and more of the signal can be used for analyte detection.

By suitable adjustment of the hydrogen and air flow rates, the flame supported by this new burner can be made to produce a zone of maximum emission intensity which appears to be concentrated in a smaller volume of space and located directly along the central axis of the burner. If this zone of maximum emission intensity is raised approximately 3 mm above the burner tip, the burner remains relatively cool, and background radiation from blackbody emission is also reduced. Optimization parameters for the hydrogen and air flow rates appear to be the same for all compounds, GC columns (packed and capillary), and injection volumes (0.1 to 2.0 µL) tested.

Sensitivity of the new FIRE-GC detector is such that it can be used in conjunction with the smaller injection volumes required by capillary columns, thus permitting improved separation of more complex mixtures. The utility of the new FIRE-GC detector was demonstrated by an application involving the separation of a synthetic mixture of 16 compounds on a 15-m silica capillary column under programmed temperature conditions. The new burner was shown to respond well to all components of the mixture, including halogenated, non-halogenated, and aromatic compounds, and was also able to detect impurities present in two of the components. The nearly perfect peak shapes present in the chromatograms demonstrated the ability of the FIRE-GC detector to respond to compounds with a range of boiling points (36°–152° C.).

A conservative estimate of detection limits (2σ) indicates that the new FIRE-GC detector can respond to 8.6 ng $s^{-1}$ of benzene, 9.4 ng $s^{-1}$ of butanone, 4.6 ng $s^{-1}$ of 1-chloro-3-methylbutane, and 5.6 ng $s^{-1}$ of methyl acetate. This represents an average detection limit of 4.5±1.3 ng $s^{-1}$ in terms of carbon. Response, in terms of µmoles of carbon, was linear over the entire range of concentrations tested, giving an estimated LDR of at least 3.4 orders of magnitude.

These detection limits determined for the new FIRE-GC detector are approximately 2–3 orders of magnitude above those of the flame ionization detector.

EXPERIMENTAL

Instrumental Configuration.

FIG. 1 shows a schematic diagram of the analytical system used in this study. Radiation from the burner was modulated at 569 Hz with the use of a laboratory-constructed chopper, and a lock-in amplifier (Model #3962, Ithaco, Inc., Ithaca, N.Y.) was used to demodulate the chopped signals obtained from the detectors. The output signal from the lock-in amplifier was recorded on a recorder/integrator (Model #3394A, Hewlett-Packard Corp., North Hollywood, Calif.).

FIRE Radiometer.

The multichannel FIRE radiometer used in this example employed a direct-reading polychromator (Kubala, et al., 1991) having a spectral bandwidth of 0.15 µm and equipped with three PbSe detectors. The polychromator, originally designed (Kubala, et al., 1991) to monitor emission corresponding to $H_2O$ (2.8 µm), HCl (3.8 µm), and $CO_2$ (4.4 µm), employed a long-pass filter with a cut-on wavelength of 3.0 µm for order sorting and attenuation of the water emission at 2.8 µm. During most of the burner evaluation studies, all three channels were monitored in the unsubtracted mode. It should be noted, in particular, that, during the GC application involving separation of a 16-component mixture, the polychromator was operated in the single-channel, unsubtracted mode, and only the 4.4 µm ($CO_2$) detector was utilized. Calcium fluoride collection optics, described previously (Kubala, et al., 1991), were used to focus an image of the source onto the entrance slit of the polychromator.

Gas Chromatograph.

A gas chromatograph (GC-8A, Shimadzu Scientific Instruments, Inc., Colombus, Md.) with temperature programming capability was used for all chromatographic applications. Analytes were introduced into the chromatograph with conventional microsyringes obtained from standard commercial sources. Injection volumes varied from 0.1 to 2.0 µL.

Separations were performed with a 15-m×0.53-mm SPB-20 silica capillary column (Supelco, Inc., Bellafonte, Pa.) or a 182-cm× 3.175-mm (6-ft.×⅛-in.) stainless steel column packed with 10% Carbowax on 80/100 mesh Chromosorb W HP (Supelco, Inc.). In the case of the packed column, optimization measurements were made with a column temperature of 100° C. and a carrier gas (helium) flow rate of 15 ml $min^{-1}$. In the case of the capillary column, optimization measurements were made with a column temperature of 60° C. and a carrier gas (helium) linear velocity of 12.5 m $min^{-1}$. The flow rate for the capillary column was determined by measuring the retention time for $CO_2$ gas. Separation of the 16-component synthetic mixture was performed with the capillary column, starting at an initial temperature of 40° C. and programmed to rise at a rate of 10° C. min$^{-1}$.

Integrated peak areas, rather than peak heights, were used as a measure of the emission intensity. Each data point was obtained by making at least two injections.

Capillary Burner.

FIGS. 2A and 2B show a schematic diagram of the new burner employed in this example and represents the results of a number of design modifications. The burner consists of two metal tubes of different diameters, 202 and 204 mounted concentrically. The outer tube 204 was constructed of 4.76-mm (3/16-in.), stainless steel tubing, which was mounted inside a 1.5×1.5×1.5-in. aluminum block 208 using a ¼-in. NPT to Swagelock connector and held in place by a ¼ in. to 3/16-in. reducing ferrule. The inner tube 202 was constructed of 0.76-mm. (0.03-in.)-diameter stainless steel capillary tubing and was positioned inside the outer tube by a glass wool plug 200 (FIG. 2B). Extension of the inner capillary tube about 1 mm above the outer tube at the burner tip was found to be beneficial in reducing background radiation and improving flame stability.

The GC column was interfaced directly to the central capillary of the burner through a short segment of stainless steel tubing [1.59 mm (1/16-in.) o.d., 0.51 mm (0.020-in.) i.d.]. As a means of preventing analyte condensation, the stainless steel transfer tube was wrapped with heating tape (Part #N-03122-30, Cole Palmer Instrument Co., Chicago, Ill.), and the desired temperature (about 20° to 50° C. higher than the boiling point of the least volatile compound being chromatographed) was maintained by power from a laboratory variac. GC effluents were premixed with hydrogen gas shortly after exiting the chromatograph. The hydrogen flow rate was controlled by a mass-flow controller (Catalog #2-2834M, Supelco, Inc.), which maintained a constant flow rate within ±0.3%.

Air was introduced into the outer tube of the burner through ⅛-in. copper tubing which was welded into the side of a laboratory constructed T-connector. The top of this T-connector was attached to the outer stainless steel tube of the burner with a ¼-in.×3/16-in. reducing ferrule, and the bottom of the T-connector was attached to a 1/16-in. Swagelock fitting and graphite ferrule, which served to connect the inner stainless steel capillary tube to the transfer tube from the gas chromatograph. The total distance between the top of the T-connector and the bottom of the burner was approximately two inches. The air flow rate was controlled by a standard gas rotameter (Part #3227-26, Cole-Palmer Co.).

The burner position (FIG. 1) was located at the focus of the input collection optical system, and the vertical height was adjusted to a position that gave the best compromise between analyte emission band radiance and source background. The optimum vertical position for the tip of the burner was employed during chromatographic analysis of the 16-component mixture.

Reagents.

All chemicals were obtained from common commercial sources and used without further purification. Optimization studies were performed with two synthetic mixtures, one consisting of benzene, butanone, 1-chloro-3-methylbutane, and methyl acetate, which was prepared by weighing and dilution with pentans, and a second consisting of a 4% solution of tetrahydrofuran (THF) in hexane, which was prepared in a similar manner. A 16-component mixture, containing compounds having a variety of functional groups, was also prepared by weighing and used to demonstrate the performance of the FIRE-GC detector during separation of a more complex sample.

RESULTS AND DISCUSSION

Capillary Burner Design.

A delivery system consisting of two concentrically mounted tubes was designed in which hydrogen gas was premixed with carrier gas and analyte in a central capillary tube 202, while air was introduced through an outer tube 204 (FIGS. 2A and 2B). This design produced a diffusion flame and ensured that combustion could begin only after the analyte and hydrogen had been able to mix with the oxidant above the burner tip. Premixing the analyte with hydrogen had the additional benefit of increasing the linear velocity of gases in the transport line. An increase in linear velocity reduced axial diffusion of the eluting analytes (thereby reducing peak broadening), and reduced the partial pressure of the analyte vapor (thereby decreasing the tendency for the analytes to condense during transport to the burner).

The diffusion flame produced by the concentric, two-tube design appeared to have better stability and much lower noise levels than had been observed with the multiport capillary tube design. With a hydrogen flow rate of at least 20 mL min$^{-1}$ being maintained, the diffusion flame could be kept fuel rich and produced a zone of maximum temperature about 3 mm above the burner tip. With the use of this burner design, the burner tip remained relatively cool (about 100° C.), thereby decreasing the amount of background contributed by blackbody radiation.

Because the flame produced by the concentric, two-tube design is always surrounded by a layer of air issuing from the outer tube, the emission signal proved to be much less sensitive to changes in ambient $CO_2$ levels than with other burner designs. The flame also appears to center the maximum in $CO_2$ emission intensity in a smaller volume of space along the central axis of the burner. This emission profile can be contrasted with that of the diffusion flame produced by the old multiport capillary burner (Hudson and Busch, 1987), in which the emission intensity is more spread out and tends to be concentrated off the central axis of the burner (Ravishankar et al., 1991). A major reason for this difference is that premixing the hydrogen and analyte allows the combustion of both to begin almost simultaneously, thereby requiring less diffusion (spreading) of the flame gases before significant quantities of $CO_2$ are produced. Moreover, the concentric, two-tube design also requires a much lower hydrogen flow rate (20 mL min$^{-1}$ compared with 300 mL min$^{-1}$ for the multiport capillary) to achieve a stable flame, thereby also helping to reduce the size of the flame.

Other minor modifications to the basic concentric, two-tube design were found to be beneficial in increasing the signal-to-noise ratio (SNR) of the $CO_2$ emission signal and can be briefly listed as follows: (1) The glass wool plug 200 (FIG. 2B) was useful, not only for positioning the central capillary, but also for removing much of the turbulence in the air flow caused by the right-angle connection (FIG. 2A). Smoothing the air flow produced a more stable flame with less fluctuation noise. (2) The 1.5×1.5×1.5-in. aluminum block 208 not only aided in aligning the burner (FIG. 1) but also helped to conduct heat away from the FOV of the detector and reduce background resulting from blackbody radiation. (3) Extending the inner capillary tubing about 1 mm above the outer air-delivery tube at the burner tip promoted combustion well above the burner tip and reduced the temperature of the top of the burner from about 500° C. to approximately 100° C. The resulting air flow produced by this design modification also significantly reduced the quantity of water vapor which condensed around the outer capillary at the burner tip. Since these water droplets tended to re-evaporate at irregular intervals, causing fluctuations in flame temperature and background emission levels, preventing the formation of this condensate improved flame stability and reduced flame noise. (4) Finally, as the flame became more stable, the FIRE radiometer became so sensitive to changes in ambient $CO_2$ levels that it began to respond to the breath of the instrument operator. A chimney was added to further reduce noise from variations in ambient $CO_2$ levels and to reduce stray light levels. This housing covered the entire flame, the first light collection lens, and the back reflection mirror (FIG. 1).

Effect of Air Flow Rate on Emission Intensity.

In optimizing the FIRE-GC detector using the new burner design, air flow rate proved to be not particularly critical, and a range from about 100 to 200 mL min$^{-1}$ was satisfactory. Below 100 mL min$^{-1}$, condensation of water around the burner tip was observed, causing the flame to become unstable Above 200 mL min$^{-1}$, the combustion rate increased to the point where heating of the capillary tube resulted in unacceptable levels of background radiation. A similar problem was encountered when air was switched to oxygen. The use of pure oxygen lowered the zone of maximum temperature in the flame to a position closer to the burner tip. Even by compensating with a faster hydrogen flow rate, unacceptable heating of the burner resulted.

Effect of Hydrogen Flow Rate on Emission Intensity.

Figure 3:
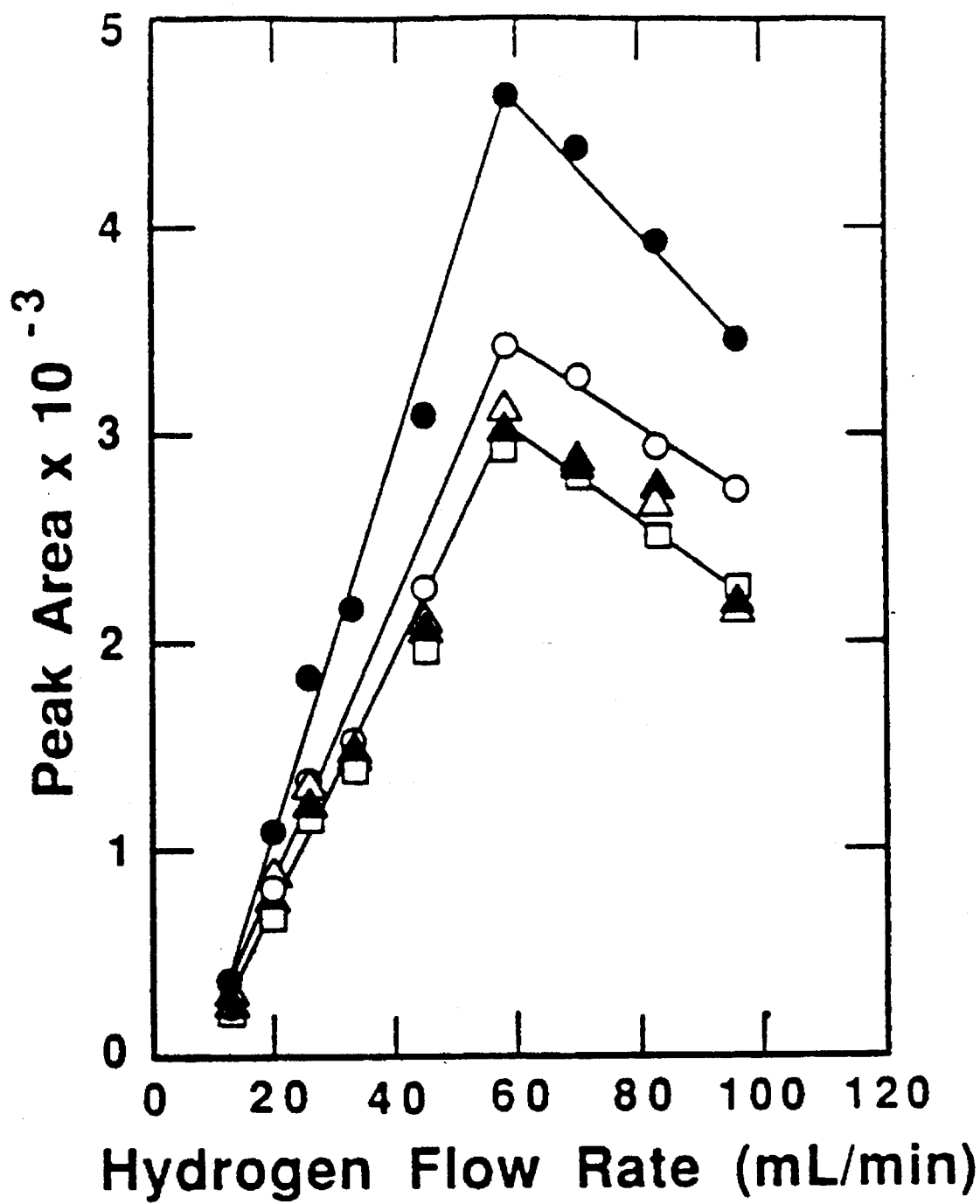
FIG. 3 shows the integrated emission intensity (chromatographic peak area, arbitrary units) at 4.4 µm as a function of hydrogen flow rate for 0.2-µL injections of a mixture containing 29.4 µg of benzene (●), 40.2 µg of butanone (□), 32.6 µg of 1-chloro-3-methylbutane (o), and 23.4 µg of methyl acetate (▲) in pentane (Δ), chromatographed at an oven temperature of 60° C. on a 15-m×0.53-mm SPB-20 silica capillary column. Air, 100 mL min$^{-1}$; He carrier gas, 12.5 m min$^{-1}$; observation height, 3 mm; no background subtraction employed. Observation height refers to the vertical distance between the optical axis of the light collection lens and the tip of the central capillary tube at the top of the burner.

Hydrogen flow rate proved to be highly critical for FIRE-GC optimization. FIG. 3 shows a plot of the peak areas obtained in the 4.4-μm ($CO_2$) channel as a function of hydrogen flow rate for 0.2-μL injections of a mixture of five compounds, each having a different functional group, onto the 15-m silica capillary column. Air flow rate was 100 mL min$^{-1}$ in all cases, observation height was 3 mm above the top of the inner capillary, and no background subtraction was employed. As can be seen from FIG. 3, the signal in the $CO_2$ channel optimized at 60 mL min$^{-1}$ of hydrogen for each of the five compounds. However, background emission in this channel also increased more or less monotonically with hydrogen flow rate (FIG. 4), and 40–60 mL min$^{-1}$ of hydrogen appeared to represent a good operating range whenever the silica capillary column was employed.

Figure 5:
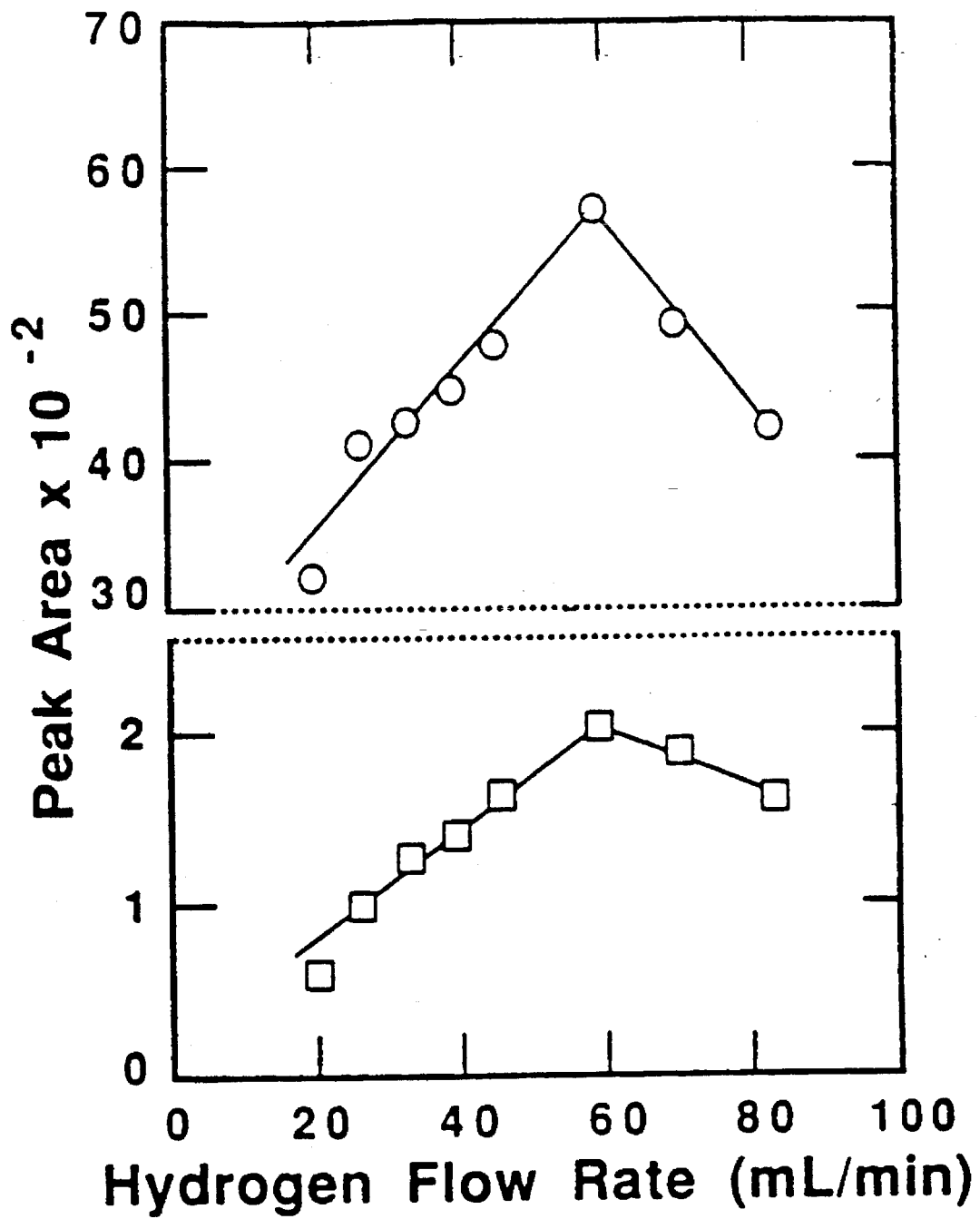
FIG. 5 shows the integrated emission intensity (chromatographic peak area, arbitrary units) at 4.4 µm as a function of hydrogen flow rate for 0.2-µL injections of a mixture of 4% tetrahydrofuran (□) in hexane (o), chromatographed at an oven temperature of 100° C. on a 182-cm×3.175-mm (6-ft× 1/8-in.) stainless steel column packed with 10% Carbowax on 80/100 mesh Chromosorb W HP. Air, 100 mL min$^{-1}$; He carrier gas, 15 mL min$^{-1}$; observation height, 3 mm; no background subtraction employed.

FIG. 5 shows a plot of the peak areas obtained in the 4.4-μm ($CO_2$) channel as a function of hydrogen flow rate for 0.2-μL injections of a mixture of 4% THF in hexane onto the 6-ft packed column. Air flow rate was 100 mL min$^{-1}$ in all cases, observation height was 3 mm above the top of the inner capillary, and no background subtraction was employed. Again, the signal in the $CO_2$ channel optimized at 60 mL min$^{-1}$ of hydrogen for both THF and hexane, but because the background emission in this channel also increased monotonically with hydrogen flow rate (FIG. 6), 40–60 mL min$^{-1}$ of hydrogen appeared to represent a good operating range whenever the packed column was employed.

Figure 6:
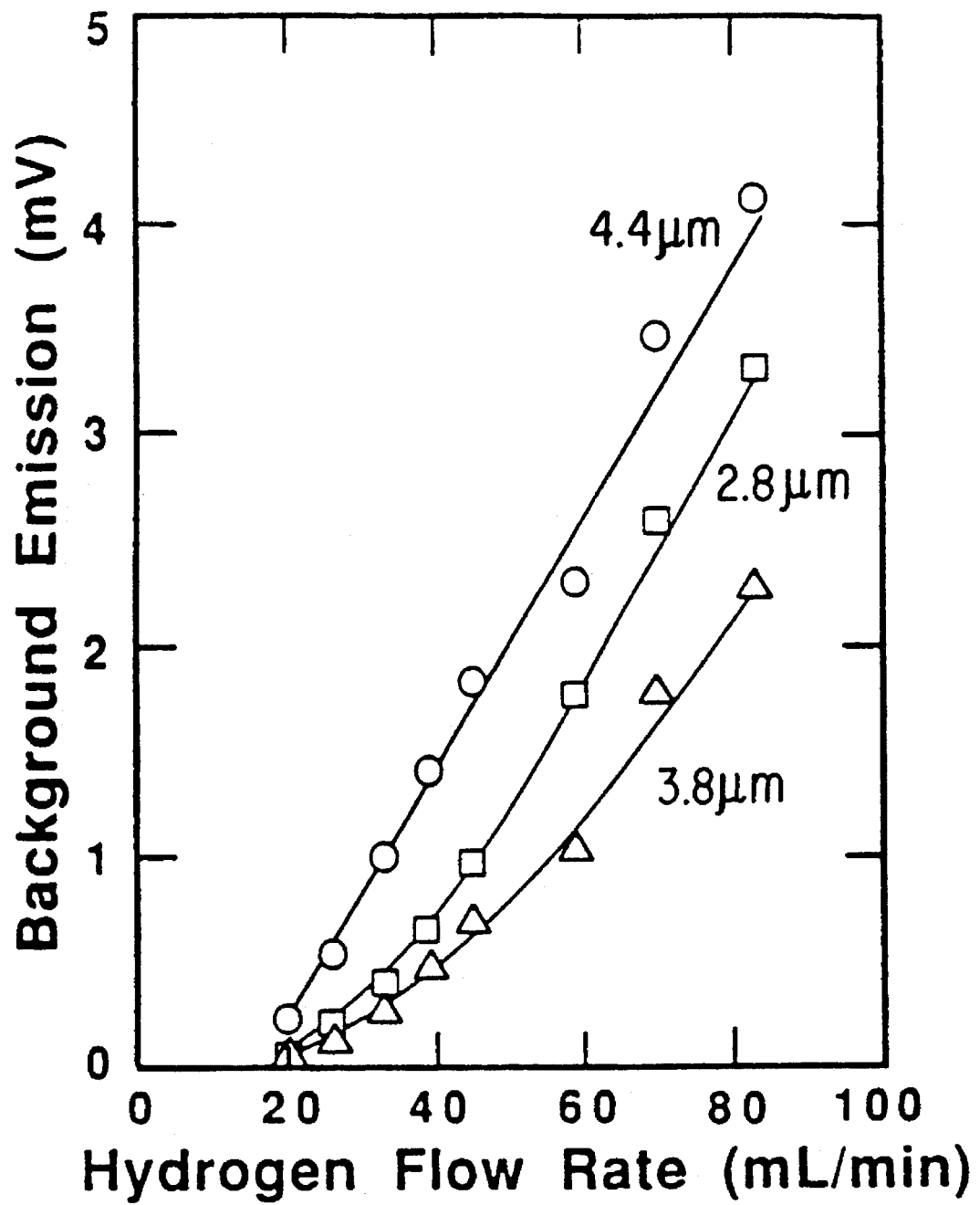
FIG. 6 shows the background emission intensity (mV) in the 4.4 µm (o), 3.8 µm (Δ), and 2.8 µm (□) channels as a function of hydrogen flow rate for the concentric, two-tube burner when used in conjunction with the 182 cm×3.175-mm (6-ft×1/8-in.) stainless steel column packed with 10% Carbowax on 80/100 mesh Chromosorb W HP. Other operating conditions identical to those of FIG. 5.

As shown by FIGS. 4 and 6, background emission remained quite low for either type of column at almost all hydrogen flow rates. The monotonic increase in background emission with hydrogen flow rate strongly suggests that most of this emission results from gas-phase species associated with water, formed as a result of the combustion of the flame gases themselves. The presence of water background emission is also suggested by the relative intensities observed in the 4.4-, 3.8-, and 2.8-μm channels (FIGS. 4 and 6). The least intense water bands have been shown to occur in the 3.8 μm region (Ravishankar et al., 1990), and this channel was observed to have the lowest background signal at almost all hydrogen flow rates. (The actual relative intensity at 3.8-μm, compared with the intensities observed in the other two channels, may be even less (Busch and Busch, 1991) than indicated by FIGS. 4 and 6 because the 3.8-μm detector had an area which was four times larger than that of either of the other two detectors (Kubala, et al., 1991). The most intense water emission bands have been observed in the 2.8-μm region (Ravishankar, et al., 1990). Since the 2.8-μm signals shown in FIGS. 4 and 6 were attenuated by the polychromator (Kubala, et al., 1991) by approximately one order of magnitude, the emission intensity at 2.8-μm produced the most intense background emission at all hydrogen flow rates.

Effect of Observation Height.

Figure 7:
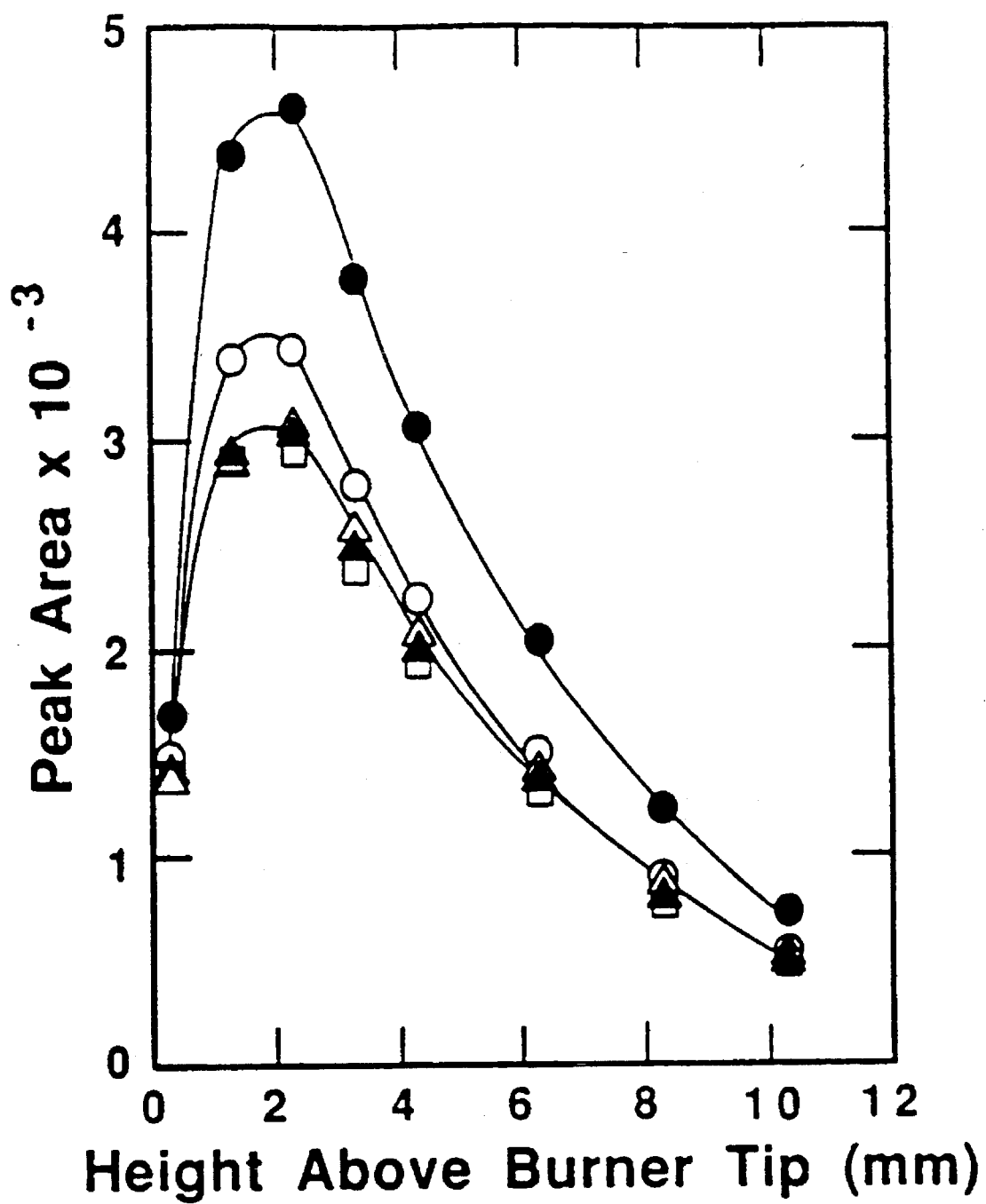
FIG. 7 shows the integrated emission intensity (chromatographic peak area, arbitrary units) at 4.4 µm as a function of observation height for a 0.2-µL injection of a mixture consisting of 29.4 µg of benzene (●), 40.2 µg of butanone (□), 32.6 µg of 1-chloro-3-methylbutane (o), and 23.4 µg of methyl acetate (▲) in pentane (Δ), chromatographed at a temperature of 60° C. on a 15-m×0.53-mm SPB-20 silica capillary column. Air, 100 mL min$^{-1}$; hydrogen, 58 mL min$^{-1}$; He carrier gas, 12.5 m min$^{-1}$.

The height at which the emission signal was monitored proved to be another critical parameter for FIRE-GC optimization. FIG. 7 shows a plot of peak areas obtained in the 4.4-μm ($CO_2$) channel as a function of observation height for 0.2-μL injections of a mixture of five compounds onto the 15-m silica capillary column. In this figure, observation height refers to the vertical distance between the optical axis of the light collection lens and the tip of the central capillary tube at the top of the burner. Hydrogen flow rate and air flow rate were 58 and 100 mL min$^{-1}$, respectively, and no background subtraction was employed. As can be seen from FIG. 7, the signal in the $CO_2$ channel optimized at approximately 2–3 mm for each of the five compounds.

Figure 8:
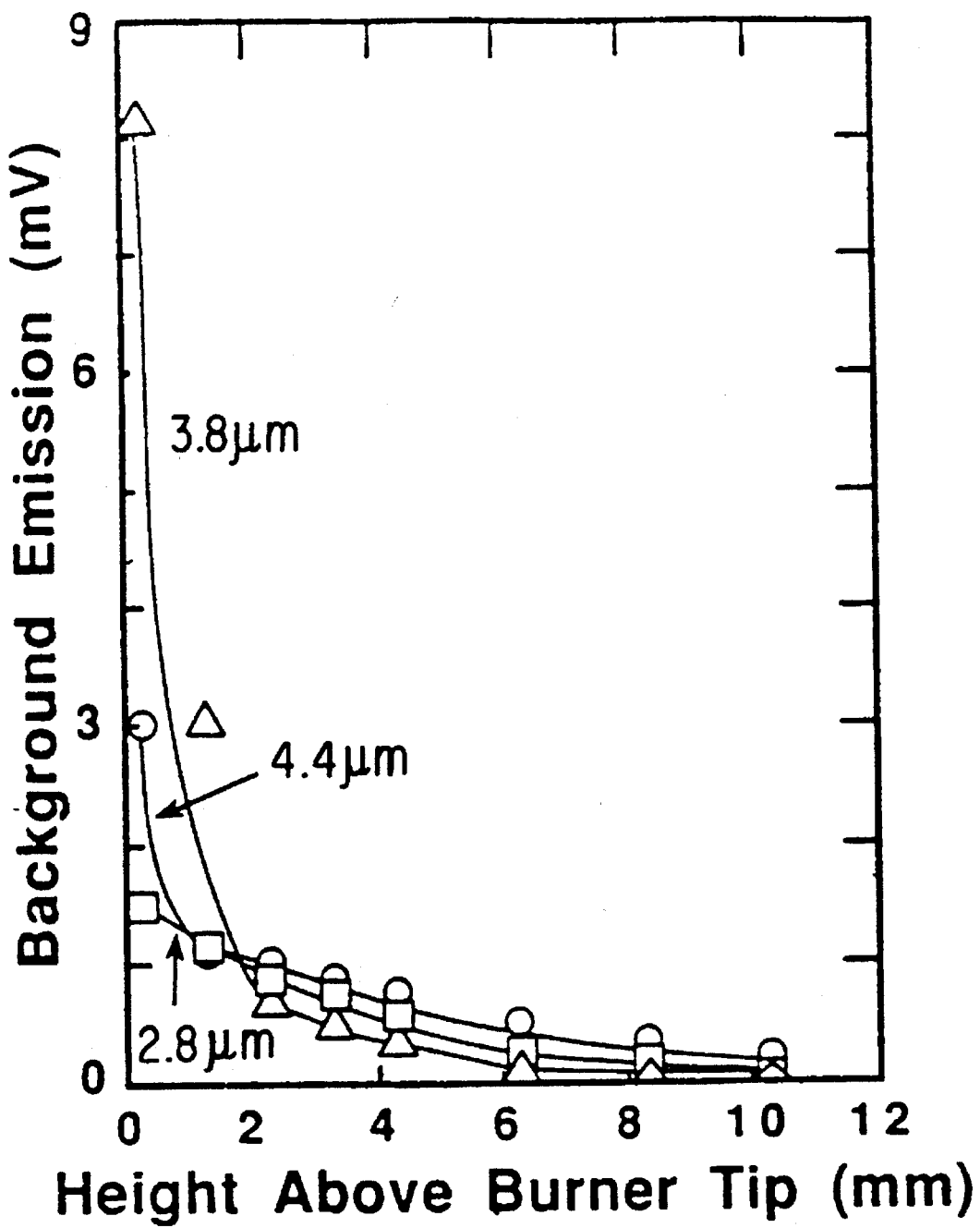
FIG. 8 shows the background emission intensity (mV) in the 4.4-µm (o), 3.8-µm (Δ), and 2.8-µm (□) channels as a function of observation height for the concentric, two-tube burner when used in conjunction with the 15-m×0.53-mm SPB-20 silica capillary column. Other operating conditions identical to those of FIG. 7.

As shown in FIG. 8, background emission in each of the three channels was also a function of observation height. Above 2 mm, background radiation was low and remained relatively unaffected by changes in observation height. Below 2 mm, background radiation increased exponentially as observation height decreased. This rise in background signal can be attributed to the increasing amount of blackbody radiation which comes into the FOV of the detector as the optical axis of the light collection system approaches the capillary tubing and aluminum block.

Linear Dynamic Range.

Figure 9:
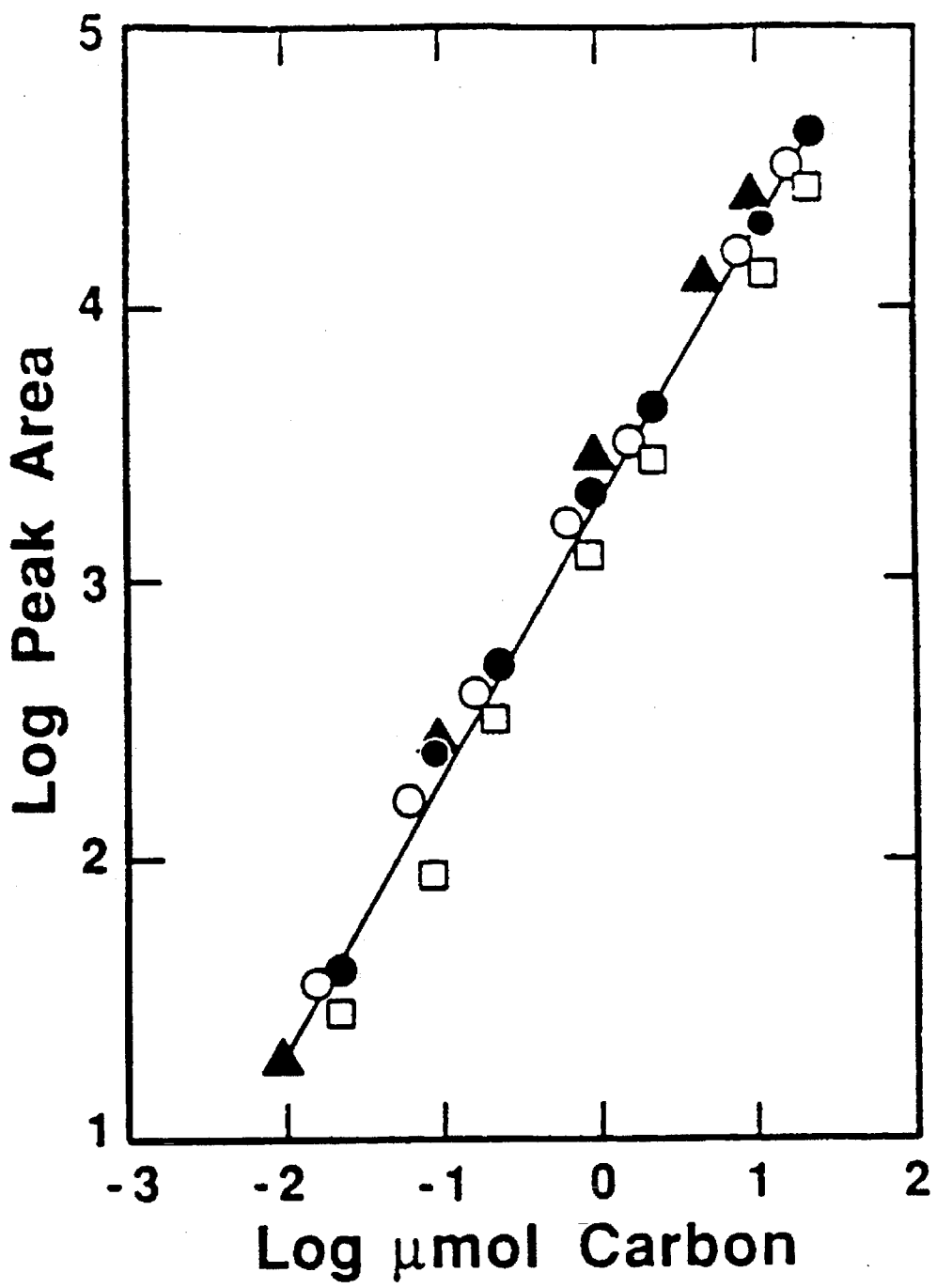
FIG. 9 shows the logarithm of the average integrated emission intensity (chromatographic peak area) at 4.4 µm as a function of the logarithm of the µmoles of carbon for a test mixture of benzene (●), butanone (□), 1-chloro-3-methylbutane (o), and methyl acetate (▲) in pentane, obtained with the use of the new, concentric, two-tube burner. Conditions: 15-m×0.53-mm SPB-20 silica capillary column; oven temperature, 60° C.; air, 100 mL min$^{-1}$; hydrogen, 58 mL min$^{-1}$; He carrier gas, 12.5 m min$^{-1}$; observation height, 3 mm; no background subtraction employed.

The same 5-component mixture used for optimization studies was also used to study the LDR of the FIRE-GC detector when the new burner was employed in conjunction with the silica capillary column. Assuming that each compound is converted to terminal combustion products, the emission intensity in the 4.4-μm ($CO_2$) channel should be proportional to the number of moles of carbon present in the analyte. FIG. 9 shows a log-log plot of the 4.4-μm emission intensity vs. the μmoles of carbon for each of the four test compounds. The points representing the two lowest sample concentrations required dilution of the original mixture with pentane, so pentane does not appear in the plot.

As shown in FIG. 9, the plot appears to be reasonably linear over the entire range of concentrations (μmol C) studied, indicating that the LDR is at least 3.4 orders of magnitude and possibly larger. The slope of the least-squares lines through all points was 0.992 (linear regression coefficient, 0.998), indicating uniformly high conversion of all four compounds to $CO_2$.

Detection Limits.

Detection limits, defined as that quantity of analyte required to give an emission signal which was two times the standard deviation of the baseline noise (2σ), were calculated for the FIRE radiometer acting as a mass-flow-rate detector (units of ng s$^{-1}$) (Hudson and Busch, 1987), assuming a Gaussian peak shape. The assumption of symmetrical peak shape is approximately valid for the small sample size used in these measurements.

The detection limits estimated for the four compounds shown in FIG. 9 are given in Table 1.

TABLE 1

Detection limit data for selected compounds.
$2\sigma_{baseline} = 2.4$ μV

| Compound | $g^a$ (ng) | $S_{max}^b$ (μV) | A/h$^c$ (s) | $(\Phi_p)_{dl}^d$ (ng s$^{-1}$) | $(\Phi_p)_{dl}^d$ (ng C s$^{-1}$) |
|---|---|---|---|---|---|
| Benzene | 294 | 48.7 | 3.1 | 4.6 | 4.2 |
| Butanone | 402 | 36.6 | 2.8 | 9.4 | 6.3 |
| 1-Chloro-3-methyl-butane | 326 | 24.9 | 4.6 | 5.6 | 3.2 |
| Methyl acetate | 234 | 31.0 | 2.1 | 8.6 | 4.2 |

$^a$g is the number of grams of solute injected
$^b$S$_{max}$ is the signal at the peak maximum
$^c$A is the area under the peak and h is the height of the peak
$^d$$(\Phi_p)_{dl}$ is the mass-flow rate detection limit It should be recognized that these values are somewhat dependent on the time constant chosen for the lock-in amplifier (set at 300 ms) and the peak width parameter chosen for the integrator (set at 0.04 min to minimize peak distortion). Given the instrument settings used for these measurements, it is believed that the values reported in Table 1 are somewhat conservative but provide a reasonable indication of the improvement in detection limits achieved by this new burner design.

Chromatographic Application.

Figure 10A:
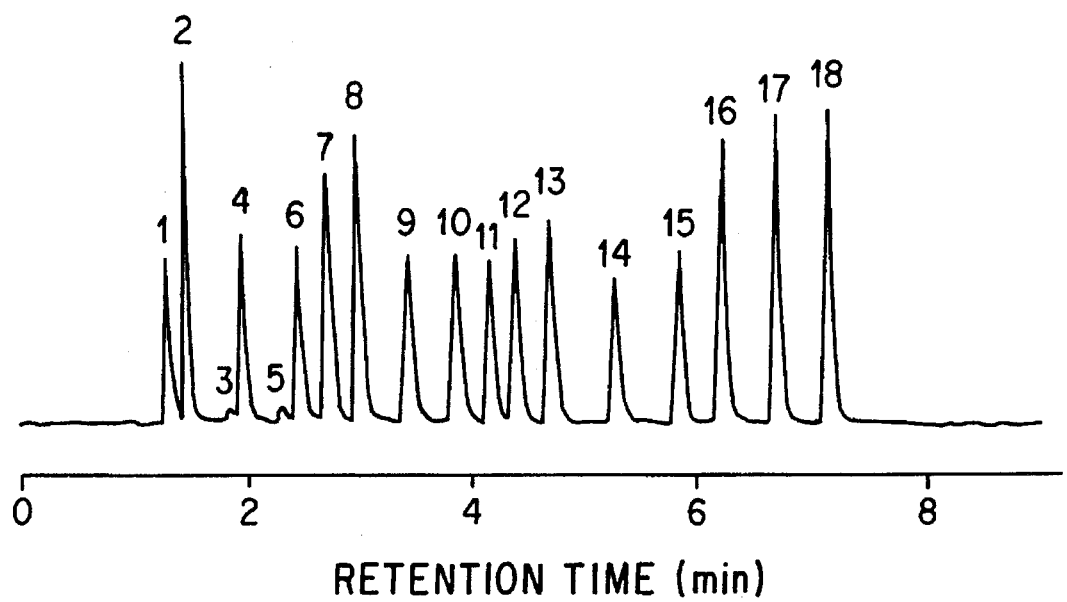
FIGS. 10A, 10B and 10C show the chromatograms for synthetic mixtures obtained using (10A) a 15-m×0.53-mm SPB-20 silica capillary column in conjunction with the new, concentric, two-tube burner design, 4.4-µm detector, unsubtracted mode; (10B) a Carbopack-B™ (5% Fluorcol™) packed column in conjunction with the old multiport capillary burner, 4.4-µm detector, subtracted mode; and (10C) a Carbopack-B™ (5% Fluorcol™) packed column in conjunction with the old multiport capillary burner, 4.4-µm detector, unsubtracted mode. Components in order of elution for chromatogram 10A: (1) methanol (5.26 µg); (2) n-pentane (4.00 µg); (3) pentane isomer (impurity); (4) n-hexane (3.81 µg); (5) hexane isomer (impurity); (6) ethyl acetate (5.19 µg); (7) cyclohexane (4.96 µg); (8) benzene (4.77 µg); (9) methyl cyclohexane (4.22 µg); (10) 4-methylheptane (4.64 µg); (11) 1-chloropentane (5.04 µg); (12) octane (4.37 µg); (13) cycloheptane (5.04 µg); (14) butyl acetate (5.17 µg); (15) 1-chlorohexane (5.54 µg); (16) m-xylene (5.61 µg); (17) o-xylene (6.21 µg); and (18) cumene (6.55 µg). Conditions: 0.1-µL injection volume; He carrier gas, 12.5 m min$^{-1}$; linear temperature program from 40° to 80° C. at 10° C. min$^{-1}$. Components in order of elution for chromatograms 10B and 10C: (1) dichloromethane (309 µg); (2) trichlorofluoromethane (300 µg); (3) trichloromethane (330 µg): (4) trichlorofluoroethane (123 µg); (5) tetrachloromethane (300 µg); (6) hexane (33 µg); and (7) heptane (23 µg). Conditions: 1.0-µL injection volumes; He carrier gas, 30 mL min$^{-1}$; linear temperature program from 160° to 220° C. at 16° C. min$^{-1}$. (Chromatograms 10B and 10C are from S. Ravishankar, et al., 1990).

As a demonstration of the utility of the FIRE-GC detector, a synthetic mixture of 16 compounds, having a variety of functional groups and structural types, was chromatographed on the 15-m silica capillary column under programmed temperature conditions (40° to 120° C. at 10° C. min$^{-1}$). FIG. 10A shows the FIRE chromatogram obtained for a 0.1-μL injection of this mixture, with the use of the 4.4-μm ($CO_2$) channel in the unsubtracted mode.

It is clear from FIG. 10A that the new burner responds well to all 16 components and, therefore, performs well for a number of compound types, including simple straight-chain and branched-chain hydrocarbons, cyclic hydrocarbons, halogenated hydrocarbons, substituted and unsubstituted aromatics, esters, and alcohols. The minor peaks (3 and 5 in FIG. 10A) are believed to be an isomer impurity in the reagent grade n-pentane and n-hexane, as suggested by the chromatograms obtained when n-pentane and n-hexane were each injected separately. These two small peaks demonstrate the ability of the FIRE-GC detector to respond to small amounts of impurities present in a sample. The nearly perfect shapes of the last three peaks also demonstrate the ability of the new burner system to handle compounds with relatively high boiling points (m-xylene, 139.1° C., o-xylene, 144.4° C.; cumene, 152.2° C.) (Handbook of Chemistry and Physics, 1991a) as well as compounds with relatively low boiling points (methanol, 64° C., n-pentane, 36.1° C.; and n-hexane, 69° C.) (Handbook of Chemistry and Physics, 1991b). Detection limits estimated from the chromatogram in FIG. 10A are given in Table 2.

TABLE 2

Detection limit data for 16-component mixture, $2\sigma_{baseline} = 0.23$ mm.

| Compound | $g^a$ (μg) | h$^c$ (mm) | A/h$^c$ (s) | $(\Phi_p)_{dl}^d$ (ng s$^{-1}$) | $(\Phi_p)_{dl}^d$ (ng C s$^{-1}$) |
|---|---|---|---|---|---|
| Methanol | 5.26 | 30 | 3.8 | 10 | 3.9 |
| Pentane | 4.00 | 62 | 2.8 | 5.2 | 4.3 |
| Hexane | 3.81 | 34 | 4.3 | 5.9 | 4.9 |
| Ethyl Acetate | 5.19 | 32 | 4.6 | 8.0 | 4.4 |
| Cyclohexane | 4.96 | 44 | 5.0 | 5.0 | 4.4 |
| Benzene | 4.77 | 52 | 4.5 | 4.6 | 4.2 |
| Methylcyclohexane | 4.22 | 30 | 5.8 | 5.5 | 4.7 |
| 4-Methylheptane | 4.64 | 30 | 5.9 | 5.9 | 5.0 |
| 1-Chloropentane | 5.04 | 30 | 4.4 | 8.6 | 4.8 |
| Octane | 4.37 | 33 | 5.2 | 5.8 | 4.9 |
| Cycloheptane | 5.04 | 36 | 5.5 | 5.7 | 4.9 |
| Butyl Acetate | 5.17 | 26 | 4.9 | 9.2 | 5.7 |
| 1-Chlorohexane | 5.54 | 32 | 4.7 | 8.3 | 4.9 |
| m-Xylene | 5.61 | 51 | 4.4 | 5.7 | 5.1 |
| O-Xylene | 6.21 | 56 | 4.3 | 5.9 | 5.3 |
| Cumene | 6.55 | 57 | 4.4 | 5.9 | 5.3 |

$^{a,c,d}$See Table 1.

Figure 10B:
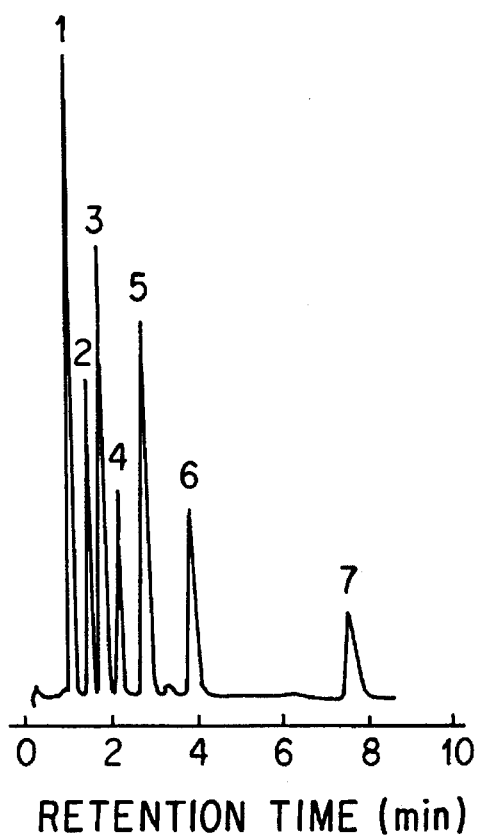
Figure 10C:
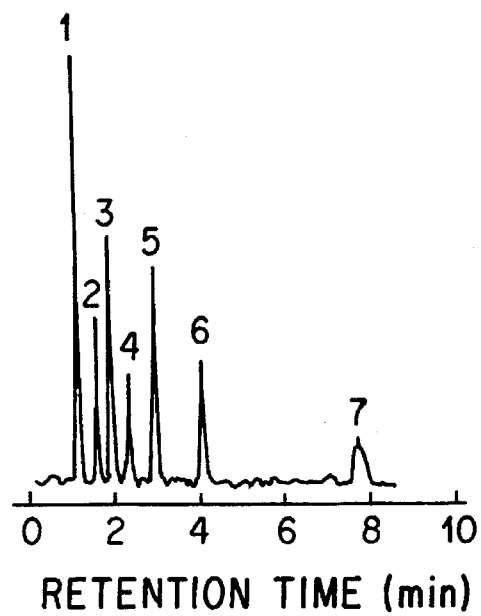

For comparison, FIGS. 10B and 10C show FIRE chromatograms obtained with the old multiport capillary burner and represent results obtained for a 1-μL injection of a 7-component mixture onto a packed column, with the 4.4-μm ($CO_2$) channel operating in the subtracted (FIG. 10B) and unsubtracted (FIG. 10C) modes. The improvement in FIRE-GC sensitivity resulting from the new burner is best demonstrated with n-hexane as an example. Comparing peak 4 in FIG. 10A (3.81 g n-hexane) with peak 6 in FIGS. 10B and 10C (33 μg n-hexane) shows that the sensitivity of the FIRE-GC detector has been improved by approximately one order of magnitude in comparison with the old FIRE-GC detector operating in the subtracted mode and by approximately 1.5 orders of magnitude in comparison with the old FIRE-GC detector operating in the unsubtracted mode.

EXAMPLE 2

The current embodiment for a FIRE radiometer is described in the present example. This new prototype instrument incorporates refinements such as an improved burner, an improved optical system and a preamplifier circuit that increase the sensitivity of the instrument compared with that described in parent application Ser. No. 07/415,141. The burner is shielded from the environment to reduce sources of drift such as drafts or exhaled carbon dioxide from persons standing in the vicinity of the instrument.

Figure 11:
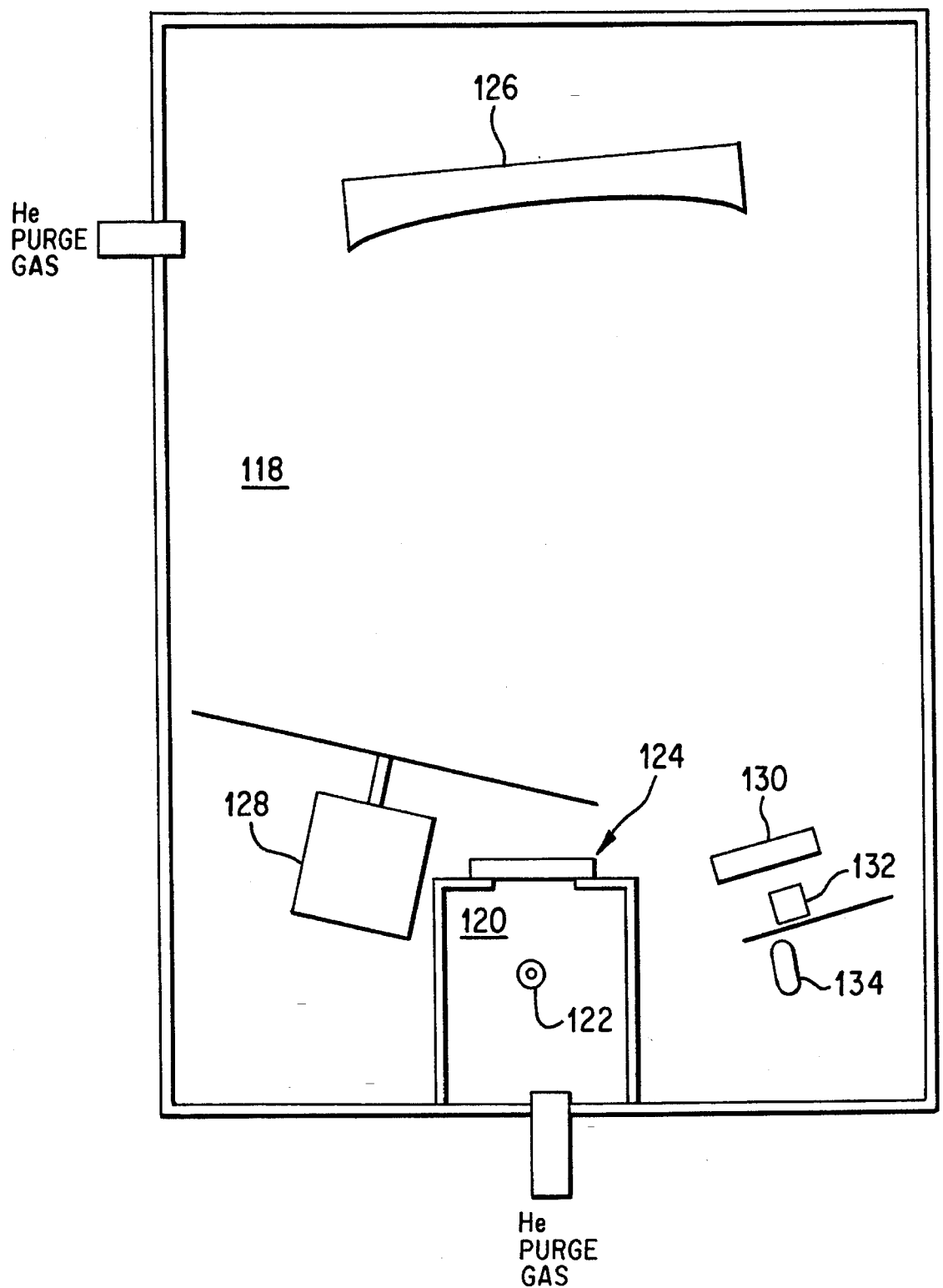
FIG. 11 shows a top view of a single channel FIRE radiometer with the cover removed; 118—first chamber houses optical components and detector, 120—second chamber houses the microburner, 122—a two-tube concentric burner, 124—CaF2 window, 126—collection mirror, 128—chopper, 130—bandpass filter, 132—PbSe detector, 134—preamplifier.
Figure 12:
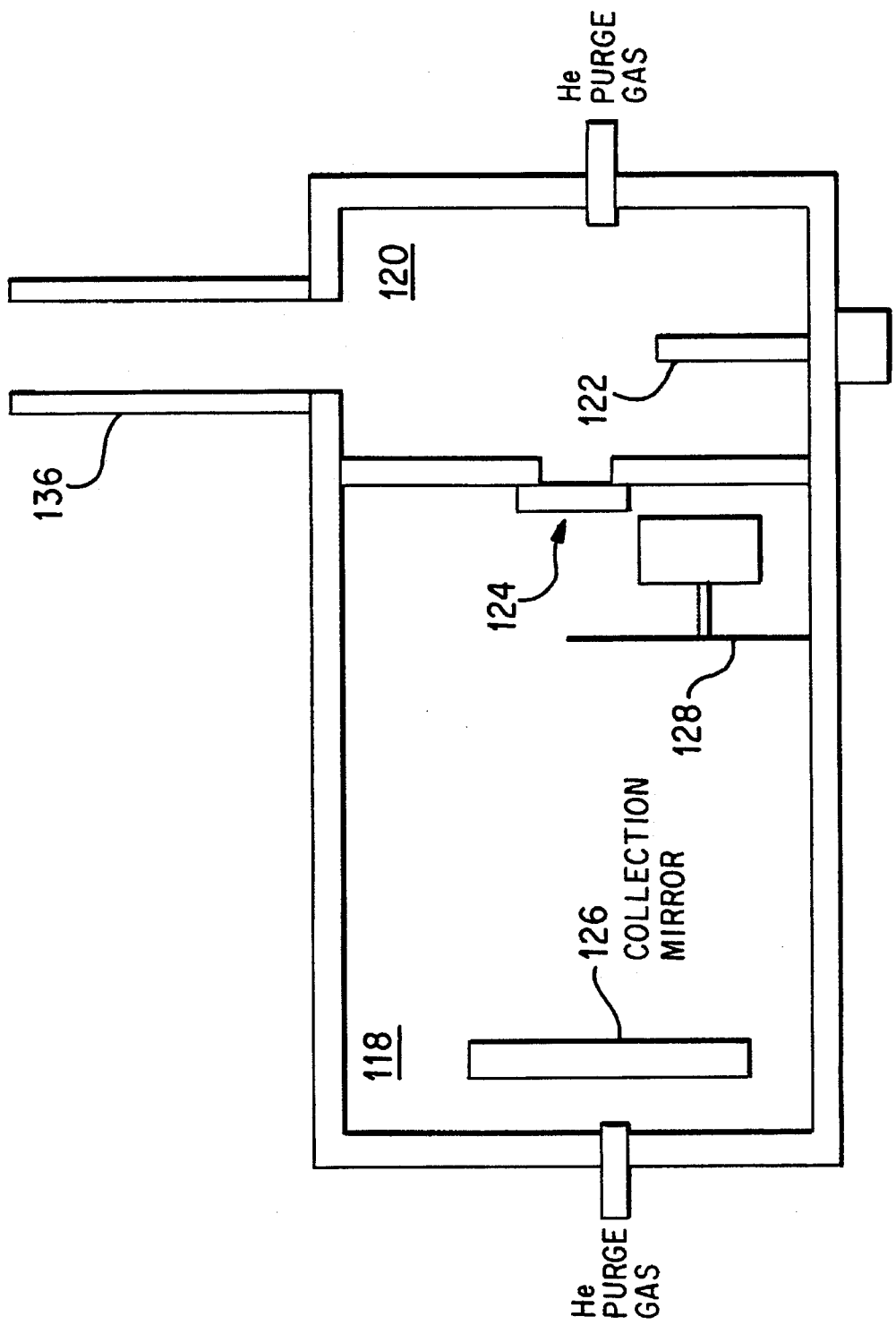
FIG. 12 shows a side view of a FIRE radiometer; 136, chimney.
Figure 13:
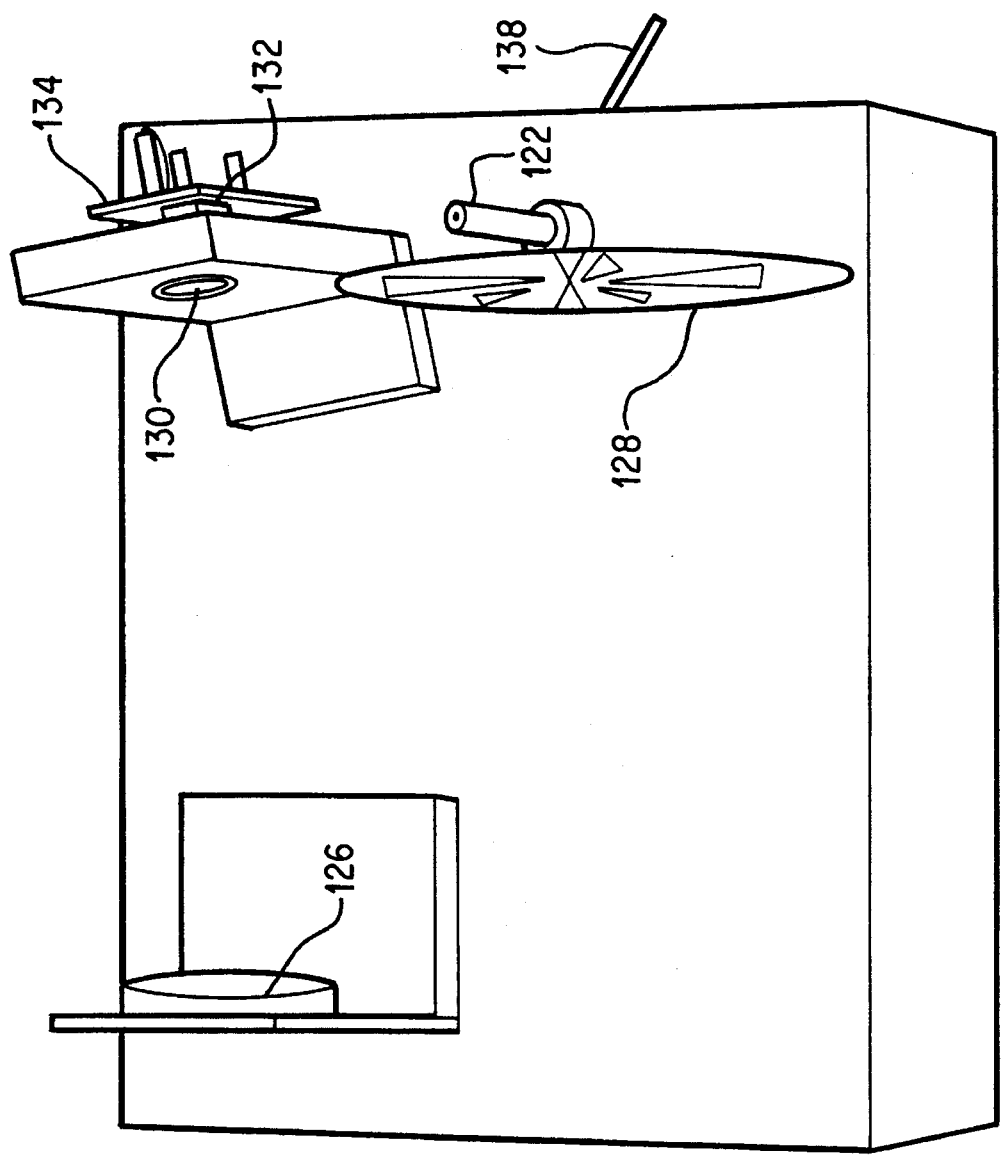
FIG. 13 shows a diagram of a single-channel FIRE radiometer with the cover and chamber B removed; 138, transfer line.
Figure 14A:
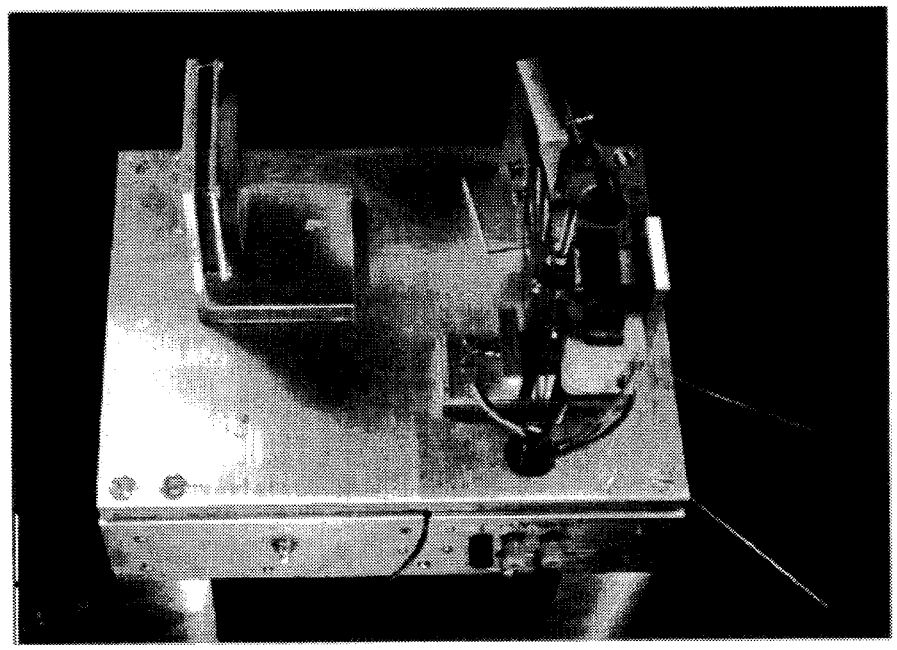
FIG. 14 shows a photograph of a FIRE spectrometer.
Figure 14B:
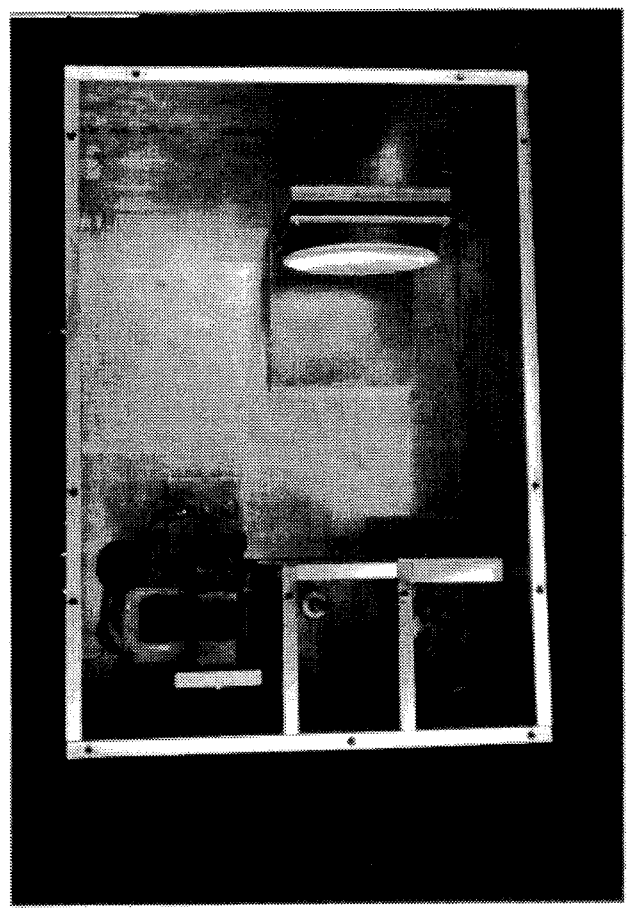
Figure 14C:
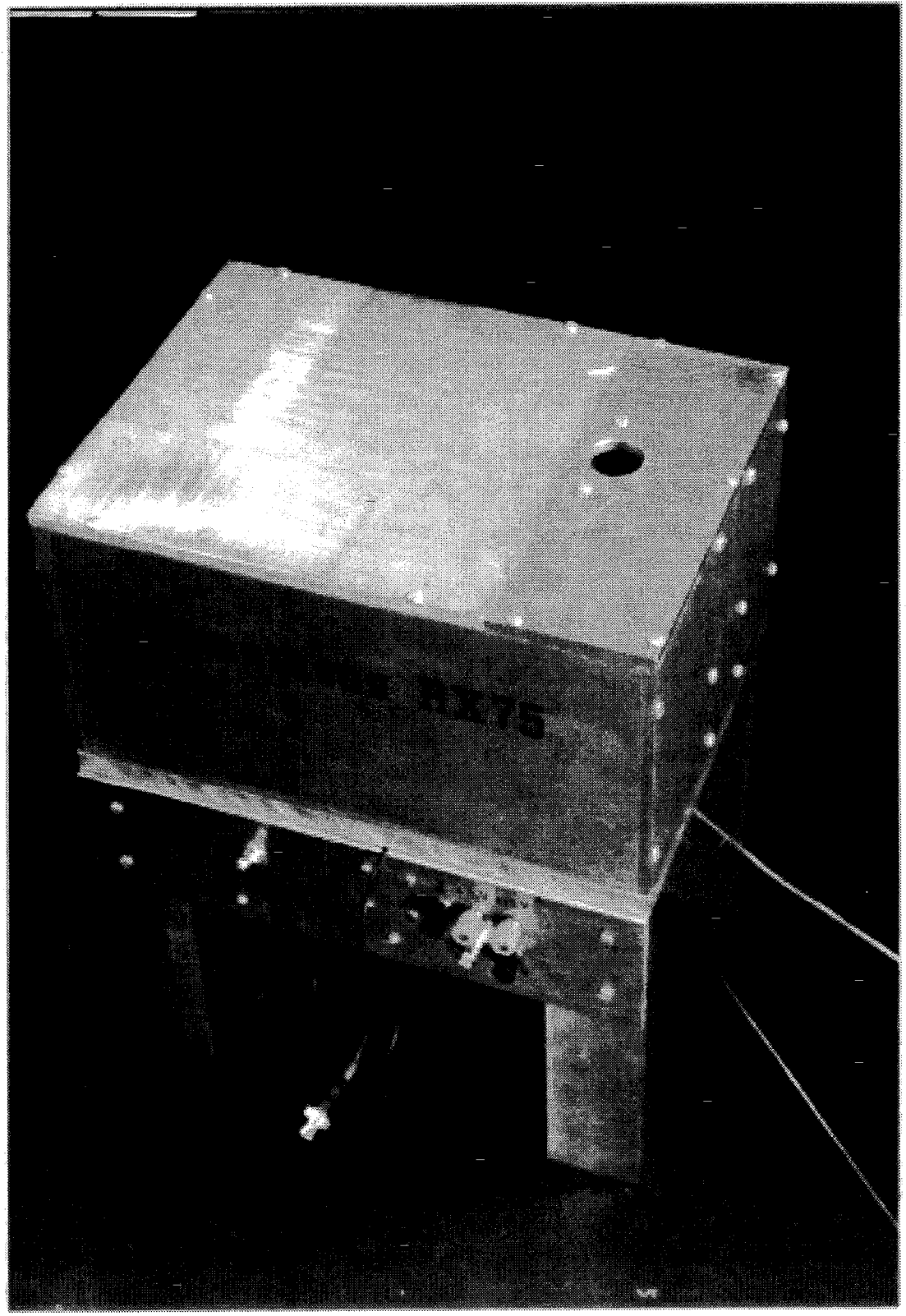

The schematic layout for the basic single-channel FIRE radiometer is shown in FIG. 11. The radiometer is divided into two chambers 118 and 120. Chamber 118 contains the optical components and the detector while chamber 120 houses the microburner that supports the flame. A two-tube concentric burner (122) as described in Example 1 is used to support a hydrogen/air or hydrogen/oxygen flame. Hydrogen and the analytical sample are mixed together in capillary tube and transfer line 138 and emerge from the central capillary. Oxidant (either air or oxygen) flows through the outer tube so that a small diffusion flame can be maintained at the tip of the burner. In gas chromatographic applications, transfer line 138 should be as short as possible and should be heated to prevent condensation of high-boiling components in the line. Failure to heat the transfer line will result in sample condensation in the transfer line that will lead to baseline drift. The flow of flame gases to the burner is adjusted to give the smallest possible flame that can be maintained on the burner. Helium make-up gas is added to transfer line 138 to maintain a suitable mass-flow rate of sample into the flame. The presence of a flame is indicated by the heating of the central capillary to an orange-red color. Use of the smallest possible flame reduces flame background and permits the use of higher amplifier gain settings on the lock-in amplifier (100 µV as opposed to 30 mV with older FIRE radiometers). Use of higher gain settings facilitates lower detection limits.

The burner is located in chamber 120 of the FIRE radiometer to isolate the flame from drafts produced by the chopper and to prevent flame gases from building up in the inside of the case of the optical section (chamber 118). A chimney in the top of the burner chamber serves to prevent the accumulation of flame gases in the burner chamber. The burner chamber must be of sufficient size that the flame does not heat the walls of the chamber (which would produce undesirable blackbody radiation that could obscure the gas-phase infrared emission). A $CaF_2$ window 124 in the front of the burner compartment allows radiation from the flame to reach collection mirror 126 in chamber 118 without allowing flame gases to enter compartment 118. The burner compartment (120) is flushed with dry He to remove atmospheric carbon dioxide and assist in the removal of flame gases from the chamber. The positive pressure produced by the purge gas (He) prevents atmospheric gases from entering chamber 120. Because of the extremely high sensitivity of the FIRE radiometer, the flame must be shielded from atmospheric effects. Without these precautions, carbon dioxide from the breath of persons standing within 5 ft. of the instrument will cause a noticeable increase in the signal that results in significant baseline drift.

Chamber 118 contains the chopper (128), the collection mirror (126), the bandpass filter (130), the PbSe detector (132), and the preamplifier (134). Radiation from the flame is chopped at approximately 580 Hz by a rotating sectored disk chopper (128) located between the flame and the collection optics (126). A 75-mm diameter front surface spherical mirror (126) with a focal length of 75 mm collects radiation from the flame and focuses an image of the flame onto a lead selenide detector (132). A bandpass filter (130) with a transmission notch selects the desired infrared emission band of the analyte from the other unwanted flame radiation and passes it through to the detector. The PbSe detector is mounted directly on a printed circuit board that contains the AC-coupled preamplifier (134) that amplifies the signal prior to its being fed to the lock-in amplifier for demodulation. Chamber 118 is tightly sealed with a top and flushed with dry He to remove atmospheric carbon dioxide.

Figure 15:
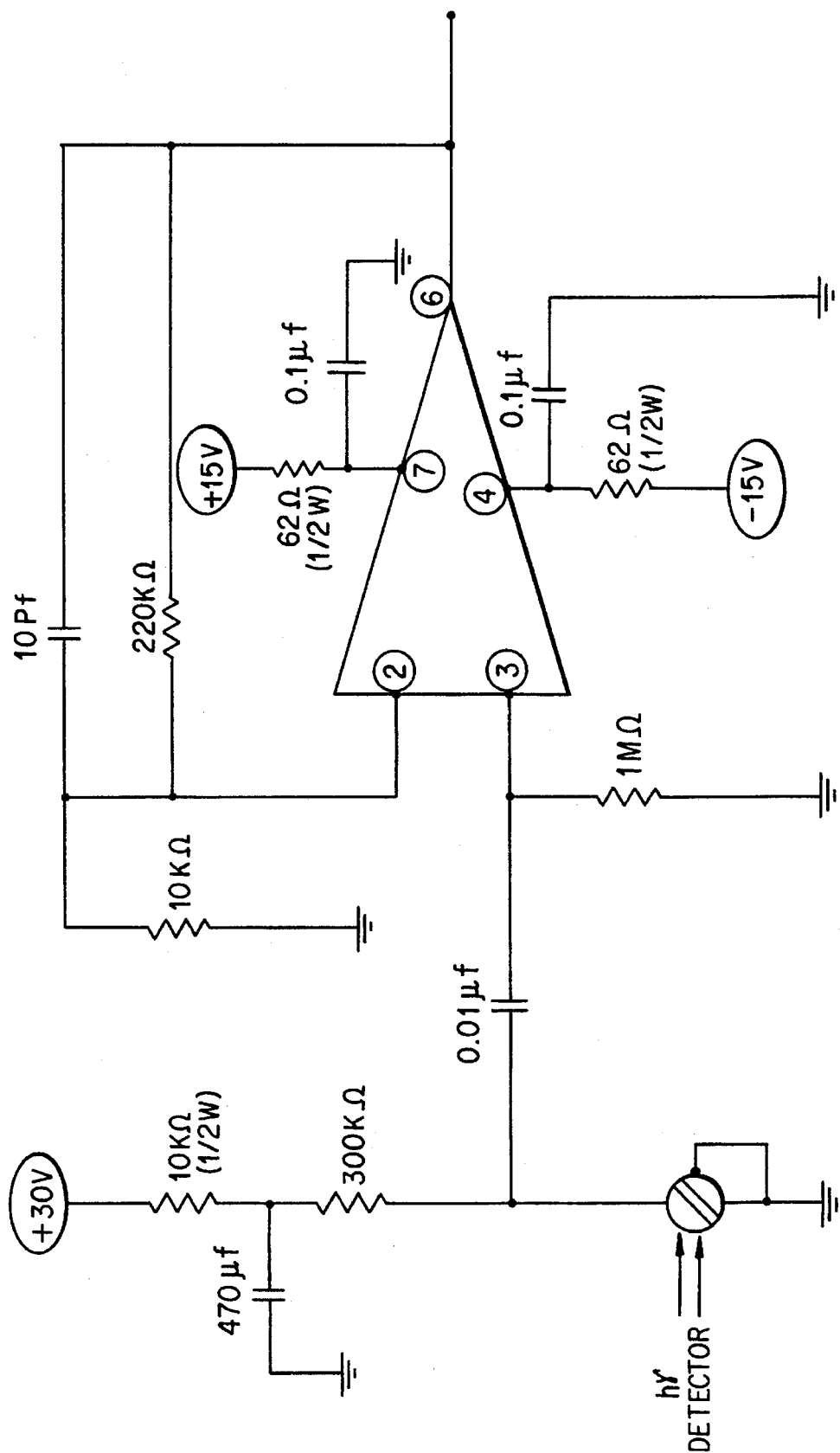
FIG. 15 shows a schematic diagram of the preamplifier circuit used in Example 2. The basic circuit is an AC-coupled voltage follower with gain.

FIG. 15 shows a schematic diagram of the preamplifier circuit used in this embodiment. The basic circuit is an AC-coupled voltage follower with gain.

Although not specifically incorporated in this prototype, a multiple mirror collection optical system such as that described by Busch et al., *Applied Spectroscopy* 45:964–968 (1991) can be employed for the purpose of increasing the solid angle of radiation collected by the detector. In this embodiment, mirrors $M_1$, $M_2$, and $M_3$ in FIG. 1 of the aforementioned reference would be located in chamber 120. Spherical mirror M in chamber 118 would replace the lenses $L_1$ and $L_2$ in FIG. 1 of the reference.

Provision can also be made for a reference detector such as described in Example 5 to reduce the effects of flame flicker and flame drift. Said reference detector would consist of a second PbSe detector with a bandpass optical filter that transmits radiation corresponding to the water background from the flame (for example, radiation at 3.0 µm). Said reference detector could be located in chamber 118 (just after the chopper) in close proximity to the flame so as to view the flame directly without the need for optical focusing components. This detector would be placed off axis to the window to view the flame directly without obscuring the field of view of the flame by mirror 126.

The optical system of the embodiment described in this example is simpler and superior in performance to the lens systems used in previous FIRE embodiments. The $CaF_2$ lenses used in previous embodiments had a limited transmission range and suffered from optical aberrations that severely degraded the image of the flame produced on the detector. This poor imaging ability resulted in radiation from the hot burner tip and less desirable regions of the flame reaching the detector and increasing the background to unacceptable levels. By contrast, the spherical mirror used in this embodiment will transmit radiation over the entire infrared spectrum. Moreover, compared with the relatively thick $CaF_2$ lenses used in previous FIRE radiometer embodiments (which had severe spherical aberrations), the use of a spherical mirror under conditions of small angles of incidence produces a very high quality image of the flame on the detector. Furthermore, use of a 3 in diameter (75 mm) spherical mirror with a 75 mm focal length results in an f/1 optical system with high collection efficiency.

Wavelength isolation with an optical bandpass filter has been accomplished in two ways in the present embodiment. The mounting bracket that holds the PbSe detector has been machined so that a standard 1 in (25 mm) bandpass filter is held in a circular depression in front of the detector by means of an O-ring. Alternatively, the filter can be incorporated in the TO-5 case that houses the detector. In this arrangement, the optical bandpass filter replaces the standard sapphire window used by the manufacturer. Detectors with integral bandpass filters built in can be obtained directly from the detector manufacturer (Cal-Sensors, Santa Rosa, Calif.) upon request by specifying the desired transmission band of the filter. This arrangement reduces the number of surfaces through which the infrared radiation must travel and is substantially cheaper to employ because more efficient use can be made of the filter material. For example, a standard 1 in filter (approximate cost $600) can be cut into many smaller pieces by the detector manufacturer so that is can be used with many detectors. By using integral filters (for example, with a transmission band at 4.4 mm) we can purchase custom detectors with built-in filters for $100 apiece in lots of 20. Without the filters, the detectors cost $69 apiece but each detector requires a $600 1-in diameter bandpass filter.

While not specifically incorporated in the present embodiment, it should be understood that cooled detectors can be used with the FIRE radiometer in place of the room temperature detectors that have been employed. Thermoelectrically cooled PbSe detectors are commercially available. Cooling extends the long wavelength response and increases the specific detectivity (D★) of the detector. Furthermore, it should be understood that other emission sources can be used with the FIRE radiometer described above. Such sources include electrically heated furnaces (Example 6) and various types of electrical discharges (Example 7).

With a hydrogen/oxygen flame, the FIRE radiometer described above has been used as a detector for gas chromatography. In this application, a Shimadzu GC-8A gas chromatograph (Shimadzu Scientific Instruments, Columbus, Md.) equipped with a 15 m×0.53 mm SPB-20 silica capillary column (Supelco, Ballafonte, Pa.) was used. Detection limits for benzene obtained with this system were 800 pg s$^{-1}$. (A picogram is $10^{-12}$ g.)

EXAMPLE 3

A miniature capillary-head burner (Hudson and Busch, 1988) was modified for use with liquid samples. As the previously designed burner was intended to admit a gas stream from the gas chromatograph to the center of the burner-head, the burner was modified for nebulized liquid samples. The central sample injection capillary was removed, and the number of small-bore capillary tubes in the burner-head was increased from 6 to 19 (the internal diameter of the capillary tubes was 0.6 mm). The overall diameter of the burner orifice was 0.5 cm. The capillary-head burner was fitted with a Jarrell-Ash model X-88 atomic absorption cross-flow nebulizer and a 3 cm long×4 cm diameter TEFLON spray chamber. The nebulizer and spray chamber were coupled to the burner body by boring a one inch hole in the side of the burner body (perpendicular to the capillary-head) and press fitting the spray chamber/nebulizer assembly to the burner.

A 1:1 hydrogen/air flame stoichiometry was used for all measurements, and the fuel and oxidant flow-rate were maintained at 200 mL/min. A 1:1 fuel/oxidant mixture resulted in a stable flame approximately 4 cm in height by 1 cm in width. The infrared emissions were observed over a 0.6 cm vertical segment centered at a height of 1.5 cm from the burner top. The reagent grade liquid samples were introduced into the flame via aspiration by the nebulizer.

All flame infrared emission spectra were acquired on an unpurged Mattson Cygnus 100 Fourier transform spectrometer. Fourier transform infrared emission spectroscopy allows multiwavelength analysis. The Fourier transform spectrometer, by virtue of the multiplex nature of the data acquisition, is a multichannel instrument and can therefore monitor all infrared wavelengths simultaneously. Since the desired molecular emission occurs in the infrared spectral region, any standard, commercially available Fourier transform-spectrometer can be utilized without the need for special optics, beamsplitters, or detectors. The Fourier transform instrument also provides several advantages for infrared emission spectroscopy. These advantages include: a single instrument for both elemental and molecular analysis, high optical throughput, good spectral resolution, accurate wavelength recording due to the reference laser, the ability to signal average by coaddition, and the capability of performing spectral subtraction.

Figure 16:
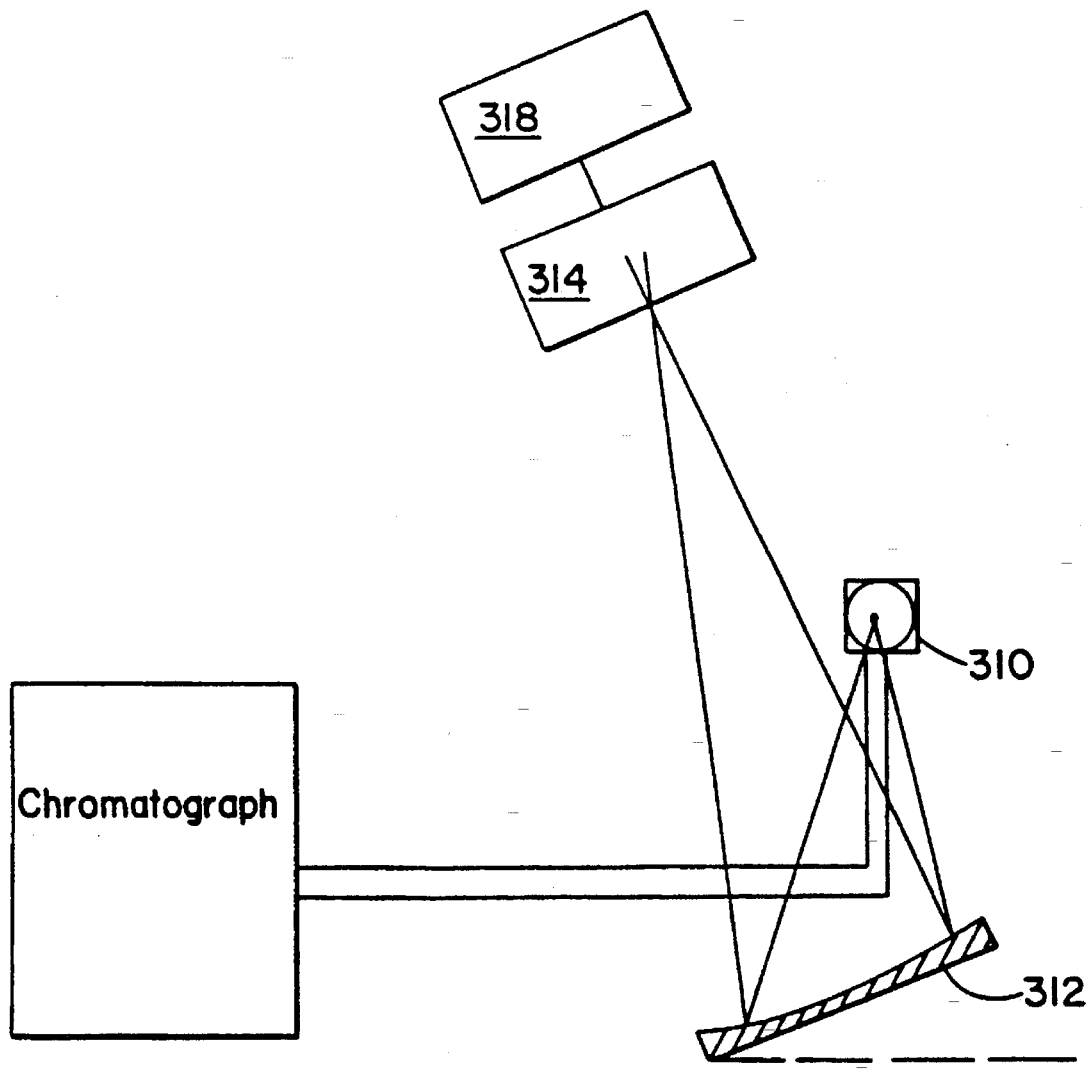
FIG. 16 schematically illustrates the experimental set up of the burner, mirror and Fourier transform spectrometer for Example 3.
Figure 17:
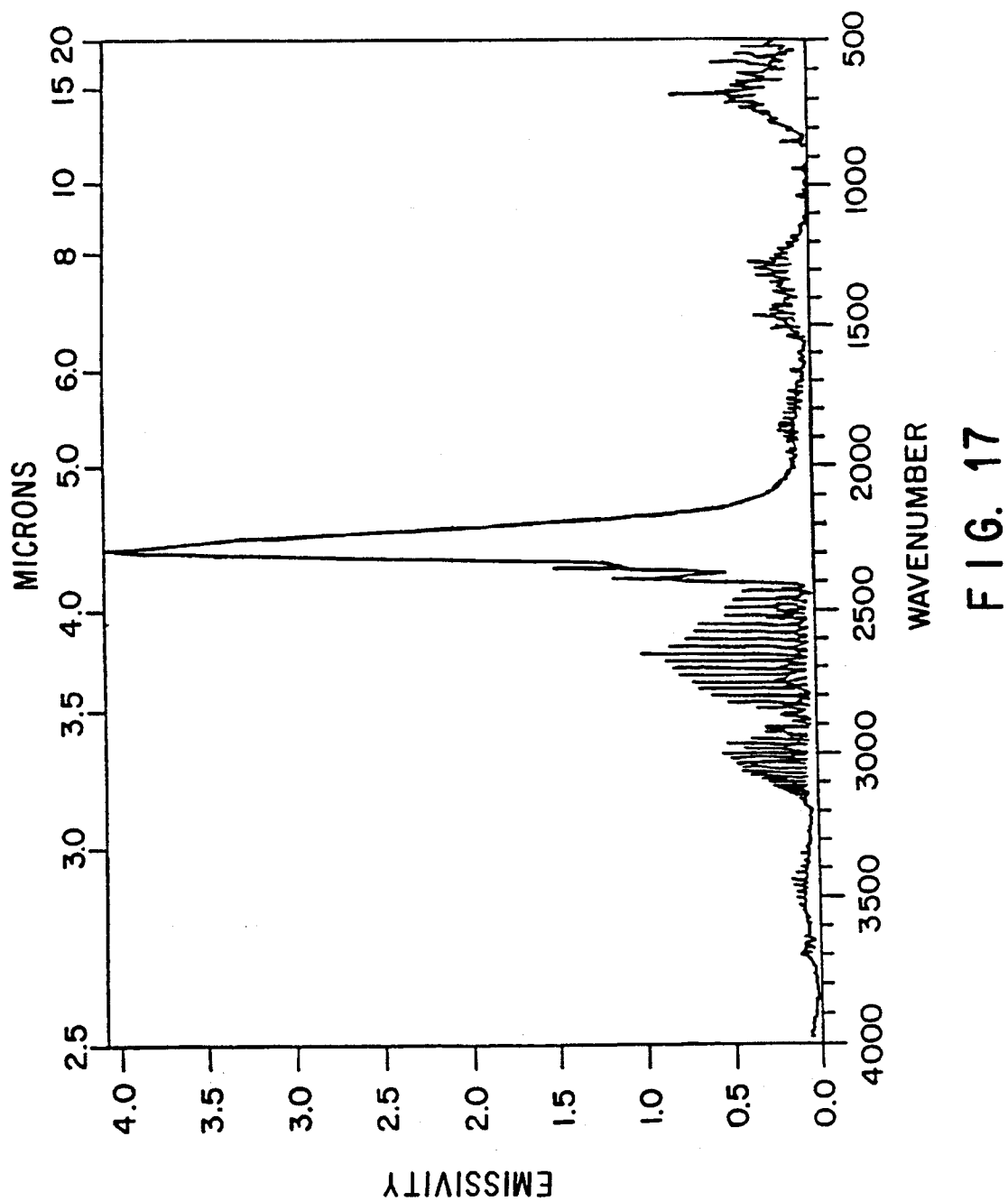
FIG. 17 is a flame infrared emission spectrum of carbon tetrachloride.
Figure 18:
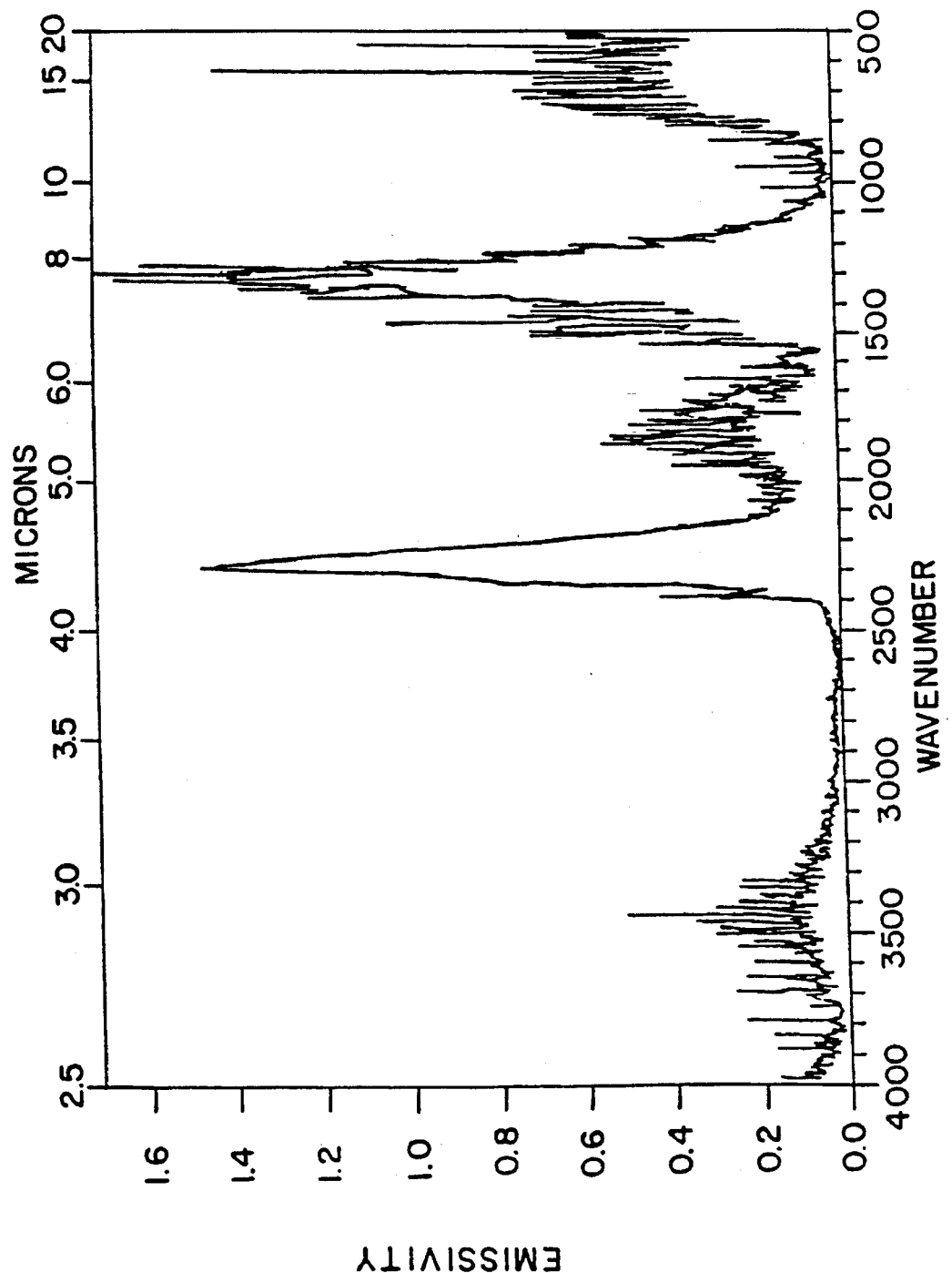
FIG. 18 is a flame infrared emission spectrum of methanesulfonyl fluoride.
Figure 19:
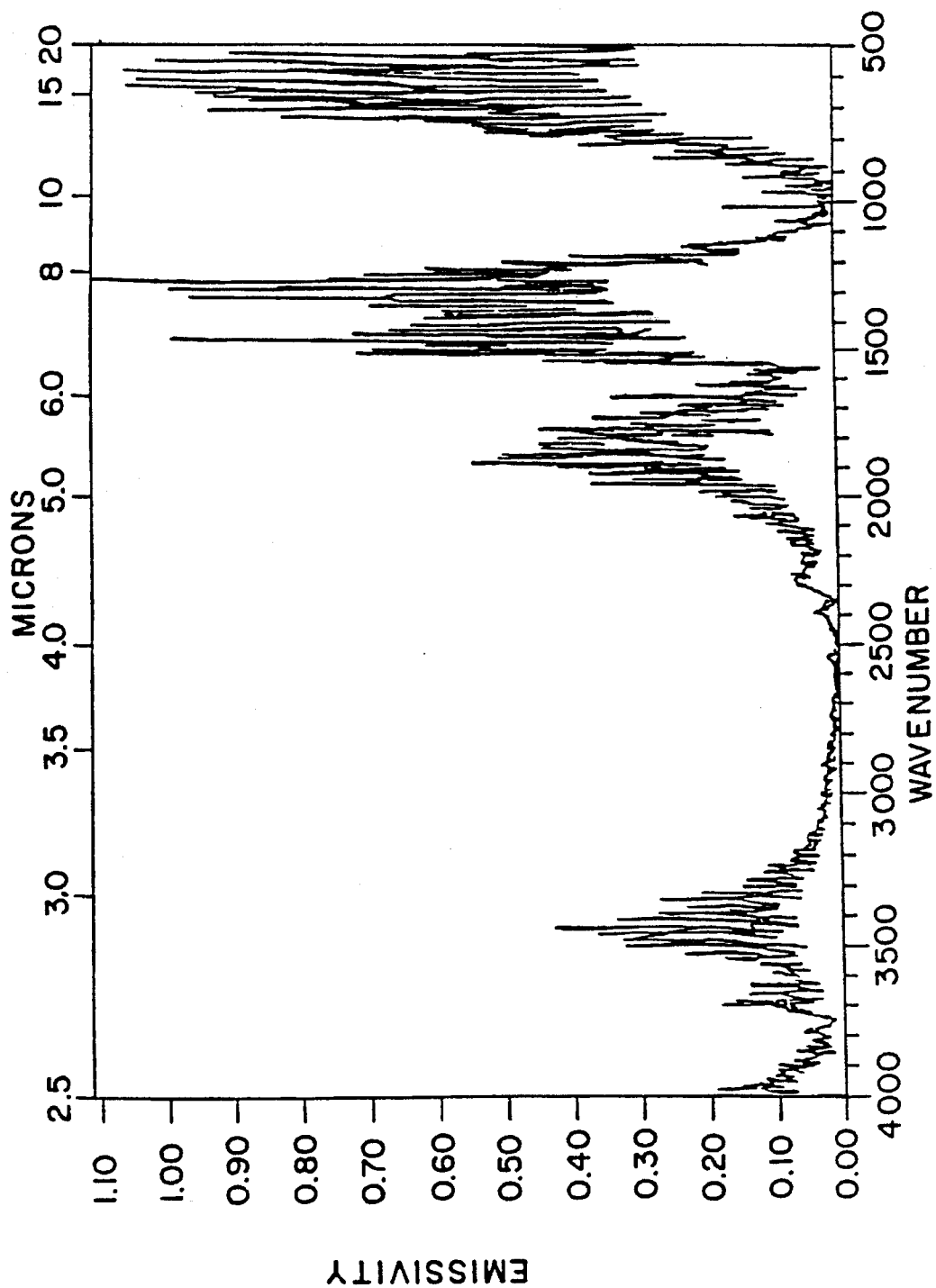
FIG. 19 is a flame infrared emission spectrum of the H$_2$/air background at high gain.
Figure 20:
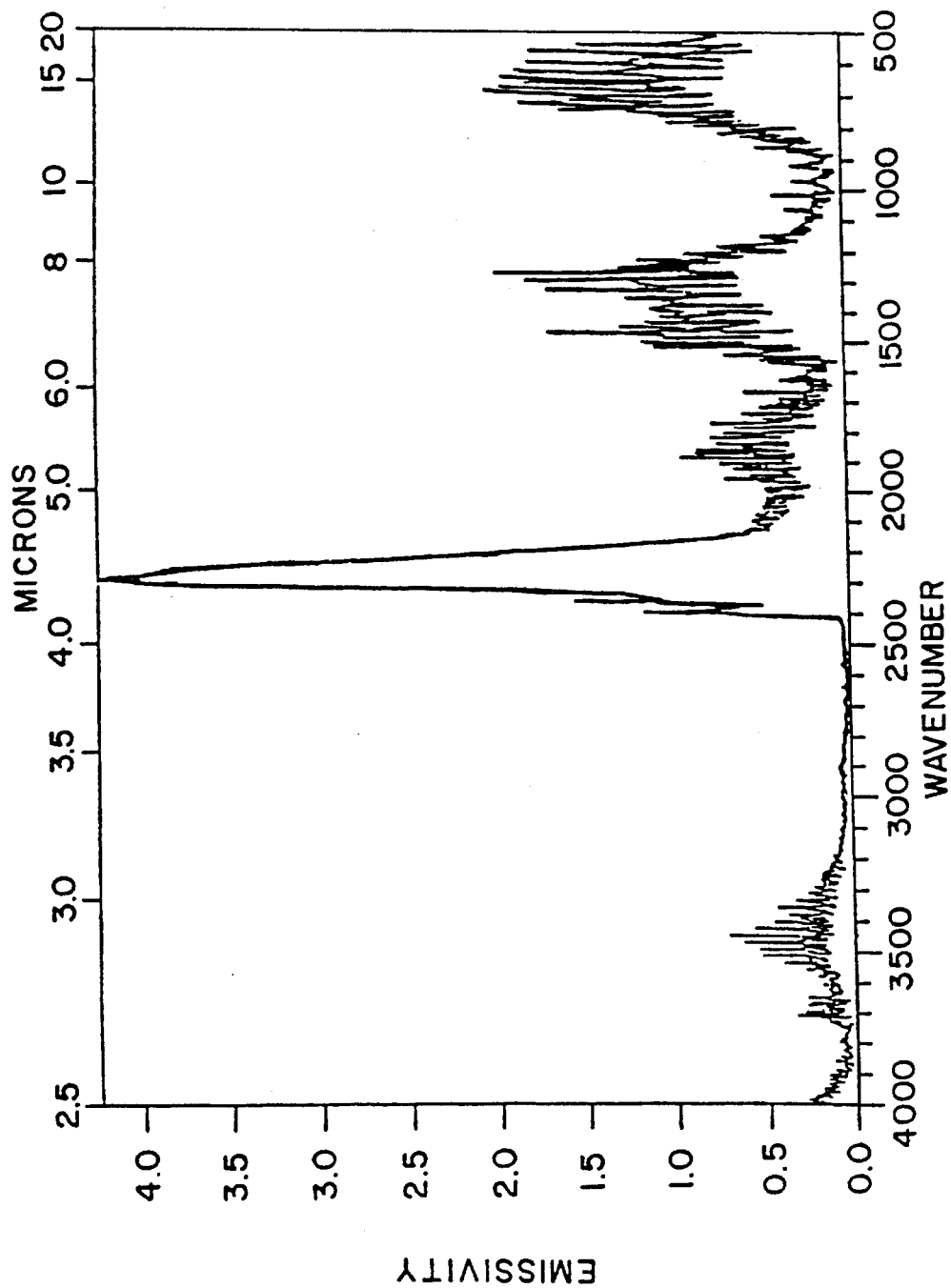
FIG. 20 is a flame infrared emission spectrum of methanol.
Figure 21:
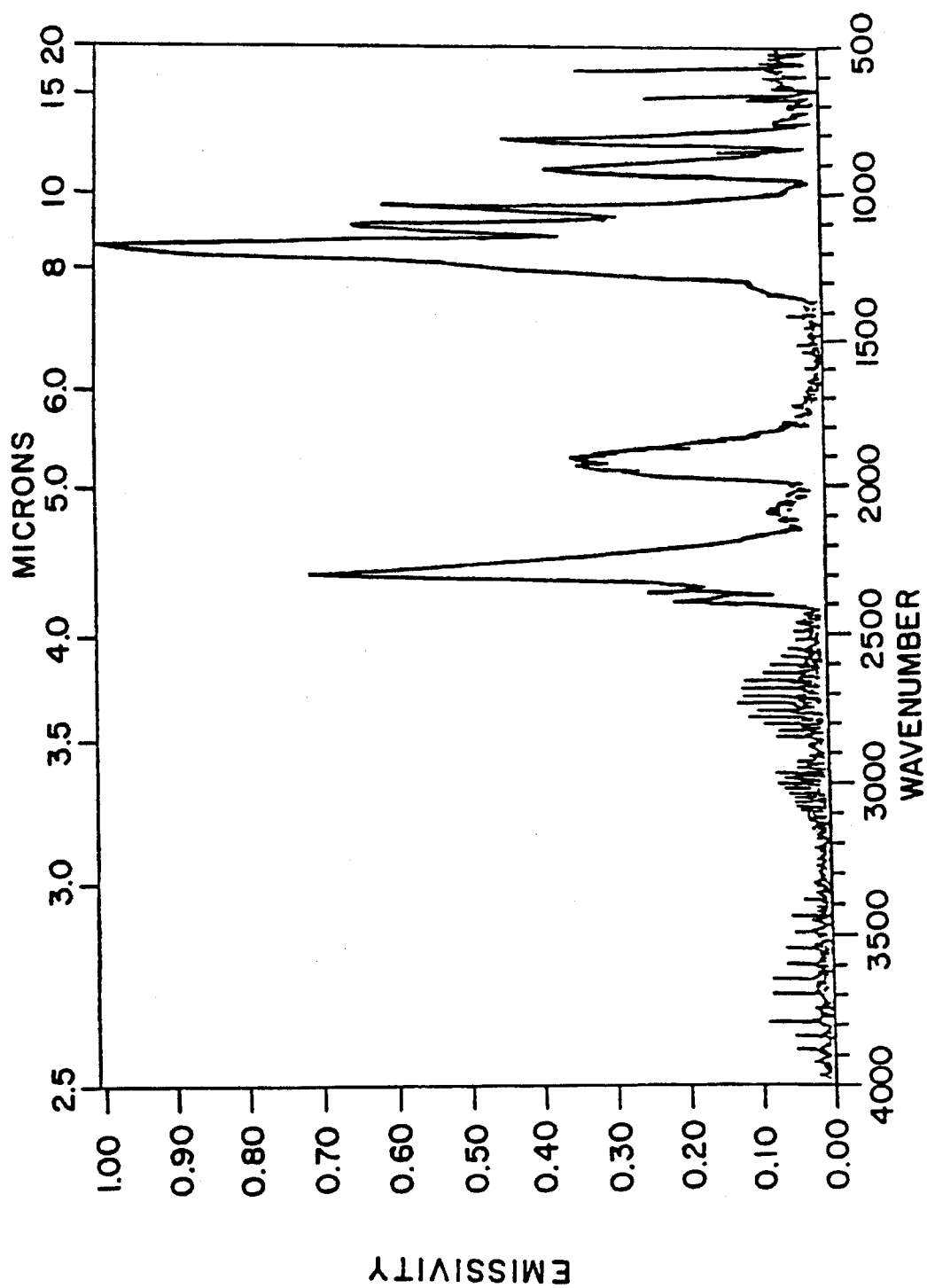
FIG. 21 is a flame infrared emission spectrum of trichlorotrifluoroethane.
Figure 22:
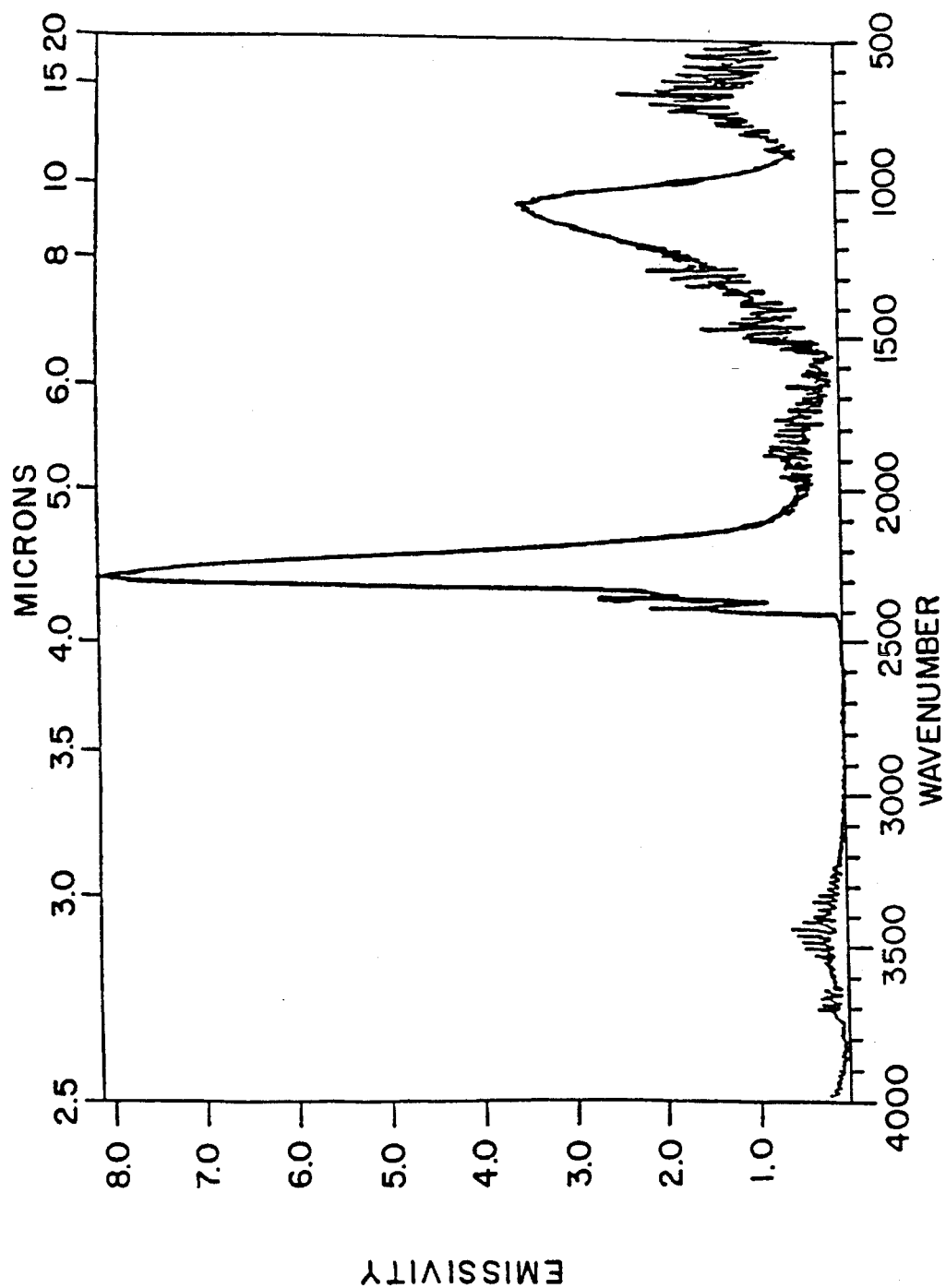
FIG. 22 is a flame infrared emission spectrum of tetramethylsilane.

FIG. 16 schematically shows the arrangement of the burner 310, mirror 312 and Fourier transform-spectrometer 314 for Example 3. A 5-cm-focal-length, 10-cm-diameter aluminum mirror 312 was used to collect and collimate the infrared emissions from the flame. It should be noted that the infrared collection mirror 312 was placed off the optical axis by approximately 30 degrees. No significant aberrational defects were observed.

A room temperature, triglycine sulfate (TGS) detector ($D^* = 2 \times 10^9$ cm H$^{1/2}$ W$^{-1}$) and KBr beamsplitter were employed in the Fourier transform-spectrometer 314. All spectra were acquired with 4 cm$^{-1}$ resolution at a mirror velocity of 0.32 cm/s. A triangular apodization function was used with 1X zero filling and, due to the discrete line nature of the emission spectra, phase correction was not applied. Instead, the single-beam power spectra were calculated and plotted, and none of the spectra in FIGS. 17–22 have been corrected for instrumental response.

The hydrogen/air flame was chosen to excite the molecules of interest in order to eliminate carbon dioxide emissions from the fuel gases. Otherwise, the determination of carbon, as carbon dioxide, would be significantly impaired.

FIGS. 17–22 are characteristic infrared emission spectra for carbon tetrachloride, methanesulfonyl fluoride, the H$_2$/Air flame background, methanol, trichlorotrifluoroethane and tetramethylsilane. These spectra clearly show that bands other than those from H$_2$O and CO$_2$ can be observed in the flame.

EXAMPLE 4

Figure 23:
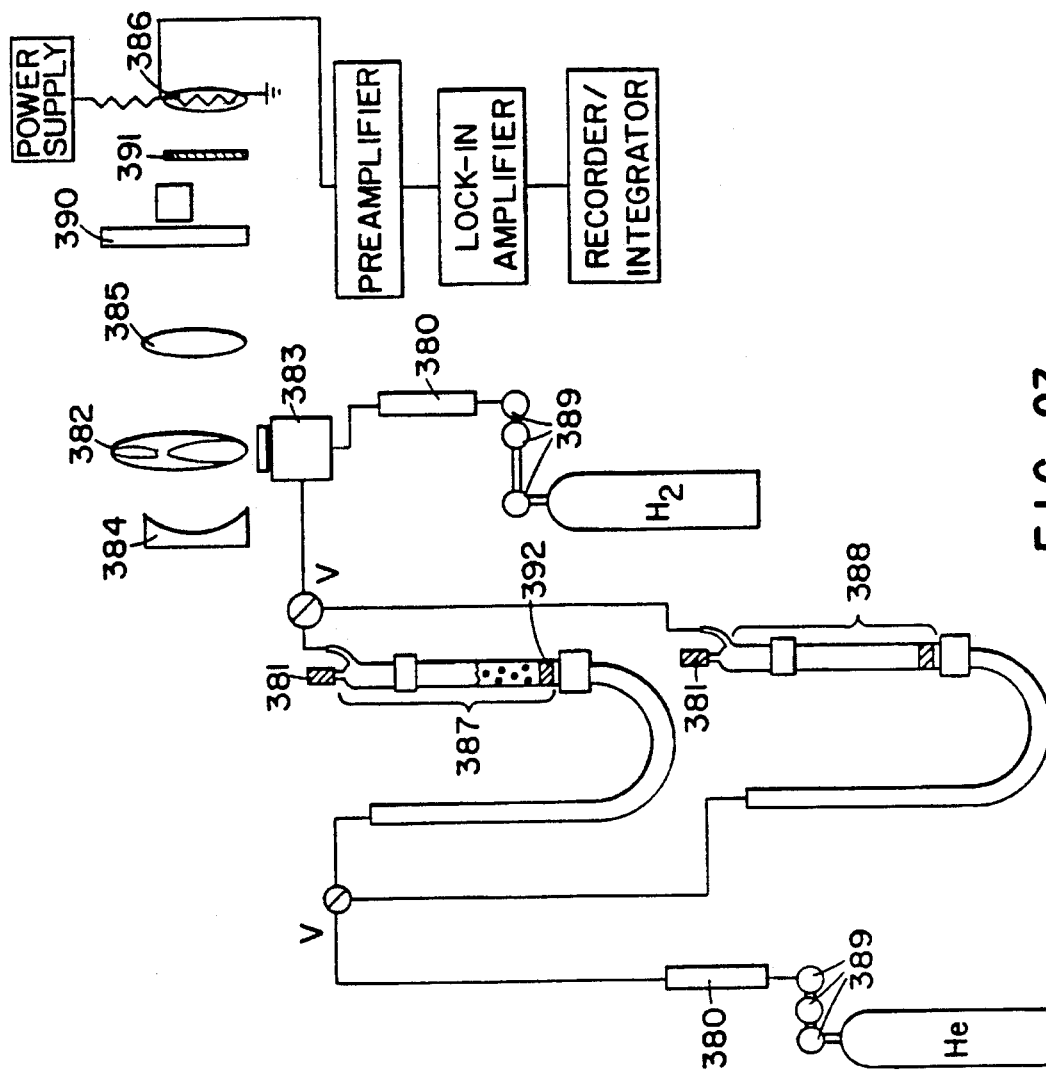
FIG. 23 schematically illustrates the experimental set up for Example 4 for the determination of chloride and available chlorine in aqueous samples.

The chlorine sensitive flame infrared emission detection instrument is shown in FIG. 23. The instrument consists of a chlorine generation and liberating apparatus and a flame infrared emission detection system. The chlorine generation and liberating apparatus contains two purge devices 387 and 388 (model #991710, Wheaton Scientific, Millville, N.J.) connected together in parallel using 3.2 mm o.d. polyethylene tubing and two, three-way valves (model #B-42XS4, Whitey Co., Highland Heights, Ohio) as described in Kubala et al., *Anal. Chem.*, 1989, Vol. 61 pgs. 1841–1846, incorporated herein by reference. One of the purge tubes serves as the sample chamber 387 while the second serves as the reference chamber 388.

Each purge device consists of a 5-mL demountable tube that can be disconnected for sample introduction and cleaning. A septum 381 located at the top of each purge tube allows the samples and reagents to be introduced by syringe (sulfuric acid syringe: model #2300, Becton-Dickson & Co., Rutherford, N.J.; KMnO$_4$ syringe: model #1001, Hamilton Co., Reno, Nev.; water sample syringe: model #1002, Hamilton Co., Reno, Nev.).

Helium gas, maintained at a flow rate of 130 mL/min, was used to purge evolved Cl$_2$ from the aqueous solutions into the flame 382 of the flame infrared emission detector. The optimum flow rate of hydrogen in the capillary-head burner 383 (Hudson and Busch, 1988) was determined to be 324 mL/min with combustion supported only by entrained air. The supply pressures of the helium and hydrogen were regulated at 0.75 atm using triple-stage regulation 389.

The optical system of the flame infrared emission detector was modified from that described in Kubala et al., *Anal. Chem.*, 1989, Vol. 61, pgs. 1841–1846 by the addition of a 5-cm-focal-length, f/1 concave mirror 384 (Model #44340, Oriel Corp., Stratford, Conn.) installed behind the hydrogen/air flame. This back collection mirror 384, in conjunction with the CaF$_2$ lens 385, directed the infrared emission from the flame onto the PbSe detector 386.

In addition to the installation of the back collection mirror 384, the flame infrared emission detector was also modified by replacing the 4.4 µm CO$_2$ optical bandpass filter described in Kubala et al., *Anal. Chem.*, 1989, Vol. 61, pgs. 1841–1846, with a 3.8 µm optical bandpass filter 391 (Model #S-902-079, Spectrogon, Secaucus, N.J.) to spectrally isolate a portion of the HCl emission consisting of most of the more intense part of the R branch. This optical bandpass filter 391 possessed a full-width at half-maximum height (FWHM) of 0.18 µm and was placed immediately in front of the detector 386.

The flame infrared emission was detected using a PbSe photoconductive cell operated at room temperature with a bias potential of 45 V. The detector preamplifier circuit, lock-in amplifier and recorder/integrator have been previously discussed in Kubula et al., *Anal. Chem.*, 1989, Vol. 61, pgs. 1841–1846 except for a slight change in the preamplifier circuit to allow for a larger bias voltage.

All chemicals were A.C.S. reagent grade and were used without further purification. A stock solution of 100 mM NaCl (Mallinckrodt, Inc., St. Louis, Mo.) was prepared by dissolving NaCl, dried at 120° C. for 24 hours, in deionized water. Standard NaCl solutions, having concentrations of 0.1, 0.5, 1.0, 2.0, 5.0, 8.0, and 10 mM, were prepared before use by diluting aliquots of the stock solution to the appropriate volumes.

A saturated solution of $KMnO_4$ (Mallinckrodt, Inc., St. Louis, Mo.) used in conjunction with concentrated $H_2SO_4$ (Mallinckrodt, Inc., St. Louis, Mo.) served as the oxidizing agent for the aqueous chloride determinations. The saturated $KMnO_4$ solution was boiled and filtered to remove any $MnO_2$ that might be present. Aqueous solutions of $AgNO_3$ (Thorn Smith, Inc., Beulah, Minn.) and $Na_2S_2O_3$ (Sargent-Welch Scientific Co., Skokie, Ill.) were used in the titrimetric analysis of aqueous chloride and available chlorine, respectively.

Prior to use, the flame in the flame infrared emission system was ignited, and the instrument was allowed to warm up until a stable baseline was obtained on the chart recorder. As part of the warm-up procedure, He purge gas was directed through the dry reference purge tube and into the flame. When the instrument had stabilized, the analysis for aqueous chloride or available chlorine was carried out according to the appropriate procedure indicated below.

Aqueous Chloride

To construct a calibration curve for chloride using the flame infrared emission system, the sample purge tube 387 was disconnected, a 1.0-ml volume of an aqueous chloride standard was placed on the glass frit 392, and a 0.5-mL volume of concentrated $H_2SO_4$ was added using a syringe. The purge assembly was then reconnected, and the He flow was switched from the reference purge tube 388 to the sample purge tube 387 using the dual, three-way valve system. The acidified standard solution was purged for approximately 70 seconds. A 0.1-mL aliquot of the saturated $KMnO_4$ solution was injected through the septum 381 and into the sample chamber using a syringe. The chlorine gas produced from the resulting oxidation of the aqueous chloride in the sample was liberated from the solution and introduced into the flame where it formed vibrationally excited HCl.

After the resulting HCl infrared emission peak had been recorded, the He flow was switched back through the reference purge device. The sample purge tube 387 was then disconnected and rinsed thoroughly with deionized water to remove excess reagents. This process was repeated for all chloride standards to construct a calibration curve of peak intensity versus chloride concentration.

Several natural water samples were collected from sources around the Waco area and stored according to standard procedures. One-mL volumes of these natural water samples were treated using the same procedure as outlined for the preparation of the chloride calibration curve, and the resulting infrared emission signal was recorded. Aqueous chloride concentrations in these natural water samples were read from the calibration curve using measured peak heights. For comparison purposes, aqueous chloride in these samples was also determined by argentometric titration using 0.0136N $AgNO_3$ with potassium chromate as an indicator according to procedures outlined in *Standard Methods for the Examination of Water And Wastewater*, (16th ed.; Greenberg, A. E.; Trussell, R. R.; Clesceri, L. S.; Franson, M. A. H.; Eds.; American Public Health Association: Washington, DC 1985; pp. 287–294).

Available Chlorine

Calibration curves for available chlorine ($Cl_2$, HOCl and $OCl^-$) were constructed using aqueous chloride standards as described previously. Bleach sample concentrations were read as chloride concentrations from the chloride calibration curve and converted into available $Cl_2$ concentration using the relationship, $\frac{1}{2}[Cl^-]=[Cl_2]$.

To determine available chlorine in bleach using the flame infrared emission system, a 0.5-mL aliquot of concentrated $H_2SO_4$ and a 1.0-mL volume of deionized water were added to the disconnected sample purge tube 387 as described for the aqueous chloride determinations. The sample purge device 387 was then reconnected and the He purge gas flow switched from the reference purge device to the sample purge device. After purging this acidified deionized water solution for approximately 70 seconds, a 0.1-mL aliquot of a bleach sample, diluted by a factor of 20 with deionized water, was introduced through the septum using a syringe. The $Cl_2$ gas generated from the acidification of the bleach sample was purged from the solution into the flame 382 where it formed vibrationally excited HCl. After the HCl infrared emission peak had been recorded, sample clean-up was performed as described previously.

Three commercially available bleach solutions were selected for the determination of available chlorine. For comparison purposes, available chlorine in these samples was also determined by iodometric titration using 0.151N $Na_2S_2O_3$ according to the procedure outlined in Standard Methods as referenced above.

The flame infrared emission detection system used in this experiment for the determination of chloride and available chlorine is similar to the system which has been previously described for use in total inorganic carbon (TIC) determinations in Kubala et al., *Anal, Chem.*, 1989, Vol. 61, pgs. 1841–1846.

However, since the HCl infrared emission band occurs in the 3.16–4.24 μm spectral region of the hydrogen flame (FIG. 24B), the 4.4 μm optical bandpass filter used to isolate the $CO_2$ emission was replaced with a 3.8 μm bandpass filter.

Figures 24A, 24B, 24C:
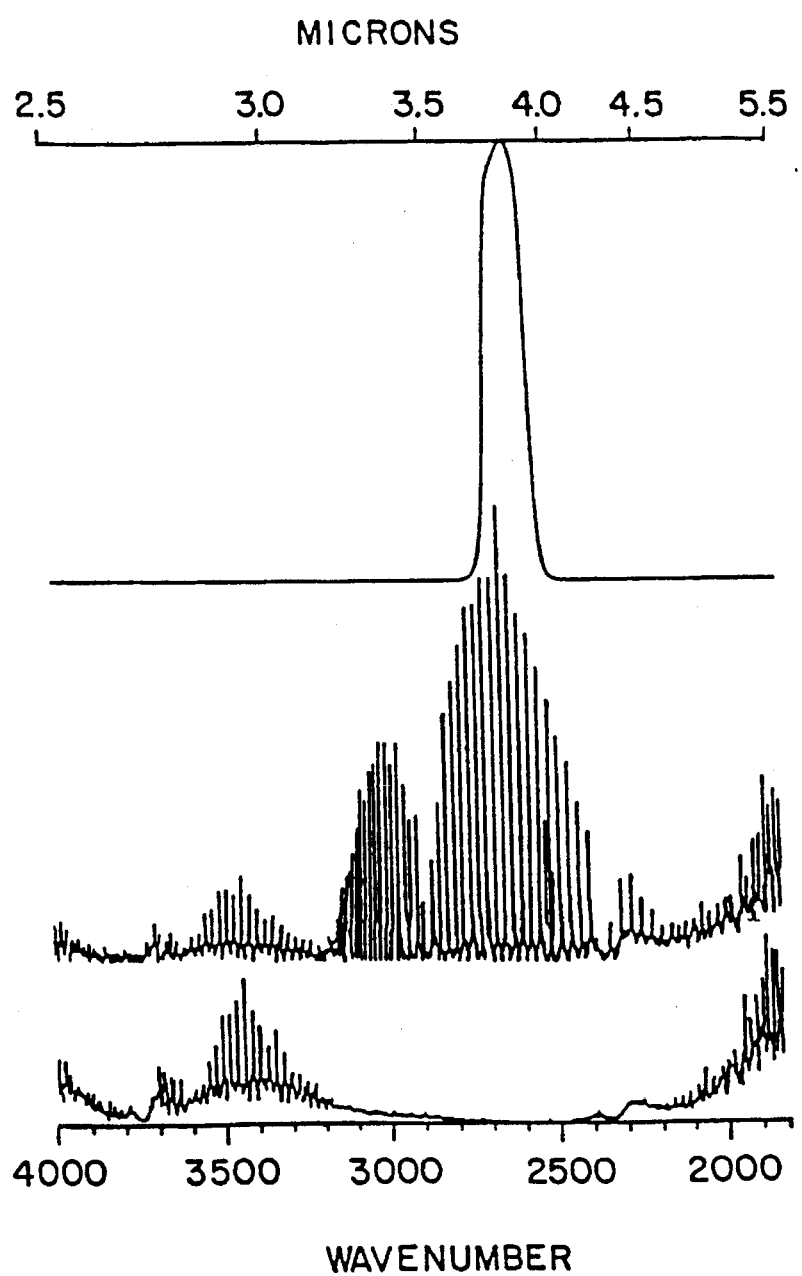
FIGS. 24A to 24C are Fourier-transform infrared spectra from 4000–1800 $cm^{-1}$ plotted on the same relative intensity scale (not corrected for instrument response) of (A) transmission spectrum of the bandpass filter, (B) flame infrared emission spectrum of HCl, and (C) flame infrared emission spectrum showing the background emission from water.

The spectra shown in FIGS. 24A–24C were obtained on a Mattson Cygnus 100 Fourier-transform infrared spectrometer. FIG. 24A is a transmission spectrum of the bandpass filter used in the flame infrared emission detector (maximum transmission at 3.8 μm 75% T, 0.10% elsewhere). FIG. 24B is a flame infrared emission spectrum from a hydrogen/entrained-air flame containing hydrogen chloride wherein the strong HCl stretching vibration is centered at 2900 $cm^{-1}$. FIG. 24C is a flame infrared emission spectrum from a hydrogen/entrained-air flame in the absence of hydrogen chloride showing the background emission from water. The resolution conditions are sufficient to reveal the rotational fine structure associated with the P- and R-branches of the HCl emission band (FIG. 24B). As shown in FIG. 24A, the 3.8 μm bandpass filter optically isolated the 3.64–4.03 μm portion of the R-branch of the HCl emission band. The corresponding flame background spectrum (FIG. 24C), shows that this region of the spectrum should be ideal for the detection of hydrogen chloride. A comparison of FIGS. 24A and 24C also indicates that a filter with a somewhat wider bandpass could have been used and would have been desirable from the standpoint of enhancing the total HCl emission received by the PbSe detector. However, to our knowledge, the filter selected for this study possessed the widest spectral bandpass in this region of any which were commercially available.

In contrast to the intensity of the water emission bands lying within the bandpass of the 4.4 µm $CO_2$ filter, the water emission bands occurring within the bandpass of the 3.8 µm HCl filter are relatively weaker (FIG. 24C) and produce a background signal approximately 12 times lower than in the case of $CO_2$ detection. Since the intensity of the HCl infrared emission band transmitted through the 3.8 µm optical filter is also weaker in comparison to the intensity of the $CO_2$ infrared emission band transmitted through the 4.4 µm optical filter, a detector-noise-limited situation was encountered, i.e. the noise amplitude was independent of the flame.

In order to increase the signal at the detector and, thus, improve the signal-to-noise ratio (SNR) of the system, two additional instrumental modifications were made. First, the detector bias voltage was increased from 30 V to 45 V in order to enhance the detectivity of the PbSe detector (*Infrared Detectors*; Hamamatsu Photonics, K. K., Solid State Division; 1126 Ichinocho, Hamamatsu City, 435, Japan, February 1985). Second, a back collection mirror 384 (FIG. 23) was added behind the burner 383 to increase the light throughput of the optical system. The location of this mirror 384 was determined experimentally by adjusting the mirror position until the signal from the flame background water emission was maximized at the detector. Use of the mirror 384 enhanced the light throughput by a factor of 2.5. Both of these modifications resulted in improved SNR's and lower detection limits.

The purging apparatus (FIG. 23) consisted of two separate chambers, one for sample introduction and chlorine generation, and a second which served as a reference. Two, three-way valves permitted the He purge gas flow to be switched from one chamber to the other between sample determinations. In the previous study (Kubala et al., 1989), degassed water was used in the reference purge tube 388 to maintain a constant flow of He saturated with water vapor to the flame. However, due to the corrosive nature of $Cl_2$ gas in the presence of water, it was found necessary to flow dry He through the reference chamber and the sample introduction system between sample determinations. This removed residual moisture from the walls of the sample introduction system and reduced corrosion of the burner and plugging of the sample introduction capillary. Therefore, in contrast to the flame infrared emission-TIC procedure, the flame infrared emission-Cl procedure employed a dry reference purge tube 388.

Because the flame infrared emission system functions as a mass flow-rate detector (Hudson and Busch, 1988), the intensity of the signal arising from the vibrational excitation of HCl in the hydrogen flame is a function of both the He flow rate and hydrogen/air ratio. Although higher He flow rates resulted in increased peak heights and therefore increased signal-to-noise ratios, a practical upper limit was reached when the sample was forced out of the purge tube. A He flow rate of 130 mL/min was determined to represent the best compromise condition for maximizing signal-to-noise ratio without sample loss.

Because chlorine gas must be reduced by $H_2$ at flame temperatures to produce HCl $$H_2+Cl_2=2HCl$$

a fuel-rich flame was expected to enhance HCl emission and improve detection limits. As anticipated, a pure $H_2$ flame, supported only by entrained air, afforded SNR's that were approximately 2.5 times greater than those obtained under fuel-lean flame conditions.

To perform chloride determinations using the flame infrared emission system, the chloride ion must first be oxidized to chlorine gas in the sample chamber. The generation of chlorine gas from aqueous chloride samples requires a suitable oxidizing medium. To be satisfactory for use with the flame infrared emission detector, the oxidizing agent must meet two basic requirements. First, it must have a reduction half-cell potential sufficient to oxidize chloride ion to chlorine (in excess of +1.36 volts under standard conditions). Second, the kinetics of the oxidation must be fast. If generation of chlorine gas does not proceed rapidly, broad peaks will be obtained which adversely affect the sensitivity of the system.

Several oxidizing agents were investigated, including concentrated solutions of acidified potassium peroxydisulfate, manganese dioxide, and potassium permanganate. While acidified solutions of both potassium peroxydisulfate and manganese dioxide have suitable half-cell potentials for the reaction, the rate of chlorine production was too slow to be useful for the analysis. By contrast, saturated aqueous $KMnO_4$ and concentrated $H_2SO_4$ generated chlorine rapidly and quantitatively, and permitted analysis by the flame infrared emission system with good detection limits.

More extensive investigations also showed that the sulfuric acid played a role beyond that of supplying hydrogen ions for the reaction, which in excess permanganate is, $$2MnO_4^-+6Cl^-+8H^+=3Cl_2+2MnO_2+4H_2O$$

By first introducing the chloride-containing solution onto the glass frit of the purge tube and then adding concentrated sulfuric acid, considerable heat was generated. This heat was found to be critical for promoting the rapid generation of $Cl_2$ in the next step of the procedure when permanganate was added.

In the analysis of bleach samples, sulfuric acid and deionized water were first introduced onto the frit, a stable baseline was re-established (about 70 seconds), and finally the bleach sample was introduced onto the hot, degassed acid. This procedure produced sharp peaks with good reproducibility. Although the reverse procedure (acid added to the degassed bleach) was not tested, degassing the bleach was avoided since the procedure could result in loss of dissolved chlorine ($Cl_2$) from the sample and degrade the accuracy of the analysis.

The total time required for signal acquisition from an aqueous sample was approximately 3.5 min (from initial acid injection to purge tube disconnection and clean-up). By judicious selection of the oxidizing medium (for chloride) and proper ordering of reagent addition, good peak profiles were obtained (FIG. 25A–25B). The hydrogen chloride signal profiles shown in FIG. 25A were obtained by treatment of an acidified 1.0 ml aliquot of 8.00 mM NaCl solution with saturated $KMnO_4$ and those shown in FIG. 25B were obtained by the addition of concentrated sulfuric acid to a 0.1 ml aliquot of acidified bleach sample, diluted 20-fold (4.0 µmoles available chlorine). Since both the oxidation of chloride by permanganate and the formation of chlorine gas from hypochlorite by acidification tend to be slow at room temperature, the heat supplied by the hydration of sulfuric acid is a critical factor in controlling the kinetics of the reactions, and, hence, the shape of the peak profiles.

The reproducibility of the flame infrared emission procedures was studied by recording the signals from oxidizing eight 1.0-mL aliquots of a 5 mM NaCl standard. The relative standard deviation (RSD) was determined to be 3.34% for peak height measurements and 5.08% for peak area measurements. The difference in reproducibility between the peak height measurements and the peak area measurements most probably occurs in the trailing edge of the peak profile as discussed by Kubala et al, *Anal Chem.*, 1989, Vol. 61 pgs. 1841–1846.

Since the peak height measurements were consistently more reproducible for the standards and aqueous samples used in this study, peak height measurements were used exclusively. The root-mean-square signal-to-noise ratio ($SNR_{rms}$) was approximately 223:1 for the HCl signals obtained from the oxidation of the 5.0 mM NaCl standard.

Calibration curves were prepared by oxidizing 0.10 to 10 mM NaCl standards and were found to be linear (correlation coefficient of 0.9997). The linear regression equation for a typical calibration curve possessed a slope of 11.46 mm/mM and a y-intercept of −0.09 mm. The detection limit for $Cl^-$ with the flame infrared emission-chlorine system, defined as a concentration of $Cl^-$ producing a signal equivalent to twice the rms noise, was found to be 1.59 ppm ($4.49 \times 10^{-2}$ mM $Cl^-$). The detection limit for available $Cl_2$, based upon the $Cl^-$ calibration curve (and defined at twice the rms noise), was found to be 1.61 ppm ($2.26 \times 10^{-2}$ mM $Cl_2$).

Natural water and oil brine samples were used to evaluate the analytical performance of the flame infrared emission-chlorine system for the determination of aqueous chloride. The natural water samples included tap water from the Texas cities of Waco and Hewitt, surface waters from Lake Brazos, the Bosque and Brazos River, and brine samples from oil-bearing rock formations. The brine samples were obtained from the Van oil field located in Northeast Texas [Woodbine formation (975 m) and Nacitoch formation (366 m)] and were separated from the associated crude oil by slight heating (80° C.) and centrifugation. A 200-fold dilution of these brine samples was necessary in order to provide a concentration in the linear range of the calibration curve.

TABLE 3

COMPARISON OF CHLORIDE DETERMINED BY FLAME INFRARED EMISSION AND BY ARGENTOMETRIC TITRATION FOR SELECTED WATER AND OIL BRINE SAMPLES.

| Sample | Titration (ppm)[a] | Flame Infrared Emission | % Rel Error |
|---|---|---|---|
| Hewitt Tap | 61.4 ± 0.1 | 60.6 ± 2.5 | −1.30 |
| Waco Tap | 23.4 ± 0.1 | 25.1 ± 1.8 | +7.26 |
| Bosque River | 17.1 ± 0.4 | 15.2 ± 1.2 | −11.1 |
| Brazos River | 38.2 ± 0.5 | 35.0 ± 0.5 | −8.38 |
| Lake Brazos | 32.0 ± 0.2 | 30.6 ± 1.7 | −4.38 |
| Woodbine Brine | (41.4 ± 0.1) × 10³ | (43.0 ± 1.2) × 10³ | +3.86 |
| Nacitoch Brine | (17.3 ± 2.0) × 10³ | (17.0 ± 0.3) × 10³ | −1.73 |

[a]Average and standard deviation of 4 sample determinations.

Table 3 compares the chloride values determined by argentometric titration using potassium chromate as an indicator with chloride values obtained using the flame infrared emission detector. Each measurement in the table is an average of four replications. Although the tap water samples used in this study were chlorinated, the concentrations of available chlorine as determined by iodometric titration were below the detection limit of the flame infrared emission detector. As a result, no interference from available chlorine was encountered in the determination of chloride ion for the tap water samples used in this study. However, even if the sensitivity of the flame infrared emission system were improved to the point where available chlorine levels in tap water could be detected along with chloride using the flame infrared emission system, interference from available chlorine would be eliminated by the acidification and sample purging step prior to addition of the $KMnO_4$ solution.

As shown in Table 3, the precision of the results obtained with the flame infrared emission system is quite good (average relative standard deviation, RSD, 4.39%). The percent difference between the results obtained using the flame infrared emission system and those obtained by argentometric titration (Table 3) cannot be ascribed simply to inaccuracies in the flame infrared emission method because the titration method for chloride is subject to interference from such common ions as bromide, iodide, and phosphate. (This will be discussed more fully). It is interesting to note that for the surface water samples (Bosque River, Brazos River and Lake Brazos) the titration method gave results which were all higher than those obtained using the flame infrared emission system. High results obtained by argentometric titration may be indicative of interference from such ions as phosphate which are present in these surface waters. From Table 3, the average percent relative difference for the seven samples is 5.43%. The agreement between the results obtained with the flame infrared emission detector and the titration method is very good, considering that the titration method is not totally error free.

Three commercial bleach products were used to test the performance of the flame infrared emission system for the determination of available chlorine. Bleach samples were diluted 20-fold to give a concentration within the linear range of the flame infrared emission calibration curve.

TABLE 4

COMPARISON OF AVAILABLE CHLORINE DETERMINED BY FLAME INFRARED EMISSION AND BY IODOMETRIC TITRATION FOR SELECTED BLEACH SAMPLES.

| Sample | Titration (ppm)[a] | Flame Infrared Emission (ppm)* | % Rel Error |
|---|---|---|---|
| Bleach Brand X | (57.2 ± 0.9) × 10³ | (60.7 ± 0.8) × 10³ | +6.12 |
| Bleach Brand Y | (53.5 ± 0.1) × 10³ | (52.4 ± 0.7) × 10³ | −2.06 |
| Bleach Brand Z | (55.5 ± 1.2) × 10³ | (55.9 ± 1.6) × 10³ | +0.72 |

[a]Average and standard deviation of 4 sample determinations.

Table 4 compares the results obtained for available chlorine by iodometric titration with those obtained using the flame infrared emission detector and shows that the average precision obtained using the flame infrared emission detector is quite good (RSD 1.84%). Taking the iodometric titration as a reference method, the average relative error for the three bleach samples is 2.97%. The close agreement between available chlorine as determined by the flame infrared emission detector and as determined by iodometric titration demonstrates the feasibility of using chloride to prepare the flame infrared emission calibration curve.

Interferences with the flame infrared emission-chlorine analyzer can be classified into two major types: chemical and spectral. Spectral interferences in the flame infrared emission detector will occur whenever purgeable contaminants present in the sample are capable of existing as stable molecules or fragments at flame temperatures and emitting infrared radiation within the bandpass of the filter. Because of the specificity of infrared emission and the judicious selection of notch filters, however, the chance of severe interference (i.e., direct overlap) is not particularly likely.

A more subtle form of spectral interference can result from filter imperfections (or filter bleed). Interference filters of the type used in the flame infrared emission-chlorine analyzer have a small, but finite, transmittance at wavelengths well removed from the peak transmission wavelength. The filter used in this study, for example had a 0.1% transmittance in the vicinity of the 4.42 μm $CO_2$ emission band. While this transmittance seems small, optical leakage of the $CO_2$ band can produce measurable signals in the presence of large amounts of carbon-containing interferents.

Chemical interferences can occur with the flame infrared emission-chlorine analyzer in a number of ways, such as altering the oxidation process (in the case of chloride) or retarding the purging of chlorine ($Cl_2$) from the sample chamber. Thus, any concomitant which produces a volatile chlorine-containing compound that either does not burn readily in the flame or does not form HCl as a combustion product will depress the signal. Chemical interference can also occur if a non-volatile chlorine-containing compound is produced instead of $Cl_2$ or if a purgeable contaminant reacts with $Cl_2$ in the purge gas stream and reduces the amount of $Cl_2$ reaching the flame.

Bromide, iodide, and phosphate can introduce positive errors in the determination of chloride ion by argentometric titration. Since these anions can be present in natural waters at concentrations as high 1 mg/L [Br], 0.1 mg/L [I], and 0.4 mg/L [P] (Greenburg, A. E. et al., 1985; Manahan, S. E., 1979), the effect of these species as possible interferences in the determination of aqueous chloride using the flame infrared emission system was investigated.

To determine the extent to which these anions interfere with chloride determinations performed with the flame infrared emission detector, chloride determinations were repeated using 5 mM NaCl standards which had been spiked with bromide, iodide, and phosphate significantly greater than the maximum concentration expected for natural waters. The signals obtained from the spiked solutions were then compared to an unspiked 5 mM NaCl standard.

TABLE 5

COMPARISON OF FLAME INFRARED EMISSION
RESULTS WITH ARGENTOMETRIC TITRATION
FOR CHLORIDE DETERMINATION IN THE
PRESENCE OF SELECTED INTERFERENCES.

| Sample | Flame Infrared Emission (ppm)[a] | Titration (ppm)[a] |
|---|---|---|
| Blank[b] | 175 ± 7.30 | 175 ± 1.03 |
| Bromide[c] | 107 ± 2.26 | 195 ± 0.621 |
| Iodide[d] | 174 ± 4.32 | 193 ± 1.03 |
| Phosphate[e] | 176 ± 4.94 | 195 ± 2.69 |

[a]Average and standard deviation of 4 sample determination.
[b]5.00 mM (175 ppm) Cl⁻.
[c]5.00 mM Cl⁻, 0.595 mM Br⁻ (equivalent to 21.1 ppm Cl⁻).
[d]5.00 mM Cl⁻, 0.595 mM I⁻ (equivalent to 21.1 ppm Cl⁻).
[e]5.00 mM Cl⁻, 0.223 mM $PO_4^{-3}$ (equivalent to 20.6 ppm Cl⁻).

Figure 26:
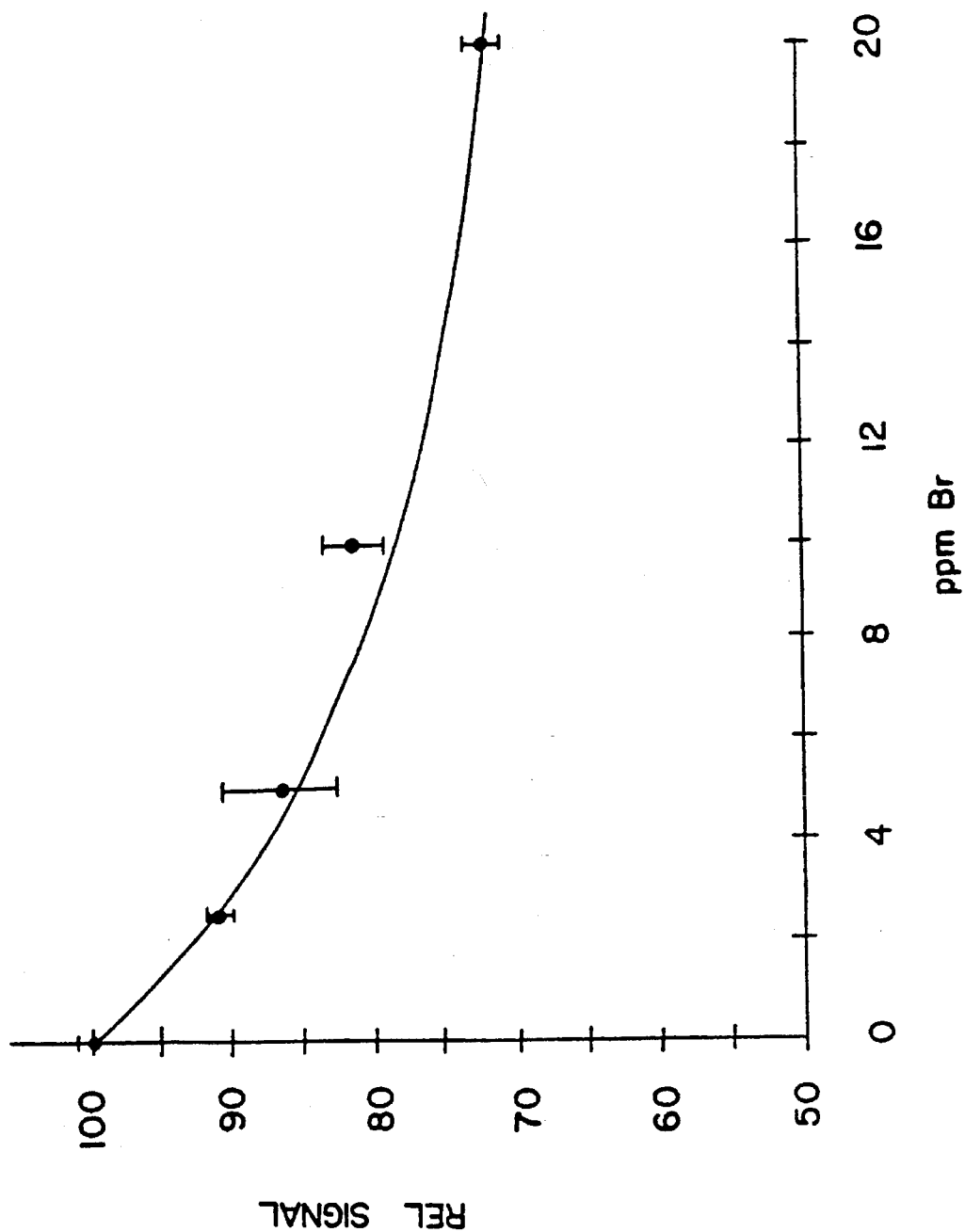
FIG. 26 graphically illustrates the HCl flame infrared emission signal versus bromide concentration.

Table 5 shows that the presence of bromide, iodide, or phosphate resulted in a large positive error in the argentometric titration method, with the apparent chloride concentration being given by the sum of the true chloride concentration (175 ppm) and the concentration of the interfering anion, expressed at its chloride equivalent (about 21 ppm). Although no observable difference in peak height occurred in the presence of iodide and phosphate for the flame infrared emission detector (Table 5), a 27% suppression of the HCl signal occurred in the presence of bromide. In order to quantify this effect, 5 mM NaCl solutions having different bromide concentrations were prepared and analyzed. A plot of signal versus bromide concentration for 1.0 mL aliquots of 5.00 mM NaCl spiked with NaBr (FIG. 26), although not linear, did indicate an increasing suppression of the HCl signal as bromide ion concentration was increased.

While no attempt was made to identify the exact mechanism responsible for bromide interference in the chloride determination using the flame infrared emission system, the factors involved are almost certainly chemical in nature. The oxidation chemistry of the halides is complicated by the large number of higher oxidation states available to the halogens, and half-cell potentials provide only an approximate guide because the kinetics of the reactions are often slow. However, permanganate and bromine half-cell potentials (adjusted for conditions of the analysis, i.e., approximately 11 molar acid) indicate that in the presence of excess permanganate, bromide can be oxidized to both $Br_2$ and $BrO_3^-$. While bromate would remain in solution, any elemental bromine would be expelled along with elemental chlorine during the purging process. Since the molar solubilities of both $Cl_2$ and $Br_2$ are relatively high [$9.1 \times 10^{-2}$ moles/L and 0.21 moles/L at 25° C., respectively], both would probably dissolve to some extent in the moisture which condenses between the chlorine generation chamber and the burner. Introduction of chlorine into bromine water under neutral conditions is known to result in the formation of bromate ion, $BrO_3^-$, and chloride ion,

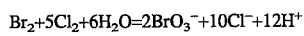

Any chloride ion which is not swept out of the condensed moisture as HCl during the 15–20 second time period required to record the flame infrared emission signal would contribute to a negative interference.

In the case of iodide, half-cell potentials suggest that reaction with excess permanganate is even more likely to produce higher oxidation states [iodate and possibly periodic acid] which would remain in solution. Moreover, any $I_2$ that might form is also relatively insoluble in water [$1.3 \times 10^{-3}$M] and is much less likely to be purged along with $Cl_2$ in sufficient quantities to act as an interferant. Further support for the proposed mechanism for bromide interference is the observation that increased corrosion and clogging of the stainless steel capillary tube (used to introduce the sample into the burner) occurred during the analysis of samples containing bromide. The presence of these deposits also results in some loss of precision for the chloride results as shown in Table 5.

One method of dealing with bromide interference in the determination of chloride by argentometric procedures is to pretreat the sample using iodate ion in acid solution. The reaction

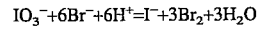

selectively produces bromine, which can be expelled by boiling the solution, and iodide ion which is not expected to interfere in the flame infrared emission procedure (Table 5). The feasibility of using iodate to eliminate bromide interference in the flame infrared emission analyzer was investigated, and the results are shown in Table 5.

TABLE 6

COMPARISON OF FLAME INFRARED EMISSION
RESULTS FOR CHLORIDE DETERMINATION IN
THE PRESENCE OF BROMIDE FOR
SEVERAL SAMPLE PRETREATMENT METHODS.

| Sample | Flame Infrared Emission (ppm)[a] | % Difference[b] |
|---|---|---|
| Chloride[c] | 175 ± 9 | 0 |
| Chloride/Iodate[d] | 173 ± 10 | −1.1 |
| Chloride/Bromide[e,f] | 168 ± 10 | −4.0 |
| Chloride/Bromide[e,g] | 166 ± 11 | −5.1 |
| Chloride/Bromide[e,h] | 94 ± 7 | −46.3 |

[a]Average and standard deviation of 4 sample determinations.
[b]Percent difference compared to chloride (175 ppm) in the absence of bromide.
[c]5.00 mM (175 ppm) Cl⁻.
[d]5.00 mM Cl⁻, 4.70 mM $KIO_3$.
[e]5.00 mM Cl⁻, 4.70 mM $KIO_3$, 0.60 mM Br⁻.
[f]Bromine expelled by boiling the solution prior to analysis.
[g]Bromine expelled by purging in the sample chamber prior to analysis.
[h]Bromine and chlorine purged together during analysis.

As shown in Table 6, pretreatment of 1.0 mL of a 5 mM chloride solution with $KIO_3$ and permanganate did not alter the flame infrared emission results for chloride within experimental error. However, the presence of both iodate and bromide ion in the sample resulted in a 46.3% suppression of the flame infrared emission signal, compared with chloride solutions containing no bromide. This negative interference is even greater than the 27% suppression observed for bromide-containing samples which were not pretreated with iodate (Table 6), and may indicate that $Br_2$ makes up a greater percentage of the bromide oxidation products when iodate is added prior to treatment by permanganate. In contrast, considerably less suppression of the HCl signal occurred when the bromide-containing solution was pretreated with iodate and then boiled for 10 minutes before introduction into the purge tube (−4.0%) or pretreated with iodate and then purged directly in the sample chamber (−5.1%) to expel bromine prior to addition of permanganate. (Again, precision was somewhat degraded due to deposits which formed in the capillary tube during the analysis). These results, although preliminary, indicate that aqueous chloride solutions can be successfully pretreated with iodate to remove bromide interference in the flame infrared emission procedure.

As discussed previously, the flame infrared emission-chlorine procedure is capable of detecting available $Cl_2$ in aqueous samples. Since many municipalities add $Cl_2$ or a chlorine-containing compound (chloramines) to tap water for disinfection, available chlorine may interfere in the determination of aqueous chloride. Thus, the initial purging step of the acid/sample mixture before oxidation of the aqueous chloride is useful in removing any available $Cl_2$ that may be present in the water sample.

Carbon dioxide can be present in the flame as a result of purging $CO_2$ from an acidified carbonate-containing solution as in Kubala, et al, Anal. Chem., 1989, Vol 61. pgs. 1841–1846 or combusting a purgeable organic compound as in Example 1. Because the transmission characteristics of the 3.8 μm HCl bandpass filter allow for slight filter bleed in the region of the $CO_2$ infrared emission band [centered at 4.42 μm], carbonates and purgeable organics could act as spectral interferences in the determination of aqueous chloride and available chlorine. In order to determine if this potential interference is detected by the flame infrared emission-chlorine system, 2-μL injections of cyclopentane were introduced into the purge tube in a manner similar to the procedure outlined for the determination of available chlorine (cyclopentane added to hot acid). Although the results were not quantified, they did indicate that a slight, but detectable amount of filter bleed from the $CO_2$ emission band occurred in the transmission of the 3.8 μm HCl optical bandpass filter. Thus, in chloride determination by the flame infrared emission system, the procedure sequence allowing the sample to degas prior to addition of permanganate is important for removing carbonate and volatile organic interferences before the chlorine generation step.

Other possible interferences in the flame infrared emission-chlorine method for chloride are those species that are not purged from solution, but are oxidized to $CO_2$ under the conditions of the flame infrared emission procedure. Permanganate, however, is not a sufficiently strong reagent to oxidize the majority of organic compounds to $CO_2$, and with the exception of a few species such as oxalates and oxalic acids, non-volatile inorganic or organic species are not expected to produce a chemical interference of this type.

The flame infrared emission detection system described in this experiment has been shown to be a sensitive, reproducible, accurate, and direct means of determining chloride in water and available chlorine in liquid bleach. It is easy to use and requires only a one-milliliter sample for each determination. In its present stage of development, the time required for signal acquisition from a sample is 3.5 minutes from the sample injection to purge-tube disconnection and clean up. The system is easily amenable to automation, and a multiple purge-tube version is envisioned.

Although only aqueous chloride and liquid bleach samples were investigated, it is possible to apply the flame infrared emission method to the determination of chlorine in any sample which can be pretreated to form elemental chlorine or hydrogen chloride in the sample chamber or contains purgeable chlorine-containing compounds which can be combusted to hydrogen chloride in the flame. Thus, determination of such species as chlorites, chloramines, chlorine dioxide and volatile organic chlorides is feasible. A special advantage of the flame infrared emission method is its lack of interference from iodide and phosphate, two ions which cause large positive errors in the determination of chloride by argentometric titration. The interference caused by bromide ion in the flame infrared emission method should be eliminated by sample pretreatment using iodate.

EXAMPLE 5

Figure 27:
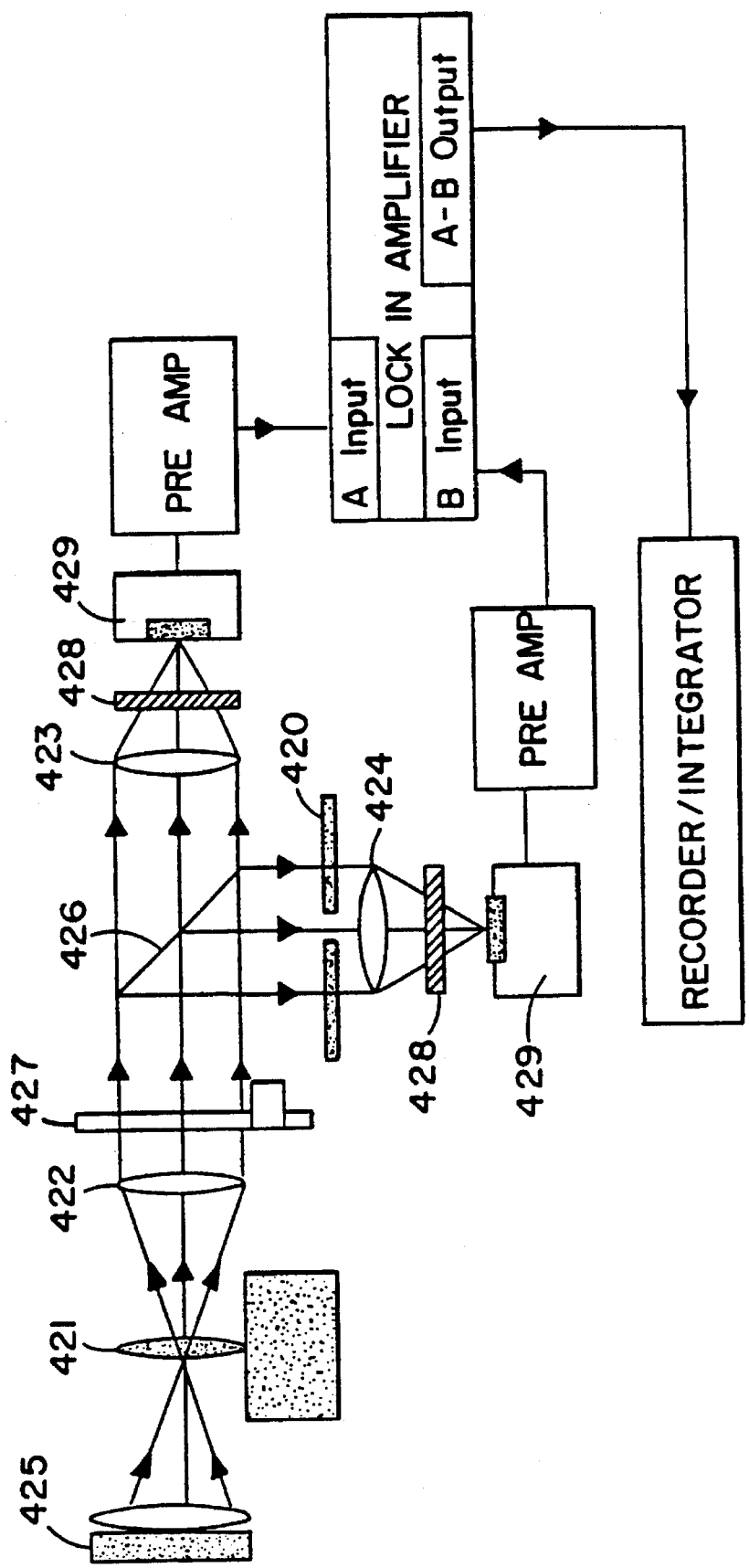
FIG. 27 schematically illustrates the dual channel system of Example 5.

The schematic layout for the dual channel flame infrared emission detector is shown in FIG. 27. The detection system consists of an optical dual channel module, followed by the electronic signal processing module.

The dual channel optical arrangement is made up of a flame excitation source 421 (Hydrogen/air combustion flame), collimating lens 422, focusing lenses 423 and 424, mirror 425, zinc selenide beam splitter 426, mechanical light beam chopper 427 (for signal modulation), and optical band pass filters 428 (for spectral band isolation).

The light from the source 421 is collimated by a calcium fluoride lens 422 of focal length 5 cm (P#43150, Oriel Corporation, Stratford, Conn.), and the mirror 425 of focal length 2.5 cm (P#44350, Oriel Corporation, Stratford, Conn.). The collimated radiation is then modulated at a frequency of 570 Hz by a mechanical light beam chopper 427 (designed and machined locally in this lab). The modulated radiation is then passed through a zinc selenide beam splitter 426 (P#45360, Oriel Corporation, Stratford, Conn.), which serves the role of a beam splitter dividing the radiation in two portions. Each portion of the divided radiation is then focussed onto a 1×5 mm lead selenide detector 429 (P#P791, Hamamatsu Corporation, Bridgewater, N.J.) by calcium fluoride lenses 423 and 424 of focal length 5 cm (P#43150, Oriel Corporation, Stratford, Conn.). Optical band pass filters 428 were placed in front of the detectors for isolating the spectral bands of interest. The filters 428 used were (1) 3.0±0.03 µm narrow band pass filter (P#58160, Oriel Corporation, Stratford, Conn.), (2) 4.4±0.03 µm narrow band pass filter (P#58300, Oriel Corporation, Stratford, Conn.), (3) 3.8±0.03 µm narrow band pass filter (P#58230, Oriel Corporation, Stratford, Conn.), (4) 2.35±0.01 µm narrow band pass filter (P#NB-2350-052-B Spectrogon, Secaucus, N.J.), (5) 2.5±0.05 µm short pass filter (P#SP-2550-S Spectrogon, Secaucus, N.J.).

One half of the divided optical path serves as the reference channel for monitoring the source background fluctuations, and the other half as the analytical channel for monitoring the analytical signals of interest. The 3.0 µm filter was placed in the reference channel to monitor and compensate for the background fluctuations in the flame due to $H_2O$ emission from the flame. Depending on the desired analyte, the 4.4 µm notch filter (to isolate the $CO_2$ emission band), the 3.8 µm notch filter (to isolate the HCl band), or 2.35 µm notch filter in combination with the 2.5 µm short pass filter (to isolate the HF band) could be placed in the analytical channel. The additional short pass filter was necessary, to effectively isolate the HF band from the strong interference band at 3.0 µm due to background emission from $H_2O$ present in the flame.

Figure 28:
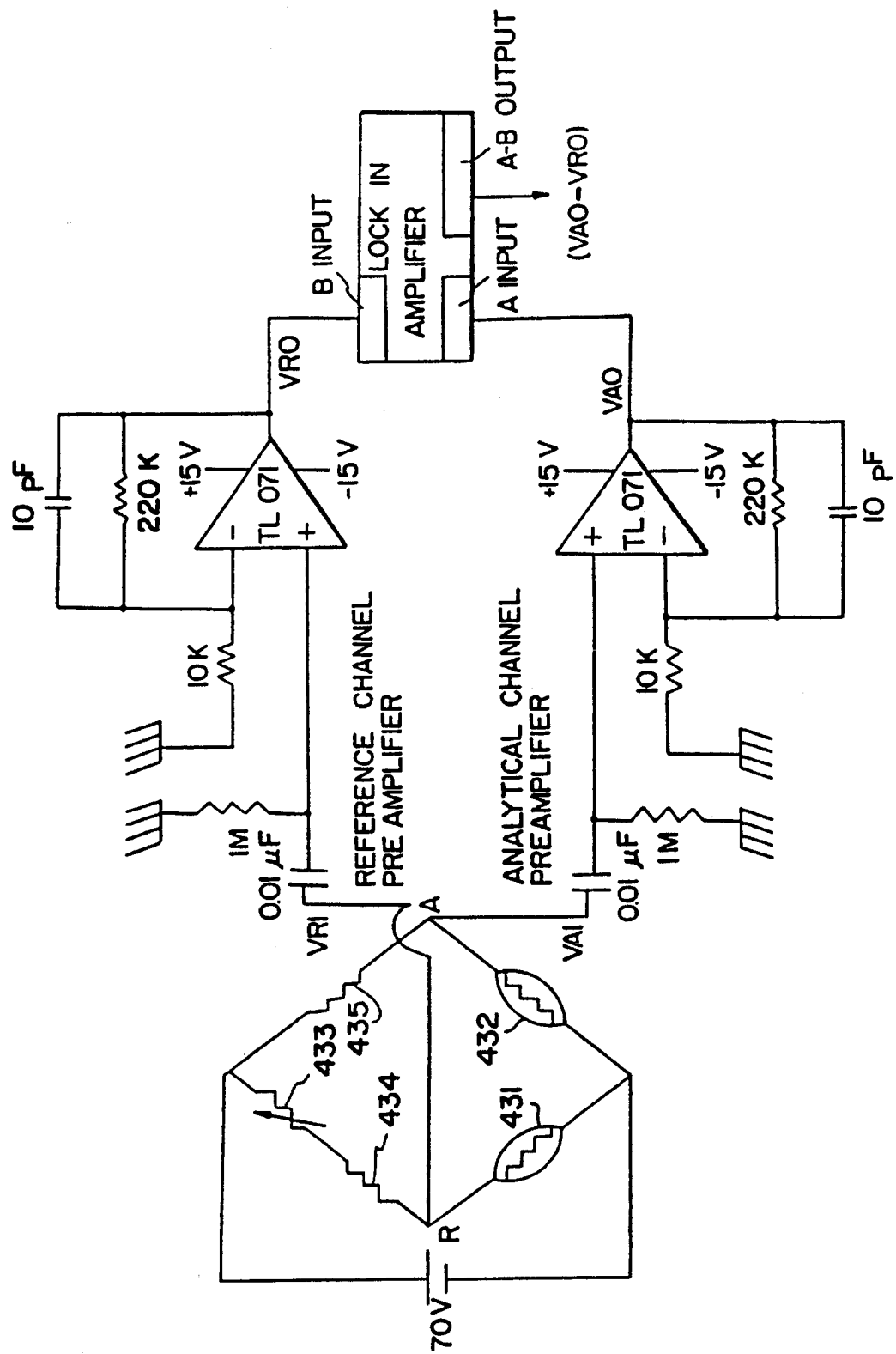
FIG. 28 schematically illustrates the electronic signal processing module of the dual channel system with optical attenuation.

The pre-amplifier circuit configuration for the dual channel system is shown in FIG. 28. The lead selenide detectors 431 and 432 were biased at +70 volts from a regulated dc power supply (P#6516, Hewlett Packard, Avondale, Calif.). The biasing circuit was tied together to the common power supply to achieve the classical Wheatstone bridge configuration. The value of the matching load resistors (300k) 434 and 435 for biasing the lead selenide detectors were chosen based on the manufacturer's specification sheet. A 20K ohm multiturn trimmer potentiometer 433 was connected in series with the resistor 434, which along with the detector 431 constitute the reference arm of the Wheatstone bridge network. The potentiometer 433 was used to fine tune the zero adjustment of the Wheatstone bridge to achieve an accurate balance condition. The voltages, $V_{Ri}$ and $V_{Ai}$ developed at the junctions R and A respectively were amplified separately by the pre-amplifier circuits. The pre-amplifier circuit configuration of the reference and analytical channels are identical in all respects (in terms of the values of the resistor and capacitors, and the operational amplifiers used). A BIFET operational amplifier (TL 071, Texas instruments, Dallas, Tex.) was used. The operational amplifiers were powered from a standard regulated ±15 V dual dc power supply (P#2718, Heath Co, Benton Harbor, Minn.). The pre-amplifier output $V_{Ro}$ and $V_{Ao}$ were then connected separately to the B and A input of the lock-in amplifier (Ithaco, 3962 single phase lock-in amplifier, Ithaca, N.Y.). The differential input mode (A-B) of the lock-in amplifier was chosen for operation. Under these conditions the output of the lock-in amplifier is also the differential output, i.e. $V_{Ao}-V_{Ro}$.

The following represent typical operating conditions for the dual channel system. With just the flame background seen by both channels, the signal from the analytical channel (with the appropriate band pass filter in place) was connected to the A input of the lock-in amplifier which was operated in the single ended input mode. After proper phase setting and time constant adjustment, the approximate value of the signal was recorded. The analytical channel signal was disconnected from the lock-in amplifier input and the reference channel signal was connected. The reference channel signal level was approximately 50 times greater than the analytical channel signal level. The signal level to the reference channel was attenuated optically with an iris diaphragm 420 placed in front of the lens 424. The aperture width of the iris was adjusted until the signal level in the reference channel was approximately the same as in the analytical channel. The analytical channel signal was then re-connected back to the A input of the lock-in amplifier and the reference channel signal was then connected to the B input of the lock-in amplifier. The differential input mode (A-B) of the lock-in amplifier was chosen for operation. The aperture width was then adjusted further until the output of the lock-in amplifier was approximately zero. Finer zero adjustments were made with the help of the trimmer potentiometer 433. The output of the lock-in amplifier was connected to a recorder/integrator (P#HP3394A, Hewlett Packard, Avondale, Calif.) for subsequent data processing.

A Shimadzu Gas chromatograph (model GC-8A, Shimadzu Instrument Inc., Columbia, Md.) with a thermal conductivity detector and temperature programming capability was used throughout this work. The outlet of the column was interfaced to the burner body of the flame infrared emission detector by the method already described (Hudson and Busch, 1988). The design and construction of the burner are as described (Hudson and Busch, 1988). The stainless steel capillary interface tube was wrapped with a heating tape and the temperature of the heating tape was maintained at 250° C. This was necessary to prevent the column effluent from condensing in the interface tube. The capillary burner head supported a hydrogen-air combustion flame. The $H_2$ and the air flow rates to the burner were regulated by means of standard flow meters (P#3227-20 (for hydrogen) and P#3227-26 (for air), Cole Parmer Company, Chicago, Ill.). The gas chromatographic column used throughout this work was a 6 ft×⅛" SP alloy column packed with carbopack-B and 5% Fluorcol. (P#12425, Supelco Inc., Bellafonte, Pa.). This column is specially designed for separation of fluoro and chloro carbons. Helium was used as the carrier gas throughout and a flow rate of 30 mL/min was used. The liquid samples were introduced into the gas chromatograph by means of standard Hamilton microliter syringes. All the optical components were mounted on aluminum blocks designed and machined locally. The aluminum mounts were painted flat black to minimize stray radiation and reflections reaching the detector. A shield made of aluminum and painted flat black on both the inside and the outside was placed around the burner to minimize flame flicker due to air currents from the atmosphere and the chopper blade. All experiments were performed after a 30 minute warm-up period to allow for the stabilization of electronic components and lead selenide detector response.

Preliminary optimization studies were undertaken to optimize and evaluate the performance characteristics of the dual channel system. The parameters chosen for optimization were (a) selectivity ratio and (b) minimum detectable quantity or detection limits. These are the two most important figures of merit of any selective detection system, since a given selective detection system should have a high selectivity towards a species of interest and at the same time should be able to detect very small quantities of that species. The experimental variables that were considered to have a significant effect on these two parameters were (a) detector bias voltage, (b) the optical filter in the reference channel for background compensation, and (c) the method of balancing the Wheatstone bridge network.

The experiments were conducted with Freon-113 and pentane as representative analytes. Freon-113 was used to evaluate the response of the system in the fluorine- and chlorine-selective modes of operation. Pentane was used as the hydrocarbon comparison standard for evaluation of selectivity ratios of the fluorine and the chlorine modes of operation, since pentane does not produce any HCl or HF on combustion. Typical selectivity ratios and detection limit calculations are shown in Table 7 for the fluorine selective mode of operation.

TABLE 7

|  | Subtracted Mode | Unsubtracted Mode |
|---|---|---|
| VOLUME OF FREON-113 INJECTED (ml) | 0.001 | 0.001 |
| VOLUME OF PENTANE INJECTED (ml) | 0.010 | 0.001 |
| SIGNAL FOR FREON-113 (mm) | 123.000 | 113.000 |
| SIGNAL FOR PENTANE (mm) | 4.000 | 17.000 |
| RMS NOISE (mm) | 0.100 | 1.000 |
| (S/N) Ratio (FOR FREON-113) | 1225.000 | 113.000 |
| DENSITY OF FREON-113 (gm/ml) | 1.575 | 1.575 |
| PEAK WIDTH FOR FREON-113 (sec) | 24.000 | 24.000 |
| DETECTION LIMIT FOR FREON-113 (ng/sec) | 107.000 | 1160.000 |
| SELECTIVITY RATIO | 305.000 | 7.000 |

In Table 7 the detection limit for Freon-113 was calculated from the following equation $$\frac{2x \ V_{FC\text{-}113} \times d_{FC\text{-}113} \times 10^9}{(S/N)\text{Ratio} \times \text{Peak Width}}$$

wherein V is volume (mL) injected and d is density (g/mL). The selectivity ratio used here was the ratio of the signal for Freon-113/signal for pentane.

Figure 29A:
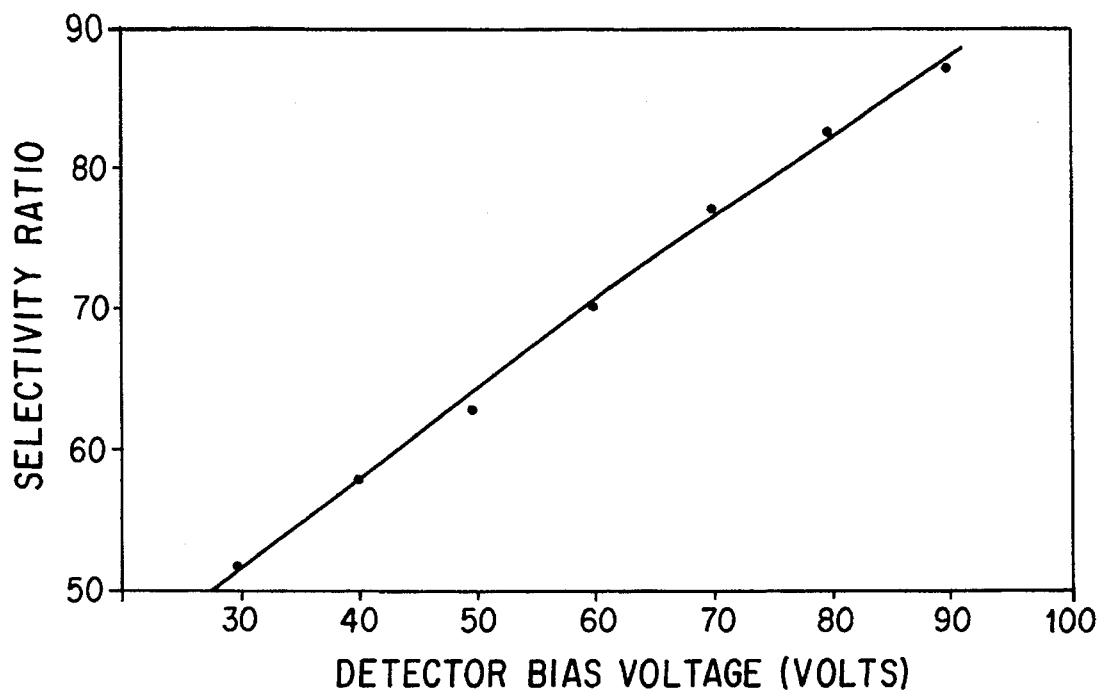
FIGS. 29A and 29B graphically illustrate (18A) the selectivity ratio versus detector bias voltage and (18B) the detection limit concentration versus detector bias voltage for the dual channel system.
Figure 29B:
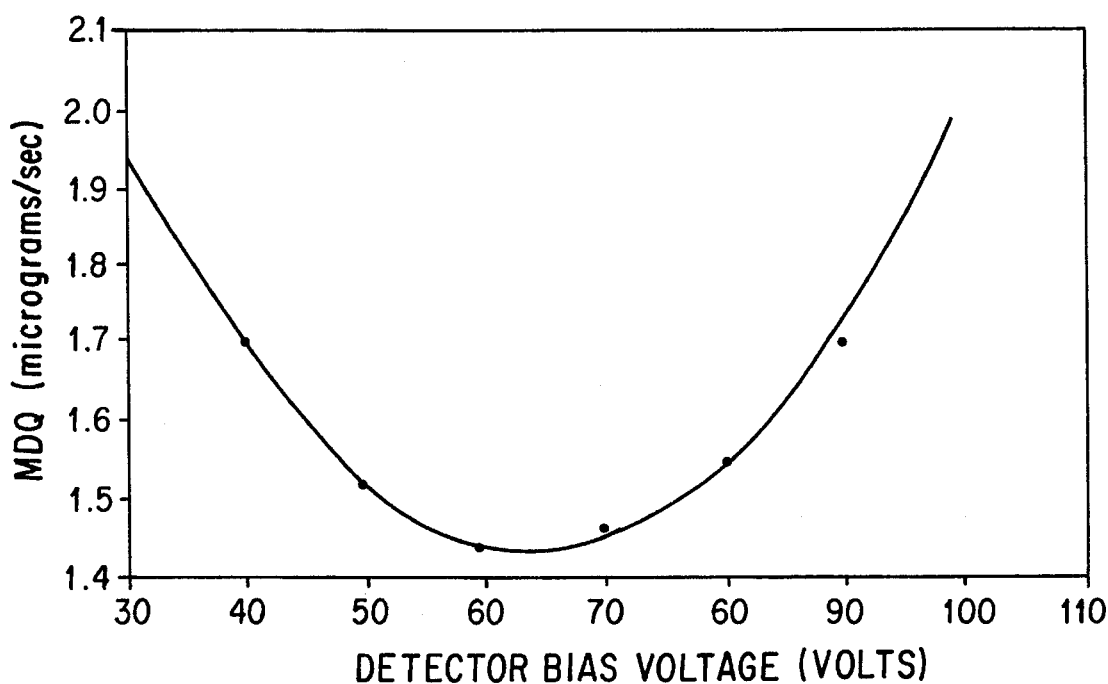

A study of the effect of detector bias voltage on the selectivity ratio and detection limits was carried out. The 4.4 µm filter was placed in the reference channel for background compensation and the 2.35 & 2.50 µm filters were placed in the analytical channel to isolate the HF bands. The chromatographic conditions were the same as described above. The experiments were carried out at 180° C. (isothermal) and one and ten microliter sample sizes were used. The results are summarized in Table 8, and graphically illustrated in FIGS. 29A and 29B.

TABLE 8

| NO | DETECTOR BIAS VOLTAGE (VOLTS) | MINIMUM DETECTABLE QUANTITY (micrograms/sec) | SELECTIVITY RATIO |
|---|---|---|---|
| 1 | 30 | 1.95 | 52 |
| 2 | 40 | 1.70 | 58 |
| 3 | 50 | 1.52 | 63 |
| 4 | 60 | 1.44 | 70 |
| 5 | 70 | 1.46 | 77 |
| 6 | 80 | 1.55 | 83 |
| 7 | 90 | 1.70 | 87 |

The results indicate that even though the selectivity ratio (fluorine/carbon) increases linearly with increasing detector bias voltage the minimum detectable quantity (MDQ) of Freon-113 shows a distinct minimum around 70 volts, and a further increase in the bias voltage leads to poorer detection limits. Based on these results a detector bias voltage of 70 volts was chosen as an optimum value for further experiments.

A study to evaluate the relative efficiency of the reference channel filters to compensate for the source background fluctuations was carried out. The two filters compared were the 3.0 µm filter (to compensate for source background fluctuations due to $H_2O$ emission in the flame), and the 4.4 µm filter (to compensate for the $CO_2$ emission resulting from the combustion). The results of the filter comparison are summarized in Table 9.

TABLE 9

| | SUBTRACTED MODE | | UNSUB-TRACTED MODE |
|---|---|---|---|
| FILTER COMPARISON | 3.0 (micron filter) | 4.4 | |
| 1. SELECTIVITY RATIO | | | |
| a. Fluorine Mode | 305 | 81 | 7 |
| b. Chlorine mode | 175 | 114 | 6 |
| 2. DETECTION LIMIT | | | |
| nanograms / sec | | | |
| a. Fluorine Mode | 107 | 1150 | 1160 |
| b. Chlorine Mode | 375 | 1440 | 1010 |
| c. Carbon Mode | 112 | — | 127 |

These results clearly indicate that with the 3.0 µm filter in the reference channel, both selectivity ratio and detection limits are far better than with the 4.4 µm filter. The corresponding results for the unsubstracted mode of operation are given for the sake of comparison. With the 4.4 µm filter in the reference channel, even though the selectivity ratio is better than that in the unsubtracted mode, the detection limits are slightly worse, but with the 3.0 µm filter in the reference channel both the selectivity ratio and the detection limits are substantially better than the corresponding unsubtracted mode. Based on these results the 3.0 µm filter was chosen for background compensation in further studies.

The Wheatstone bridge configuration for implementing the background compensation has already been discussed. The bridge balancing condition was actually achieved by two different methods and the relative performances of these methods were evaluated with the two parameters i.e. selectivity ratio, and detection limits. The two methods compared are (1) optical attenuation and (2) electronic attenuation. A brief discussion of these two methods is presented in the following section.

The Wheatstone bridge network used for the optical attenuation method is shown in FIG. 28. This method has already been discussed. The bridge balance condition was achieved (under the flame background conditions) by optically attenuating the signal intensity in the reference channel by means of an iris diaphragm, until it approximately equaled the signal in the analytical channel. Under these conditions any fluctuations in source intensity common to both channels would mutually cancel each other and only signals due to species of interest would appear in the analytical channel.

The electronic attenuation method could further be classified into (1) an adjustable load resistor method and (2) an adjustable pre-amplifier gain method.

Figure 30:
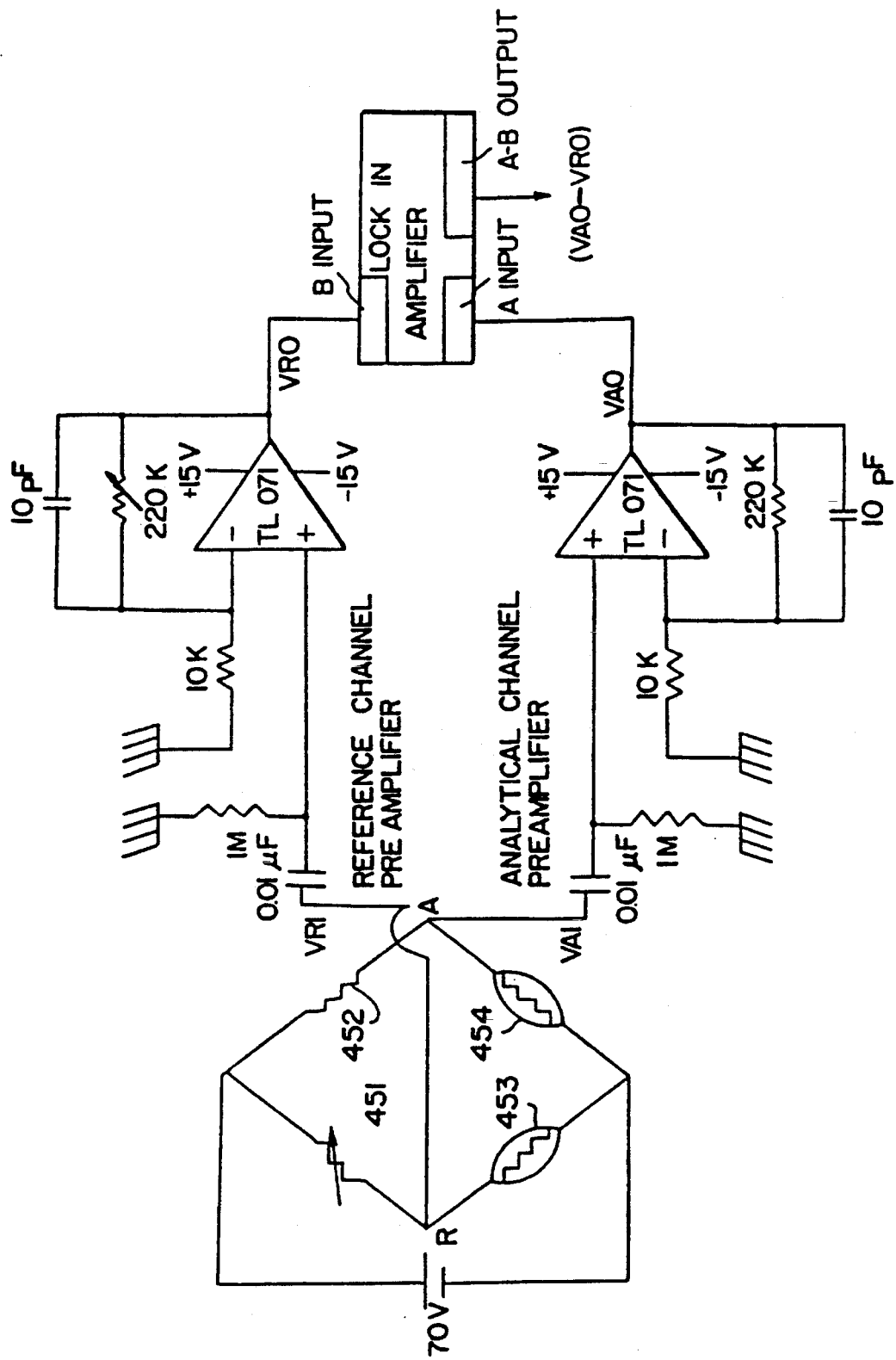
FIG. 30 schematically illustrates the electronic signal process module of the dual channel system with an adjustable load resistor.

The Wheatstone bridge network used in the adjustable load resistor method is shown in FIG. 30. In this method the bridge balance (under the flame background conditions) was achieved by adjusting the value of the resistance of the load resistor 451 on the reference arm of the bridge. The load resistor 451 and the lead selenide detector 453 constitute the reference arm of the Wheatstone bridge. The load resistor 451 on the reference channel is a multiturn trimmer potentiometer whose value could be adjusted until the potential at points R and A are approximately equal. Under these conditions the signal levels $V_{Ri}$ and $V_{Ai}$ are equal and the differential output $(V_{Ao}-V_{Ro})$ is zero.

Figure 31:
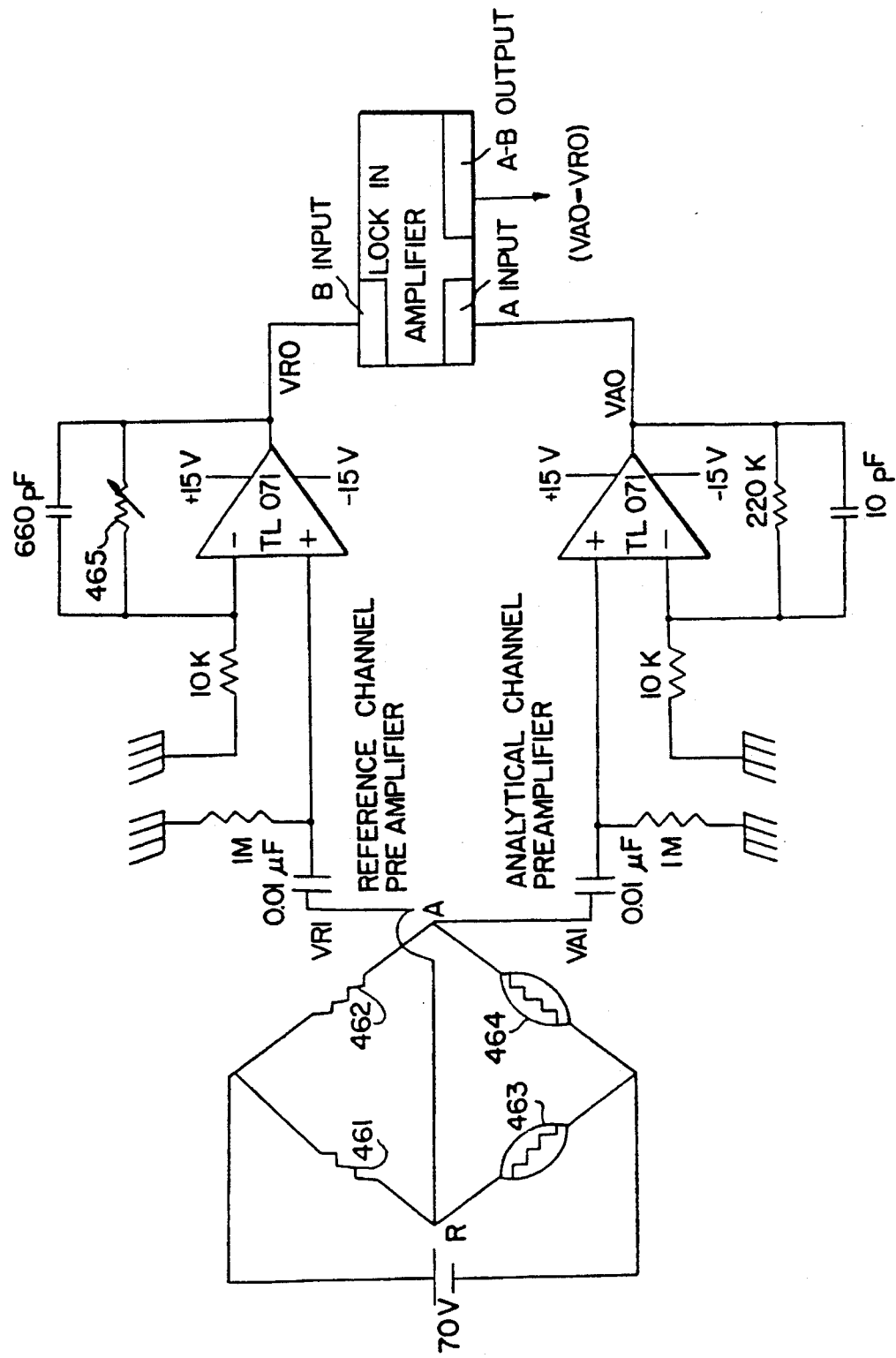
FIG. 31 schematically illustrates the electronic processing module of the dual channel system with an adjustable preamplifier gain.

The Wheatstone bridge network used in the adjustable preamplifier gain method is shown in FIG. 31. It is essentially the same as used in the previous method, shown in FIG. 30, the only difference being that the signal levels $V_{Ao}$ and $V_{Ro}$ are made equal by adjusting the gain of the reference preamplifier circuit with a gain control resistor 465. The gain of the reference channel circuit was adjusted until the signal level $V_{Ro}$ became equal to $V_{Ao}$. Under these condition the differential output $(V_{Ao}-V_{Ro})$ is zero.

The results obtained for these three methods are summarized in Table 10.

TABLE 10

| SUBTRACTED MODE/ | OPT. ATTENU-ATION/ | ELECTRONIC ATTENUATION Load Resistor/Preamp Gain |
|---|---|---|
| 1. Selectivity Ratio | | |
| a. Fluorine Mode | 726 | 766/305 |
| b. Chlorine Mode | 238 | 282/175 |
| 2. Detection Limits (nanograms/sec) | | |
| a. Fluorine Mode | 96 | 547/107 |
| b. Chlorine Mode | 116 | 850/375 |
| c. Carbon Mode | 22 | 26/122 |

The corresponding results for the unsubtracted mode of operation are given in Table 11.

TABLE 11

| UNSUBTRACTED MODE/ | OPT. ATTENU-ATION/ | ELECTRONIC ATTENUATION Load Resistor/Preamp Gain |
|---|---|---|
| 1. Selectivity Ratio | | |
| a. Fluorine Mode | 16 | 6/9 |
| b. Chlorine Mode | 9 | 9/6 |
| 2. Detection Limits (nanograms/sec) | | |
| a. Fluorine Mode | 1130 | 2620/1160 |
| b. Chlorine Mode | 1190 | 1650/1010 |
| c. Carbon Mode | 231 | 242/127 |

The results indicate that the optical attenuation method offers the optimum values of detection limits and selectivity ratio, and based on the results this was the method of choice for balancing the bridge network in all the subsequent experiments. The preliminary optimization studies lead to the choice of the following factors for subsequent experiments:

a) A detector bias voltage of +70 volts, b) A 3.0 μm filter in the reference channel for background compensation, and c) The optical attenuation method to balance the bridge network.

Table 12 summarizes the relative performance of the dual channel system in the subtracted mode to that of the unsubtracted mode obtained under the optimum conditions mentioned above.

TABLE 12

| | SUBTRACTED MODE | UNSUBTRACTED MODE |
|---|---|---|
| 1. Selectivity Ratio | | |
| a. Fluorine Mode | 726 | 16 |
| b. Chlorine Mode | 238 | 9 |
| 2. Detection Limits (nanograms/sec) | | |
| a. Fluorine Mode | 96 | 1130 |
| b. Chlorine Mode | 116 | 1190 |
| c. CARBON MODE | | |
| 1. For Freon-113 | 22 | 231 |
| 2. For Pentane | 2 | 265 |

The response for pentane in the carbon mode is included for the sake of comparison. In the unsubtracted mode the detection limit for pentane and for Freon-113 are about the same. However, in the subtracted mode, the detection limit for pentane is about an order of magnitude better than that for Freon-113.

Figure 32C:
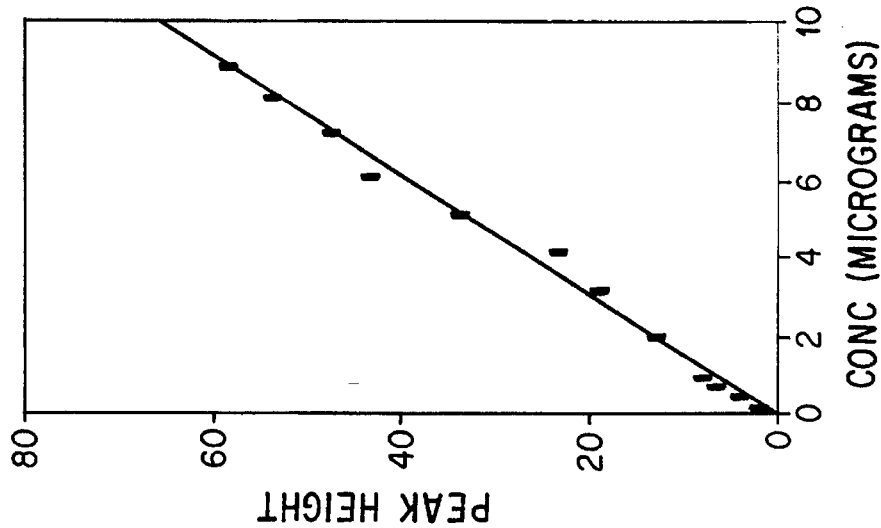
FIGS. 32A to 32C graphically illustrate peak height versus concentration for the dual channel system in the fluoride sensitive, chloride sensitive and carbon sensitive modes.
Figure 32B:
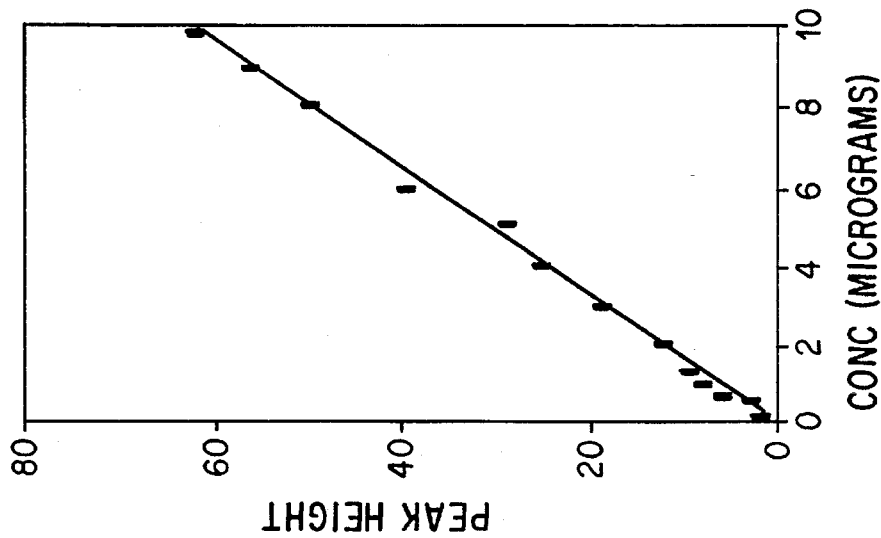
Figure 32A:
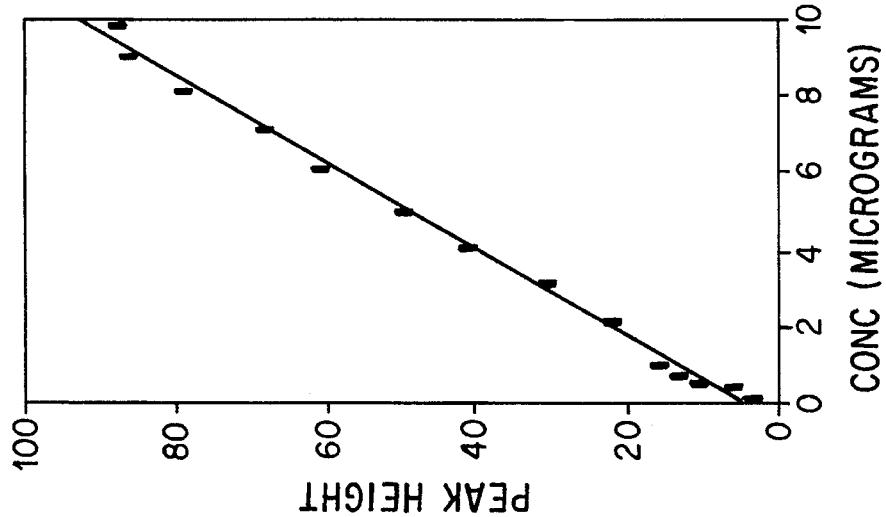

The response characteristics of the dual channel system in the three different selective modes (carbon, chlorine, fluorine) were evaluated. Calibration standards of Freon-113 in dichloromethane were prepared in the concentration range from 0.1 to 10 micrograms. The calibration standard of Freon-113 was chromatographed at 180° C. (isothermal), on a Carbopack-B (5% Fluorcol) column, with helium as the carrier gas at a flow rate of 30 ml/min. The chromatographic peak height was plotted as a function of amount of Freon-113 injected. The results are summarized in Table 13 and the calibration plots are shown in FIGS. 32A–32C. The calibration plots indicate excellent linearity in the detector response for the amounts of Freon-113 injected.

TABLE 13

| | | Peak Height (mm) | | |
|---|---|---|---|---|
| # # | Amount of Freon-113 injected (micrograms) | Fluorine Mode | Chlorine Mode | Carbon Mode |
| 1 | 0.212 | 1.0 | 0.9 | 4.0 |
| 2 | 0.430 | 1.8 | 1.6 | 6.0 |
| 3 | 0.630 | 3.5 | 3.7 | 10.0 |
| 4 | 0.612 | 5.0 | 4.7 | 12.0 |
| 5 | 1.013 | 7.0 | 6.0 | 15.2 |
| 6 | 2.152 | 13.0 | 12.0 | 23.0 |
| 7 | 3.130 | 19.0 | 19.0 | 32.0 |
| 8 | 4.060 | 24.0 | 25.0 | 42.0 |
| 9 | 5.074 | 34.0 | 29.0 | 40.0 |
| 10 | 6.093 | 43.0 | 39.0 | 60.0 |

TABLE 13-continued

| # # | Amount of Freon-113 injected (micrograms) | Peak Height (mm) | | |
|---|---|---|---|---|
| | | Fluorine Mode | Chlorine Mode | Carbon Mode |
| 11 | 7.067 | 47.0 | 44.0 | 68.0 |
| 12 | 8.092 | 54.0 | 50.0 | 78.0 |
| 13 | 9.035 | 60.0 | 56.0 | 86.0 |
| 14 | 9.866 | 66.0 | 62.0 | 88.0 |

Based on the results obtained for the preliminary optimization of the dual channel system, it can be safely concluded that use of background subtraction to compensate for source fluctuations leads to a much superior detection system in comparison to the unsubtracted mode of operation. This conclusion is exemplified by the two parameters: (a) selectivity ratio and (b) detection limits. Further investigations were carried out to test and evaluate the performance of the dual channel system and see how well the these improvements translate in a real-time analysis situation. A gas chromatographic separation of a chlorofluorocarbon mixture was chosen for this purpose. The essential idea behind this approach was that in a mixture of chlorofluorocarbons and hydrocarbons chromatographed under an element selective mode, only the compounds containing the given element of interest would respond while others would be virtually excluded. A synthetic mixture of seven compounds consisting of chlorinated, fluorinated and aliphatic hydrocarbons was prepared. The composition-of this mixture and the chromatographic conditions are as follows: (1) dichloromethane (300 µg), (2) trichlorofluoromethane (150 µg), (3) trichloromethane (400 µg), (4) trichlorotrifluoroethane (150 µg), (5) tetrachloromethane (400 µg), (6) hexane (20 µg), (7) heptane (20 µg). This mixture was separated on a Carbopack (5% Fluorcol) column under temperature programming from 140° C. to 190° C. at 20° C./min with helium as the carrier gas at a flow rate of 30 mL/min. The fluorine selective mode of operation was carried out with the 2.35 µm and 2.50 µm filter combination in the analytical channel. The chlorine selective mode was carried out using the 3.8 µm filter in the analytical channel. The carbon mode of operation was carried out using the 4.4 µm filter in the analytical channel. A 3.0 µm filter was used throughout in the reference channel.

All chromatograms were run under identical conditions. The chromatograms are shown in FIGS. 33A–33C.

In the carbon mode 7 peaks result with the order of elusion from left to right as listed above. The compounds exhibiting peaks in the chlorine mode are from left to right (1) dichloromethane, (2) trichlorofluoromethane, (3) trichloromethane, (4) trichlorotrifluoroethane and (5) tetrachloromethane. In the fluorine mode only the two fluorinated compounds (2) trichlorofluoromethane and (4) trichlorotrifluoroethane are present from left to right. The chromatograms are shown in the subtracted and unsubtracted modes to illustrate the relative performance in the three selective modes of operation.

The results indicate that in the chlorine selective mode only the chlorinated compounds respond and similarly in the fluorine selective mode only the fluorine containing compounds respond. This confirms the preliminary results obtained earlier in terms of the selectivity ratio values obtained for the element selective mode. Also the results of the unsubtracted mode of operation are given for comparison. It is clear from these results that in the unsubtracted mode (for the chlorine and fluorine selective modes) the signal-to-noise ratio is far worse than in the subtracted mode. The signal-to-noise ratio improvements are qualitatively about an order of magnitude better for the subtracted mode in comparison to the unsubtracted mode. In the fluorine and chlorine selective unsubtracted modes the analyte peaks are just barely visible above the noise. In fact, in the fluorine mode (FIG. 33A), the peak heights are just about twice the p-p noise level.

The real advantage of the element selective mode of operation of the GC-flame infrared emission detector over commercial non selective GC detectors can be appreciated in situations calling for the analysis of fluorinated compounds in a complex matrix containing a host of non-fluorinated compounds. Qualitative and quantitive analysis of such a complex mixture can be very tedious and is often plagued with serious quantitative errors. Unambiguous qualitative identification can be very frustrating as a result of tedious steps involved in optimization of separation conditions. A reliable quantitative analysis can be highly complicated in the absence of complete resolution of the component peaks. When the analyst is interested only in the fluorinated compounds and not in the myriad of other components present in the matrix, then the fluorine selective GC-flame infrared emission detector provides the ideal choice. Since the fluorine selective mode of the detector responds selectively only to the fluorinated compounds, a simpler chromatograph with less peaks results, obviating the need for tedious and elaborate optimization schemes. Unambiguous qualitative identification and reliable quantitative data can be achieved under these conditions. As a part of our investigative study of the performance of the dual channel system operating in the fluorine selective mode, we have attempted to simulate such a condition; the details of the experimental approach are described in the following section.

Figure 34:
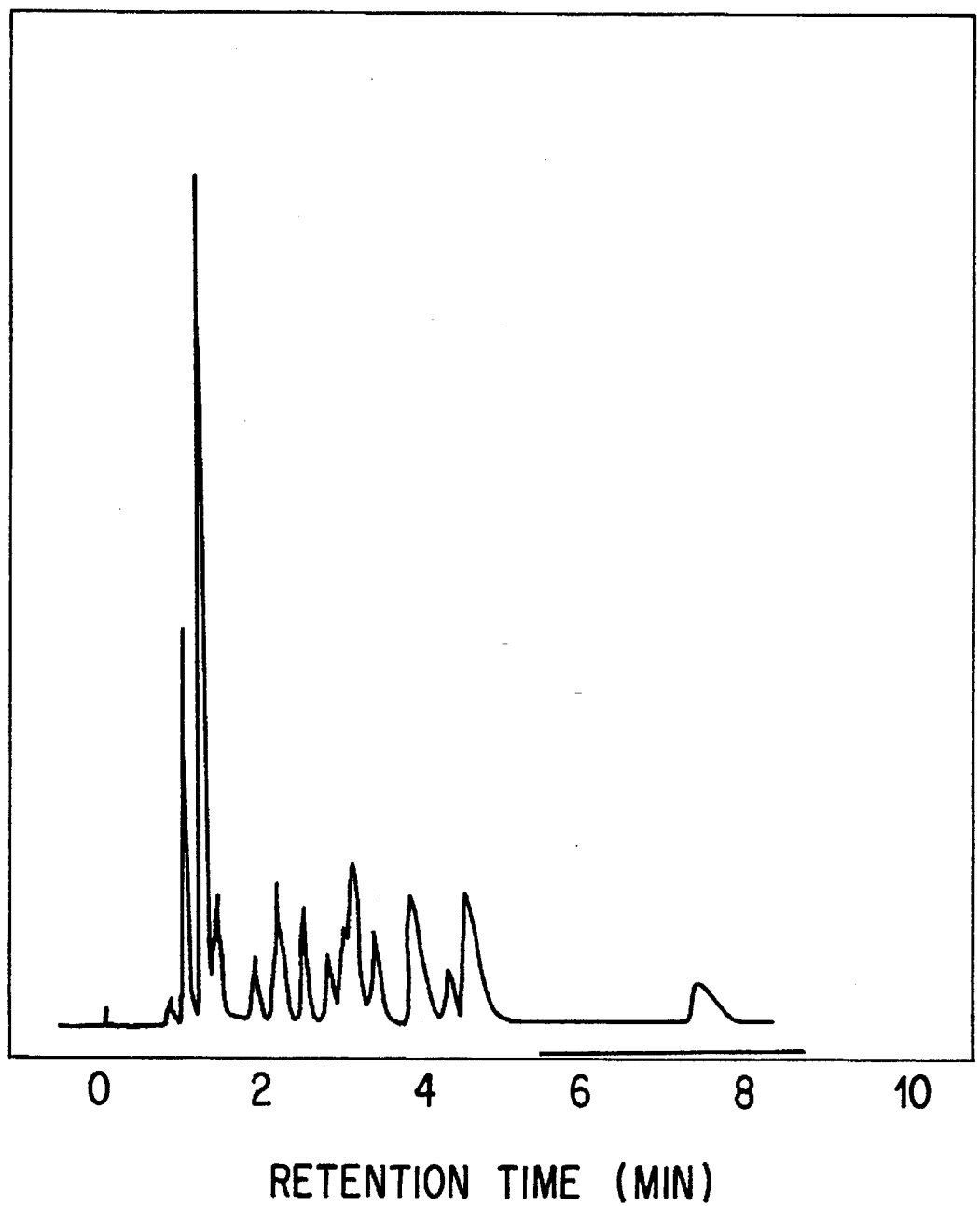
FIG. 34 is a chromatograph of a complex mixture utilizing a commercial TCD detector.
Figure 35:
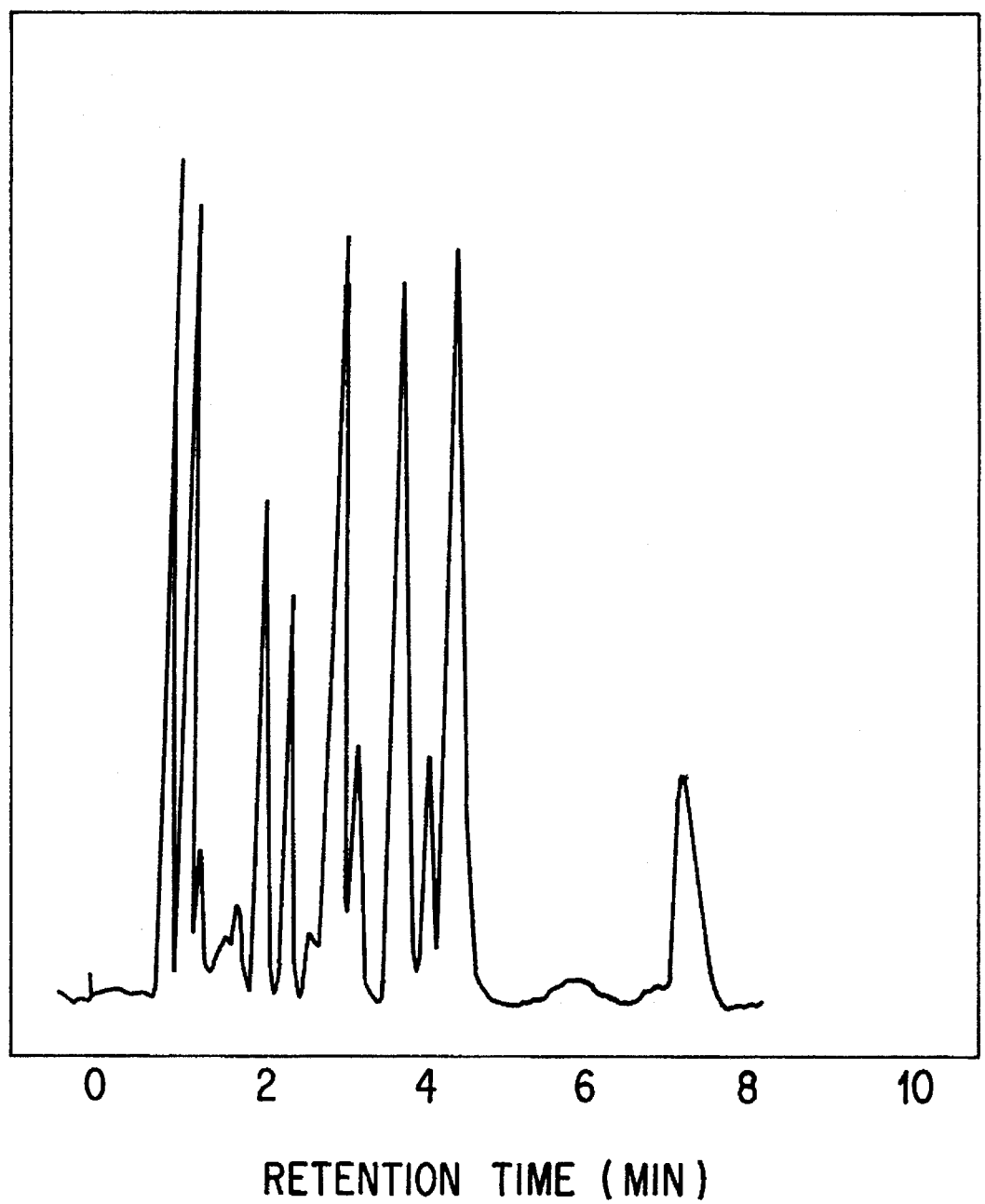
FIG. 35 is a chromatograph of a complex mixture utilizing a flame infrared emission detector in the carbon mode.
Figure 36:
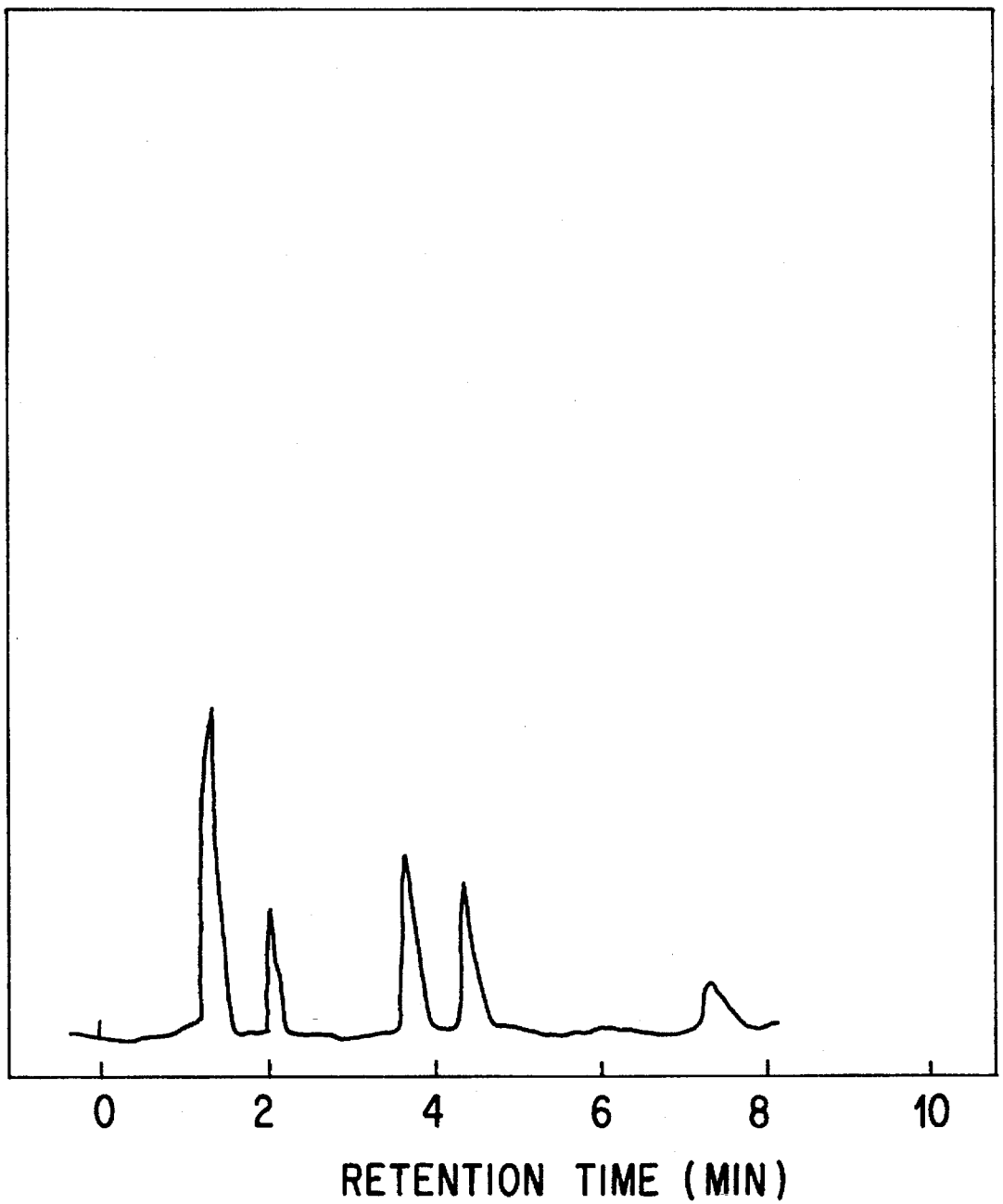
FIG. 36 is a chromatograph of a complex mixture utilizing a flame infrared emission detector in the fluoride selective mode.

A complex 19-component mixture of various organic compounds was prepared by mixing these compounds in approximately equal proportions by volume. The composition of this mixture is: (1) chlorobenzene, (2) chlorotoluene, (3) 2-chlorobutane (4) 1-chloro-2-methylbutane, (5) 1-chloro-2-methylpropane, (6) isopropyl chloride, (7) 1,3-dichloro-1-propene, (8) 3-pentanone, (9) ethyl acetate, (10) ethanol, (11) carbon tetrachloride, (12) chloroform, (13) dichloromethane, (14) pentane, (15) fluorobenzene, (16) difluorobenzene, (17) hexafluorobenzene, (18) trichlorotrifluoroethane, (19) methanesulfonyl fluoride. This mixture contains only 5 fluorinated compounds. The chromatographic conditions chosen for the separation were based on the optimum separation conditions chosen for the separation of the 5 fluorinated compounds. The optimum conditions were determined by chromatographing the 5 component mixture of the fluorinated compounds. The optimum chromatographic conditions that resulted were: Carbopack-B (5% Fluorcol); helium carrier gas (30 mL/min); temperature programming 180° C. to 220° C. at 20° C./min. The 19 component complex mixture was chromatographed under these conditions, with (a) a commercial TCD detector, (b) a flame infrared emission detector in the carbon mode and (c) a flame infrared emission detector in the fluorine selective mode. The chromatograms for the respective modes are shown in FIGS. 34, 35 and 36. With the TCD detector and the flame infrared emission detector in the carbon mode of operation only 15 peaks out of the total of 19 components are visible indicating an incomplete resolution of component peaks. As a result, no attempt has been made to identify and assign the component peaks in these two modes of operation. With the fluoride selective mode the results are rather impressive. Only the 5 peaks due to the 5 fluorinated components ((1) methanesulfonylfluoride, (2) trichlorotrifluoroethane, (3) fluorobenzene, (4) difluorobenzene and (5) hexafluorobenzene from left to right) are present. The chromatogram looks much simpler with excellent baseline resolution. The intrinsic simplicity of the chromatographic profile lends itself to an unambiguous peak identification. (The actual peak assignments were made using the retention times of these fluorinated compounds from individual injections of these compounds under identical chromatographic conditions).

Figure 37:
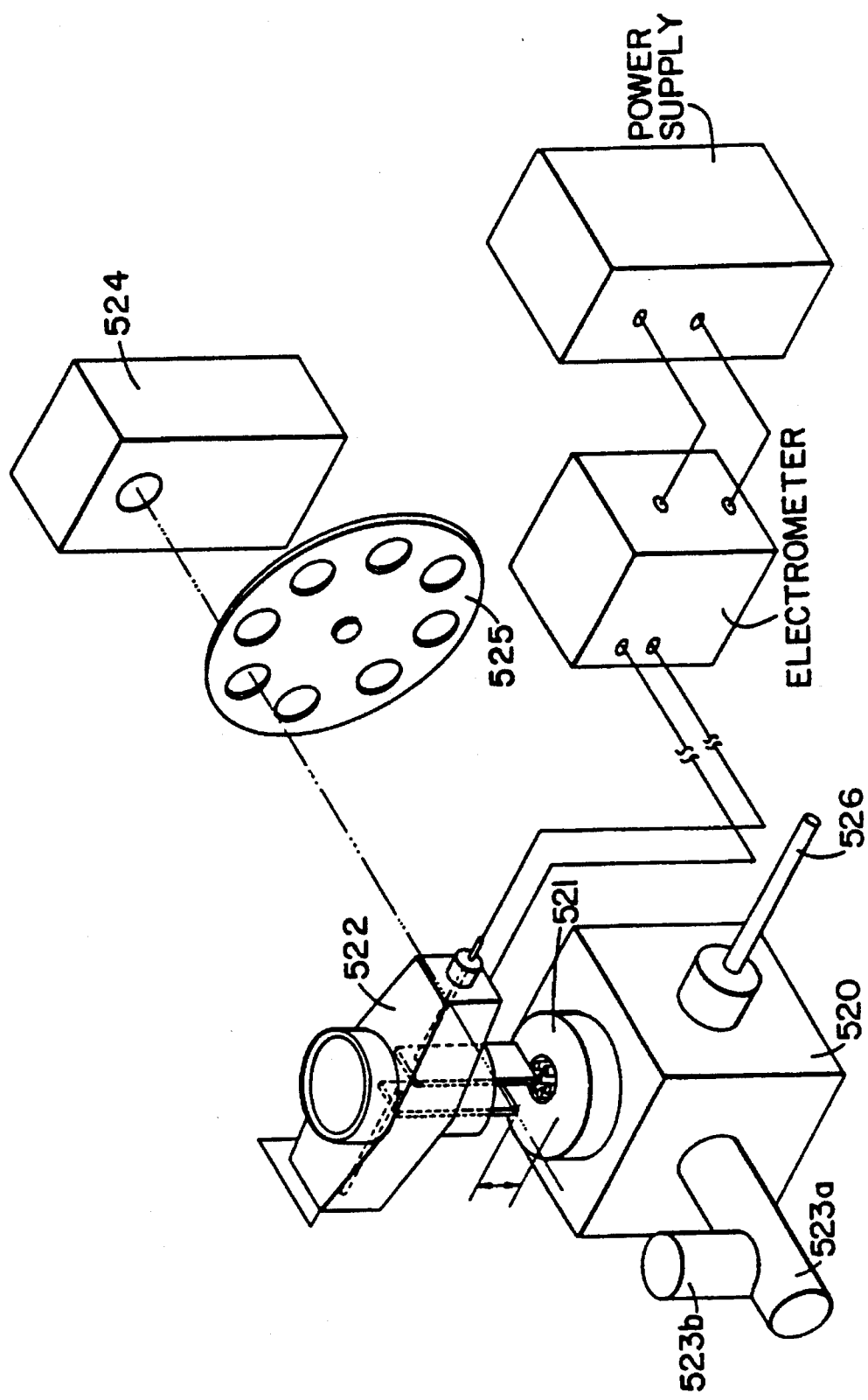
FIG. 37 schematically illustrates the apparatus for a combined infrared and flame ionization detector.

In a further embodiment, a flame infrared emission detector is combined with a flame ionization detector wherein the same flame is used to simultaneously conduct both types of detection. The flame infrared detector provides quantitation in terms of moles of carbon present in the compounds while the flame ionization detector provides higher sensitivity to extremely small amounts of hydrocarbons. Additionally the flame infrared emission detector is able to detect compounds not observed by the flame ionization detector such as carbon monoxide and carbon dioxide. An experimental schematic for a combined flame infrared emission/flame ionization detector is shown in FIG. 37. The burner body 520 is the same as described (Hudson and Busch, 1988). Hydrogen/air is used as the fuel/oxidant mixture being supplied to the capillary tubes of the burner through a Swagelok T 523a, 523b. The sample is supplied through the central capillary 526. The flame ionization detector utilizes two electrodes in an electrode assembly 522 where a potential of approximately 300 V DC is regulated between the electrodes by a power supply. An electrometer measures the ion current across the flame.

The infrared emission is simultaneously detected by a PbSe detector 524. Radiation from the flame is modulated by an optical chopper 525. The infrared detector 524 must not "see" the electrodes (due to blackbody emission background), therefore an aperture device is mounted on the infrared detector unit.

EXAMPLE 6

Gas-Phase Infrared Emission Spectroscopy Based on Thermal Excitation

The characteristics of the excitation source determine the sensitivity of infrared emission detection. An ideal excitation source should excite the analyte with high efficiency and have low background emission. The general requirements for an ideal emission source for FIRE spectrometry should include: 1) good conversion of the sample into the infrared-active emitting species of interest, 2) a temperature high enough to cause significant vibrational excitation without extensive decomposition of the infrared emitting species of interest, 3) absence of intense "blackbody" emission in the field of view of the detector, 4) low background in the vicinity of the emission(s) of interest, 5) a rapid sample introduction system that avoids high-volume mixing chambers, and 6) good long- and short-term stability.

Although hydrogen-based flames are convenient emission sources for FIRE spectrometry, they suffer from three disadvantages. 1) Use of combustion flames generally limits the technique to the utilization of infrared bands emitted by terminal combustion products of the analyte (i.e., $CO_2$, HCl, HF, etc.). 2) The flame background (which arises from vibrationally excited water vapor in the case of hydrogen-based flames) fluctuates, limiting the signal-to-noise ratio obtained with a simple FIRE radiometer. 3) The temperature of the flame is determined by the combustion process, and, with flame excitation, observation of the infrared emission from a sample over a wide range of temperatures is not possible. Many of the limitations associated with flame sources can be eliminated by using a specially designed furnace to produce the infrared emitting species.

The present inventors have demonstrated the feasibility of using a miniature electrical furnace as an excitation source in gas-phase infrared emission spectroscopy (Tilotta, et al., 1991). Compared to the hydrogen/air flame, a variable-temperature electrical furnace reduces background emission from the excitation source and can be further beneficial in applications where flames are hazardous (i.e., certain process control applications). Use of a heated furnace also may allow more instrument portability for in-field use (Busch et al., 1989).

The ability to vary the temperature extends the capability of the technique in terms of the number of infrared-emitting species that can be observed. Thus, while higher excitation source temperatures favor the production of terminal combustion products such as $CO_2$ and $H_2O$, lower excitation temperatures favor infrared emission from incomplete decomposition products, molecular fragments, or even the parent analyte molecule itself. Therefore, use of a variable temperature excitation source can increase the number of infrared emitting species available for monitoring and make the technique more compound specific as opposed to element specific. Useful infrared emission spectra can be obtained at excitation temperatures as low as 200° C., a temperature not greatly different from column temperatures commonly employed in gas chromatography. For example, the feasibility of determining the ethanol content in gasohol has been demonstrated at 200° C. with the use of the infrared emission band at 1070 $cm^{-1}$ (Tilotta, et al., 1991). One of the most important advantages of the electrically heated furnace, compared with hydrogen-based combustion flames, is the virtual elimination of additive flame background emission from water vapor (Busch M. A. and K. W. Busch, 1991).

A key aspect in the design of a miniature electrical furnace for gas-phase infrared emission spectroscopy is the minimization of extraneous blackbody radiation from hot, condensed-phase material because such radiation can obscure the relatively weak gas-phase emission from the sample. In the case of a miniature electrical furnace, this requirement means that it is imperative that the field of view of the radiometer be restricted so that blackbody radiation from the furnace walls will not be observed by the detector. This requirement can be satisfied, for example, if the observation zone of the radiometer is located after the hot gases emerge from the electrically heated region into the ambient atmosphere. Direct observation of the furnace walls by the FIRE radiometer can be avoided, for example, by orienting the furnace in a direction that is orthogonal to the optical axis of the detector so that radiation from the hot tube itself is not observed by the detector. With some furnace designs that have been evaluated (Tilotta, et al., 1991), an external cooling water jacket surrounding the furnace was used to remove stray blackbody radiation emitted by the furnace case.

One problem encountered with the use of electrical furnace excitation alone has been the nonlinearity of the calibration curves obtained with the instrument. Studies with a miniature electrical furnace or a small hydrogen/air flame have shown that oxidation of a variety of carbon-based analytes to $CO_2$ over an oxidation catalyst such as hopcalite (a co-precipitate of manganese and copper oxides) prior to vibrational excitation in the furnace or flame markedly improves the linearity of the response of the FIRE radiometer (Zhang et al., 1992). Calibration curves obtained with the use of the furnace alone were generally nonlinear, while those obtained with the flame alone had slopes that were compound dependent. Use of hopcalite in conjunction with the furnace significantly improved the conversion to $CO_2$, and the FIRE response to pure acetone, benzene, dichloromethane, 1-chloro-2-methylpropane, heptane, methanol, and toluene became directly proportional to the number of moles of carbon introduced. Hopcalite catalyst is relatively inexpensive compared with precious metal oxides, so catalyst replacement is also inexpensive.

Furnace Design.

The miniature electrical furnace may be interfaced with a nebulizer/spray chamber. The body of the furnace may be fabricated from a 6 cm cylindrical piece of aluminum stock, and can consist of two sections. The lower section functions as an interface between the nebulizer/spray-chamber assembly and the ceramic furnace rod. The furnace itself may contain a high-temperature (1950° C.), 6 cm 6.4 mm OD, hollow-core (3.2 mm ID) ceramic rod (part #ORX-1814, Omega Engineering, Stamford, Conn.) would with 20 turns of type K chromel wire (part #SPCH-032, Omega Engineering). The chromel wire may have an internal resistance of 0.586 Ω per double foot at 68° C., and may used to heat the ceramic rod externally by the application of a variable voltage. The ends of the chromel wire may be insulated electrically from the aluminum section of the furnace with high-temperature Nextel braiding (part #XC-116, Omega Engineering) and then fed through 2.5 mm right-angle holes in the lower section of the furnace body.

The upper section of the furnace assembly may consist of a 1.5 cm ID inner chamber used to contain the furnace rod and chromel wire and an outer chamber used to cool the outside of the furnace body and reduce blackbody background radiation. (The wall thickness between the two chamber is about 7.0 mm.) The upper section is attached to the lower section by screw threads, and the two chambers of the furnace may be isolated from one another by two O-ring seals. The ends of the chromel wire in the lower section (insulated with the Nextel sleeving) is fed through the inner chamber casing and not through the cooling water chamber casing.

Cold tap water, used as the cooling water, is admitted into the outer chamber of the upper section by a standard ¼ inch NPT to ¼ inch Swagelock fitting adaptor (part #B-400- 1-4, Swagelock Co., Solon, Ohio) and ¼ inch ID polyethylene tubing. A similar arrangement was used for the cooling water outlet. A cooling water flow velocity of 400 mL min$^{-1}$ maintained the outer wall of the furnace assembly at room temperature.

The nebulizer/spray-chamber assembly consists of a Jarrell-Ash Model X-88 pneumatic nebulizer coupled to a small Teflon® spray chamber. The nebulizer may be operated from compressed air at a flow rate of 200 mL min$^{-1}$ and a fluid uptake rate of 1.5 mL min$^{-1}$. The nebulizer/spray-chamber assembly may be press-fitted into the side of the interface chamber.

The electrical furnace may be operated from a high-current, regulated, DC power supply (part #68735, Oriel Corp., Stratford, Conn.) when infrared emission measurements are made at moderate temperatures (in excess of 200° C.) with a Fourier transform spectrometer (FTS). For lower-temperature measurements, the furnace may be powered from a 24-V, 12-A, step-down transformer (part #P-8666, Stancor, Logansport, Ind.) connected to a laboratory variac.

Instrumentation.

All infrared emission spectra may be acquired on an unpurged Mattson Cygnus 100 Fourier transform spectrometer (Mattson Instruments, Madison, Wis.). The infrared global source and source-collimating mirror may be removed to allow access to the Michelson interferometer in the instrument. A 10 cm focal-length, 10 cm diameter aluminum mirror may be used to collect and collimate the infrared emission from the source.

The furnace is oriented so that the hot gas stream emerges from the heated ceramic rod in a vertical direction (i.e., orthogonal to the optical axis of the FTS). The infrared radiation emitted is observed over a 0.4 cm vertical segment (determined from the aperture size of the spectrometer) centered at a height of 1.5 cm from the top of the furnace outlet.

A room temperature triglycine sulfate (TGS) detector ($D^*=2\times10^9$ cm $H^{1/2}$ $W^{-1}$) and KBr beamsplitter may be employed in the FT-IR spectrometer. Because the infrared emission from samples introduced into the furnace may be relatively weak in comparison to the radiance from the normal global source in the instrument, an additional preamplification stage may be added to the spectrometer. An SK3590 (RCA Corp., Somerville, N.J.) frequency-compensated operational amplifier (configured as a voltage follower with a fixed gain of 100 and a flat response bandwidth from 1 Hz to 1 MHz) may be decoupled between the existing preamplifier and the main amplifier of the FTS. A voltage divider network located in the inverting input of the operational amplifier allows the output of the preamplifier to be zeroed.

Procedure.

Before use, the furnace was allowed to warm up for approximately 15 min. with the cooling water flowing and the DC power supply adjusted to yield an excitation temperature of approximately 200° C. In addition, the FTS global source was disconnected, and the optical components of the spectrometer were allowed to cool for 15 min. prior to use.

Liquid samples were admitted into the furnace by direct aspiration with the nebulizer. Gas samples, such as nitrous oxide, were admitted by coupling the cylinder outlet into the line normally used for the nebulizer aspiration gas (i.e., the compressed air line).

All temperature measurements were performed with a thermocouple probe (part#871A, Omega Engineering, Inc.). Excitation temperatures given for the infrared emission spectra were obtained with the thermocouple probe located at an appropriate height above the furnace outlet (which corresponds to the optical axis of the FTS).

All spectra were acquired with 4 cm$^{-1}$ resolution at mirror velocity of 0.32 cm s$^{-1}$. A Beer-Norton medium (F2) apodization function was used with 1× zero filling and, due to the discrete line nature of the emission spectra, phase correction was not applied. Instead, the single beam power spectra were calculated and plotted. None of the spectra in this paper have been corrected for the instrument response of the FTS. A spectrum of the residual emission background emitted by the hot gas stream from the furnace was obtained by coadding 1000 scans. This background spectrum was subtracted from each of the emission spectra. All spectra, unless otherwise noted, are the result of 100 coadded scans and required a total observation time of eight minutes.

Ethanol Calibration Curves.

In an effort to construct a calibration curve for ethanol, a 2 mL volume of a standard gasohol solution was aspirated into the furnace and the spectrum acquired. In order that matrix effects due to different base gasoline compositions could be minimized, a 2 mL volume of the same gasohol standard was then diluted with an equal volume of distilled, deionized water and shaken for three minutes to extract the ethanol into the aqueous phase. (Shaking the gasohol with water for three minutes was found to reduce the ethanol concentration in the gasohol to below the detection limit.) After extraction, the water layer was decanted, and a second emission spectrum of the gasoline was acquired. Subtraction of the two spectra yielded a spectrum of the ethanol present in the gasohol sample, and the height of the emission band of ethanol at 1070 cm$^{-1}$ was measured. This process was repeated for all gasohol standards to construct a calibration curve of emission intensity (i.e., peak height) versus ethanol concentration.

Furnace Design.

Before a discussion of the details of the furnace used in this study, the requirements for any emission source in gas-phase infrared-emission spectroscopy will be considered. The most important requirement is minimization of extraneous blackbody radiation from hot, condensed-phase material since such radiation can obscure the relatively weak gas-phase emission from the sample. This means that an ideal gas-phase infrared-emission source must be capable of producing a region of hot gas in free space, i.e., space that is not surrounded by or in close proximity to hot, condensed-phase matter within the field of view of the detector. In the case of an ordinary combustion flame, such as the hydrogen/air flame used in previous studies, this requirement is easy to satisfy because the flame burns in the open atmosphere, well above the burner tip, and it is not enclosed or surrounded by any hot, condensed-phase matter within the field of view of the detector. In the case of an electrically heated furnace, however, it is imperative that the observation zone be located after the hot gases emerge from the electrically heated region. If the furnace consists of an electrically heated tube (as in the present study), it is also important to orient the furnace tube in a direction that is orthogonal to the optical axis of the detector so that radiation from the tube is not observed by the detector.

Finally, an ideal source for gas-phase infrared emission spectroscopy should also be capable of variable-temperature operation. In previous studies using a hydrogen/air flame, most organic samples were largely converted to terminal combustion products such as $CO_2$, $H_2O$, HCl, and HF. This combustion process generally precluded the observation of infrared emission from other thermal decomposition products, molecular fragments, or the parent analyte molecule itself, as well as optimization of the signal through adjustment of the $\alpha(T)e^{-h\nu/kT}$ product (Eq. 1).

The electrothermal furnace presented in this paper represents the best of several designs that were evaluated as infrared emission sources in this laboratory. The water-cooling jacket around the ceramic rod and chromel wire was essential for removal of excess stray infrared radiation originating from the aluminum furnace case. Without cooling, this background radiation completely obscured the gas-phase infrared emission signal arising from the sample. Ordinary tap water, at a temperature of approximately 17° C. and a flow rate of 400 mL min$^{-1}$, was sufficient to maintain ambient temperature conditions in the furnace casing. However, because the ceramic rod and wire assembly also had to be electrically and thermally insulated, a portion of the aluminum casing located at the outlet of the furnace could not be cooled by the tap water. Measurements made during operation showed that the temperature of this uncooled region (about 1 cm$^2$) rose to approximately the same temperature as the heating coils surrounding the ceramic tube. However, because this portion of the furnace was not in the field of view of the FTS, the heated region did not contribute to the production of any interfering background radiation.

The background spectra obtained was compared with the hydrogen/air flame and the electrical furnace set for an excitation temperature of 200° C. The background spectrum for the excitation zone of the electrical furnace was obtained by coadding 1000 scans with the FTS, while that of the hydrogen/air flame is the result of coadding 100 scans.

The integrated spectral radiance $L_\nu$ of a Plank black-body radiator as a function of wavenumber $\bar{\nu}$ is given by Eq. 2:

$$L\bar{\nu} = \frac{2hc^2}{\bar{\nu}^3} \frac{d\bar{\nu}}{e^{hc\bar{\nu}/kT} - 1} \quad (2)$$

where c is the speed of light, and the remaining terms are the same as in Eq. 1. This blackbody curve, plotted for a temperature of 200° C., showed that the background radiation for the excitation zone of the furnace is not only free of any blackbody component but is also free of most of the water bands present in the background of the hydrogen/air flame. The band observed in the 1000–500 cm$^{-1}$ region with the use of the electrical furnace probably arises from the low-energy excitation of residual water vapor and carbon dioxide in the hot source region sampled by the spectrometer. (The lack of emission bands in the high-energy infrared region will be discussed in a following section.) The sharp absorption observed at approximately 667 cm$^{-1}$ is most likely due to the absorption of the emitted radiation by atmospheric $CO_2$. (The bending mode of $CO_2$ is observed at 667 cm$^{-1}$ in the gas phase.)

For analytical applications, the intensity of the furnace background spectrum in the 1000–500 cm$^{-1}$ region was found to correspond to less than one-tenth of the maximum emission intensity of most samples. Thus, the furnace background emission did not produce a serious interference problem, as it could easily be removed from the sample spectrum by subtraction.

Temperature Control.

The furnace was heated electrically by applying a voltage across the chromel wire wrapped around the ceramic rod. The coiled chromel wire encompassed a length of 2.5 cm along the ceramic rod and resulted in an intercoil spacing of approximately 1.0 mm. The temperature of the furnace was controlled externally from either an AC or DC power supply, and the internal wall temperature of the furnace as a function of applied voltage was substantially linear above 50° C. It should be emphasized that the temperature measurements correspond to the internal wall temperature of the furnace as measured with the thermocouple probe, not the actual excitation temperature at the optical axis (i.e., 1.5 cm above the furnace outlet). the maximum internal wall temperature attainable by this furnace was determined to the 1100° C. and corresponded to the point at which the chromel wire failed.

Low-Temperature, Gas-Phase, Infrared Emission Studies.

To demonstrate the ability of low-temperature, gas-phase, infrared emission spectroscopy to detect species that cannot be observed in the hydrogen/air flame, we obtained the infrared emission spectrum of nitrous oxide, $N_2O$, by introducing 50 mL min$^{-1}$ of the gas into the furnace, set to give an excitation temperature of 225° C. (With the use of the Mattson Cygnus 100 FTS, TGS detector and 100 coadded scans, most samples required a temperature of at least 100° C. before an infrared emission spectrum with an adequate signal-to-noise ratio could be acquired.) The infrared emission spectrum of nitrous oxide is not observed in the hydrogen/air flame because nitrous oxide is thermodynamically unstable at temperatures above 600° C., decomposing into $N_2$ and $O_2$, both of which are infrared inactive, and reacting readily with $H_2$ to form $N_2$ and $H_2O$.

Because $N_2O$ is an asymmetric linear triatomic molecule, it has four fundamental modes of vibration, and its infrared spectrum in absorption consists of three bands: two stretching vibrations ($v_3$, 2156–2224 $cm^{-1}$ and $v_1$, 1266–1286 $cm^{-1}$), and a degenerate bending mode ($v_{2a}$, and $v_{2b}$, 572–589 $cm^{-1}$). The exact position of the absorption bands depends on the isotopic substitutions possible for nitrogen (i.e., N-14 and N-15).

The infrared emission spectrum of nitrous oxide obtained after subtraction of the furnace background spectrum shows three infrared bands at locations corresponding to those expected for $v_1$, $v_2$, and $v_3$. The splittings observed for each band are probably due to a combination of self-absorption and isotopic substitution.

When methyl benzoate was aspirated into the furnace at two different excitation temperatures, the spectrum obtained at an excitation temperature of 250° C. showed prominent emission bands at 1730, 1280, 1120, and 710 $cm^{-1}$ with weaker bands at 1600, 1450, 1190, and 1040 $cm^{-1}$. The and at 1730 $cm^{-1}$ is clearly indicative of a carbonyl stretching vibration in aromatic esters, while the bands in the 1500–1000 $cm^{-1}$ region can be attributed to alkyl CO, aryl CO, and C(=O)O stretching. The band at 710 $cm^{-1}$ may be indicative or aromatic CH vibrations. Because of the close correlation between bands observed in the emission spectrum at 250° C. with the bands observed in the conventional absorption spectrum, the emitting species at 250° C. is probably the parent molecule, methyl benzoate, rather than a thermal decomposition product.

The infrared emission spectrum obtained when methyl benzoate was aspirated into the furnace at an excitation temperature of 700° C., the molecular bands observed at 250° C. have all disappeared, and only the bands from $CO_2$, 400–2200 $cm^{-1}$ and 667 $cm^{-1}$ are evident. It is interesting to note that, although the carbon dioxide emission bands are clearly present in the spectrum, the characteristic water bands are relatively weak or absent. This may indicate that the infrared emission spectrum observed at 700° C. with the electrical furnace is due primarily to partial decomposition of the methyl benzoate molecule (i.e., loss of $CO_2$ from the ester functional group) rather than complete oxidation to $CO_2$ and CO.

It is also interesting to note that, in general, few bands are observed in the short-wavelength region (1–4 μm) with low-temperature, gas-phase infrared emission. The lack of emission bands in this region can be rationalized as the basis of the fraction $N^*/N_T$ of vibrationally excited molecules available for a particular vibration at a given source temperature. Previous work has shown that at any vibration $\bar{v}$, this fraction will be given by $$\frac{N^*}{N_T} = \alpha(T) e^{-hv/kT} \quad (3)$$

plot of $N^*/N_T$ versus the wavelength of the emission band for several source temperatures, assuming $\alpha(T)$ equals one shows that molecules with vibrational bands in the region from 1 to 20 μm will not be appreciably excited at 200° C., in commission with vibrational bands at longer wavelengths. This, at low temperatures, the absence of emission bands in the 1–4 μm spectral region does not necessarily indicate the absence of potential emitting moieties in the source-only that the number of such emitters is too small to detect.

The infrared emission spectrum of pure ethanol obtained at a furnace excitation temperature of 202° C. shows the primary emission bands observed in the low-temperature spectrum extend from 1500 to 800 $cm^{-1}$, with the strongest component occurring at 1070 $cm^{-1}$. The band at 1410 $cm^{-1}$ can be assigned to OH deformation, and the band at 900 $cm^{-1}$ to CH bending. The observed band at about 2900 $cm^{-1}$ is probably due to OH stretching and is extremely weak because of the low excitation temperature of the furnace. The infrared emission at 1250 and 1070 $cm^{-1}$ can probably be assigned to C—O stretching, typically observed for alcohols as a split band at 1250–1000 $cm^{-1}$ in absorption. The actual position and splitting of the C—O stretching band in low-temperature infrared emission may be altered from that observed in conventional absorption spectra by strong self-absorption resulting from the presence of large numbers of ground-state ethanol molecules in the source region sampled by the FTS. Based on this study, only about 7% of the ethanol molecules are expected to be in excited vibrational levels of the C—O stretching vibration at 200° C. Determination of Ethanol in Gasohol.

To demonstrate the utility of low-temperature, gas-phase, infrared emission spectroscopy for analysis, we selected the determination of the ethanol content in gasohol as a potentially interesting application. Since the band at 1070 $cm^{-1}$ is the strongest feature of the low-temperature infrared emission spectrum of ethanol, and since previous absorption studies had shown that the C—O stretching vibration is reasonably free from interfering bands from other species that may be present in gasohol, $1070^{-1}$ cm was chosen as the analytical wavelength for preparation of the calibration curve.

The calibration curve for ethanol was prepared by subtracting the base gasoline spectrum from the spectrum of the gasohol, as described previously. A low-temperature infrared emission spectrum of gasohol obtained by aspirating a 10%-by-volume ethanol/gasoline solution into the furnace showed an infrared emission spectrum of the base gasoline obtained after aqueous extraction of the ethanol. The difference spectrum, obtained by substraction is normalized with the common band at 1460 $cm^{-1}$. Examination showed that it is identical with the pure ethanol spectrum.

A plot of C—O stretching intensity at 1070 $cm^{-1}$ versus percent by volume of ethanol in a series of gasohol standards prepared over a range from 1 to 20% v/v showed the downward curvature exhibited by the calibration curve is most probably a result of strong self-absorption by unexcited ethanol molecules present in the source region. Curvature for high analyte concentrations is expected in low-temperature infrared emission because the linear range of intensities can extend only up to the Planck blackbody limit. Once the spectral radiance at a given wavelength reaches the Planck blackbody limit, self-absorption becomes severe, and the emission band broadens as the analyte concentration in the source increases.

To obtain some idea of the magnitude of this fundamental limitation on the infrared emission signal, we calculated the blackbody radiances as a function of wavelength $\lambda$ for several excitation source temperatures. Since $d\lambda = -\bar{v}^{-2} d\bar{v}$, Eq. 2 can be written as $$L_\lambda = \frac{2hc^2}{\lambda^5} \frac{d\lambda}{e^{hc/lambdakT} - 1} \quad (4)$$

The limiting blackbody radiances over the wavelength range from 3 to 20 μm showed that the upper radiance limit before the onset of self-absorption will be quite low for excitation source temperatures of 200° C., compared with that for higher temperatures. In spite of this curvature, the calibration curve is still useful analytically and can be used to determine the ethanol content of unknown gasohol samples.

The detection limit obtained with this furnace system for ethanol in gasohol, defined at a v/v % of ethanol producing a signal equivalent to twice the root-mean-square noise, was 0.124% v/v. The relative standard deviation of exhibit single-scan determinations of the ethanol content in a standard 10% gasohol sample was 4.01%. Both the detection limit and the reproducibility could be improved by the coaddition of a larger number of spectral scans.

This example demonstrates the feasibility of using a miniature electrical furnace as an excitation source in gas-phase-infrared emission spectroscopy. Compared to the hydrogen/air flame, a variable-temperature electrical furnace greatly reduces background emission from the excitation source and can be further beneficial in applications where flames are hazardous (i.e., certain process control applications). Useful infrared emission spectra can be obtained at excitation temperatures as low as 200° C., a temperature not greatly different from column temperatures commonly employed in gas chromatography. Low-temperature excitation also promotes emission from the parent molecular analyte, rather than from terminal combustion products, such as $CO_2$ and $H_2O$. Low-temperature excitation (200° C.) is not energetic enough for appreciable excitation of infrared emission bands in the 1–4 μm spectral range, however. Another problem likely to be encountered with low-temperature infrared emission is a more limited linear dynamic range involving the detection limit at the low end and the Planck blackbody limit at the upper end.

The feasibility of determining the ethanol content in gasohol has been demonstrated with the use of the infrared emission band at 1070 $cm^{-1}$. Although measurements of infrared emission intensity presented in this example utilize an FTS, a simple filter instrument could be developed which would be equally suitable for gasohol analyses.

Figure 46:
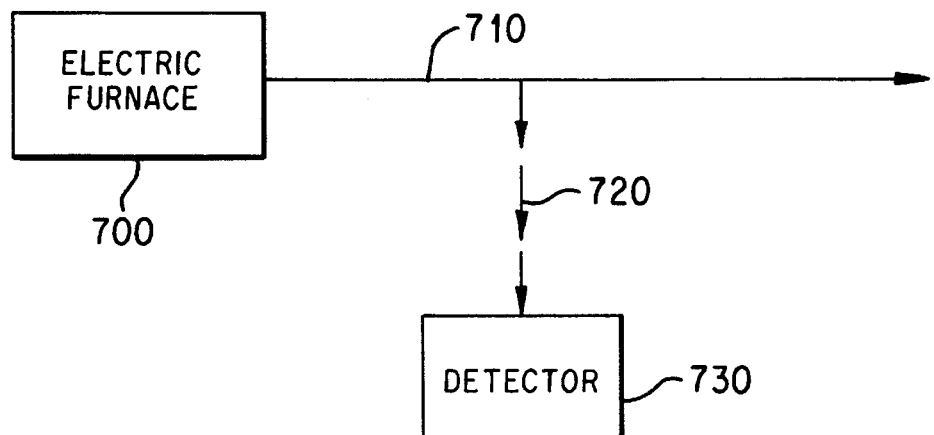
FIG. 46 shows a detection and measurement apparatus of this invention including an electric furnace.

In FIG. 46 there is shown an apparatus for detecting infrared radiation and making quantitative measurements, including electric furnace 700 wherein infrared-active molecules to be excited are excited by thermal heating. The excited molecules exit furnace 700 as a stream of molecules 710 which emits infrared radiation 720. Infrared radiation 720 is detected by infrared radiation detector 730.

EXAMPLE 7

Infrared Emission Spectroscopy Based on Electrical Excitation

The literature indicates that analytical work with gas-phase IR emission up to the present is based on non-selective thermal excitation with energy introduced into the analyte by direct electrical heating or transfer of thermal energy from hot flame gases. For sources in thermal equilibrium, thermal excitation results in a Boltzmann distribution of excited states with all molecules having a degree of vibrational excitation consistent with a particular temperature characteristic of the source. This non-selective thermal excitation leads to emission from all the infrared-active molecules that may be present in the excitation source as well as blackbody radiation from any condensed phase matter in close proximity to the source. Even laser excitation of gas-phase samples is actually based on thermal excitation rather than direct excitation through photon absorption, due to the poor match between laser photon energy and the energy difference in the vibrational levels to be excited (Belz et al., 1987).

With thermal excitation sources, a large portion of the energy consumed (or produced) by the source is used to heat the matrix and the equipment within which the analyte is contained. With thermal excitation using a miniature electrical furnace, for example, the furnace itself emits an intense blackbody radiation which makes it necessary to observe the emission above the furnace where the emerging gases being to cool. Since the maximum temperature obtainable with a miniature electrical furnace is limited to begin with by the physical properties of the materials that make up the furnace (i.e., the melting point), having to observe the emerging gases above the furnace (to avoid detecting blackbody radiation) where the gases have cooled still further limits the sensitivity of the technique. While flame excitation gives less blackbody type emission than an electrical furnace, the flame itself emits background radiation in the form of characteristic vibrational bands from combustion products which may limit the usable wavelength range for emission analysis and degrade the signal-to-noise ratio.

Excitation of gas-phase infrared emission can be accomplished non-thermally by means of electrical discharges or plasmas (i.e., ionized gases). A plasma is formed when electrical energy is coupled to free electrons in the plasma. This electrical energy may be coupled to the plasma directly by means of electrodes (i.e., an electric field) or by inductive or capacitive means in the case of electrodeless discharges. Whatever the means of energy coupling, electrons within the plasma are accelerated in response to electric fields or magnetic fields. A stable plasma forms when the accelerated electrons acquire sufficient energy between collisions to ionize the matrix gases. Thus, the primary means of energy transfer in electric discharges is through electron impact. As the electron density in a plasma increases, the number of collisions between electrons and gas molecules increases to a level where thermal equilibrium is approached. Such plasmas are known as collision dominated plasmas and are characterized by a single temperature in the same way as an electrical furnace in thermal equilibrium. If the electron density of the plasma is too low to maintain collision domination, the electron energy distribution and gas molecule energy distribution will not be the same. In such a situation, the "electron temperature" exceeds the gas temperature, and the plasma is referred to as a non-equilibrium plasma.

Figure 47:
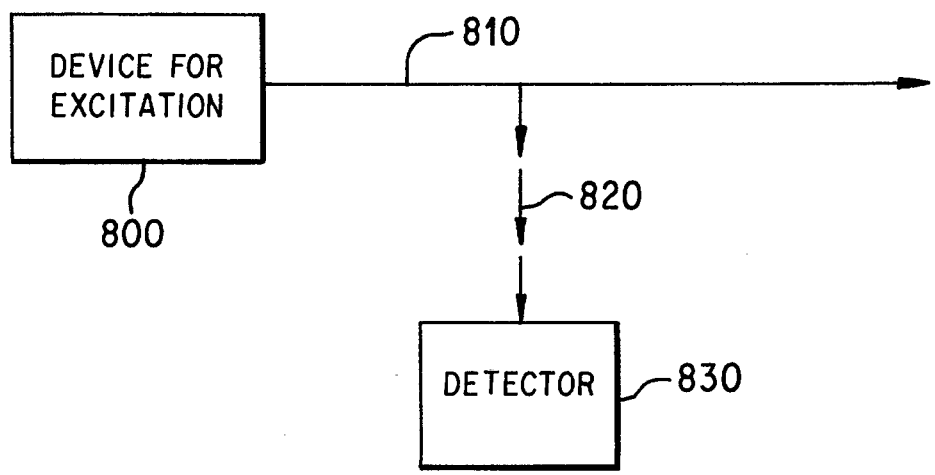
FIG. 47 shows a detection and measurement apparatus of this invention including a means for excitation by electron impact in a gas discharge.

In FIG. 47 there is shown an apparatus for detecting infrared radiation and making quantitative measurements, including device for excitation by electron impact in a gas discharge 800 wherein molecules to be excited are excited by electron impact. Excited molecules exit device 800 as a stream of molecules 810 which emits infrared radiation 820. Infrared radiation 820 is detected by infrared radiation detector 830.

In non-equilibrium plasmas, it is possible for the electron temperature to be as high as 10,000K or more while the gas temperature remains at several hundred degrees. In such situations, various unique excitation mechanisms exist whereby energy can be coupled into vibrational modes of excitation while the actual kinetic energy of the gas molecules themselves (and the surrounding containment) remains quite low (i.e., at a low temperature). Non-equilibrium plasmas are frequently observed under conditions of low pressure where the collision density is low. The advantage of non-thermal excitation can best be illustrated by electric discharges in nitrogen at low pressure. In these discharges, nitrogen is excited directly by electron impact to electronically excited levels. These excited electronic levels decay to the electronic ground state, leaving the nitrogen molecules in excited vibrational levels. Since nitrogen is a homonuclear diatomic molecule, it is quantum mechanically forbidden for it to lose vibrational energy by radiative processes. As a result, high populations of nitrogen molecules in the first and higher vibrational states build up in nitrogen discharges. Since the vibrational levels of nitrogen are nearly resonant with the 00°1 excited state of carbon dioxide (i.e., the asymmetric stretching vibration) collisions of the second kind between excited nitrogen molecules and carbon dioxide can lead to energy transfer between metastable nitrogen molecules and ground state (000) carbon dioxide molecules. In the $CO_2$ laser, originally described by C. K. N. Patel [see, for example, C. K. N. Patel and E. D. Shaw, *Phys. Rev. Lett.*, 24:451 (1970)], this mechanism is used for the highly selective excitation of the lasing gas (He, $N_2$, and $CO_2$) to give vibrationally excited species without converting large amounts of energy to kinetic energy. The ability to couple electrical energy into vibrationally excited states without heating the gas is crucial to laser action, because the surrounding gas and laser tubing which contains the gas must be kept at or near room temperature to maintain the required population inversion for lasing action. Selective excitation of vibrational states without excessive gas heating has also been achieved with the transversely excited atmospheric pressure $CO_2$ (TEA) laser system.

Analytical application using energy transfer from electrically generated active nitrogen has been reported for atomic emission measurements (Jurgensen and Winefordner, 1984). Plasma and metastable energy transfer excitation use a similar principle. A unique feature of the present inventive system is the high efficiency in energy transfer to the analyte from the near resonance energy exchange condition. This can only be approached in IR emission excitation, such as excitation of $CO_2$ with active nitrogen produced by electric discharge. Because of quantum mechanical restrictions, $N_2$, and other homo-nuclear diatomic gas molecules are infrared inactive (i.e., cannot undergo radiative transitions to lower states) and can lose their energy only through collisions with other molecules. As such, these vibrationally excited nitrogen molecules can serve as a selective energy source to analyte molecules with resonant or near-resonant energy levels. Because it is infrared inactive, nitrogen cannot emit infrared radiation, and plasmas formed in pure nitrogen will be free of interfering matrix gas emission over the entire range of vibrational emission. A second unique feature of the present inventive system is the negligible excitation of other concomitants in the sample (i.e., the sample matrix) due to lack of resonance. The combination of the lack of background emission of the medium gas and lack of resonance with the sample matrix allows the present excitation method to approach ideal conditions for excitation.

Instrument Set-up with AC Arc Discharge.

A variety of electrical discharges has been investigated in the laboratory ranging from corona discharges at atmospheric pressure to AC arc discharges to low-pressure electrical discharges in nitrogen. All of the discharges have been produced with a center-tapped high voltage transformer (Franceformer, Division of Scott & Fetzer Co., Fairview, Tenn.), widely used as a neon-sign transformer. The discussion that follows describes the use of this transformer to produce an AC arc discharge. The discussion that follows is illustrative of the results that can be obtained by means of electrical discharges and should not be taken as indicating the optimum excitation means. The high voltage center-tapped transformer used in these studies is especially suited to produce an AC arc discharge because it is a current limited device that provides limited current flow after the arc discharge path has formed and a low potential drop through the discharge has developed. This allows safe operation with varying distances of the discharge electrodes.

For these experiments, the high voltage output wire was soldered to 1/8" copper tubing to construct a high potential electrode. The outside of the copper tubing was insulated with 1/4" plastic tubing. Additional plastic tubing was added as insulation until the voltage at the insulting tubing surface with respect to ground was the same as that measured with a multimeter for standard high voltage wire. A copper wire, connected to the center tap (ground) of the transformer served as the second electrode. The case of the transformer was grounded with a separate wire to ensure safety. A variac was used to control the voltage supplied to the primary stage of the high voltage transformer. Two distinct discharges formed during each cycle of the power supply (60 Hz). Current flow in the discharge was sufficient to melt a 1/16" stainless steel tube in about 1 minute when it was used as the ground electrode. By contrast, 1/8" copper tubing was not severely damaged nor overheated, even for prolonged periods of operation. The plastic insulation, which came within 5" of the electrode tip was not damaged during continuous operation.

The arc discharge acts as a high frequency emitter of electromagnetic energy that can cause high frequency interference in sensitive electrical equipment in close proximity to the arc. To minimize the effects of magnetic field changes from the high voltage transformer and to prevent inadvertent contact with the high voltage components, the transformer was located in an aluminum housing. To reduce the amount of high frequency electrical interference, the arc was also located in an enclosed aluminum housing. Better shielding could be possible if the aluminum housings were made from a material with a high magnetic permeability. Care must be exercised in grounding the arc and other electrical equipment to avoid the formation of ground loops.

Arrangement of the Electrodes and Sample Introduction.

The electrode arrangement described here has an inverted V-shape. The two electrodes were mounted on an aluminum platform about 4" apart by means of two 1/4" Swagelock to NPT connectors. The NPT ends were fixed into the platform and the Swagelock ends hold the high-voltage electrode through its 1/4" insulating plastic sheath and the ground electrode through its 1/8" to 1/4" Vespel/graphite ferrule. The platform was grounded separately for safety. The tips of both electrodes were about 4" above the table. A T-connector was used to introduce $N_2$ through the high-voltage electrode. The ground electrode was connected to another nitrogen source so that nitrogen flowed through both electrodes simultaneously. The tip of each copper electrode was filed to form a 30° angle and was rounded so the arc would be anchored to a fixed point of the electrode surface. With a nitrogen flow of about 100 mL/min through each electrode, an arc was formed between the two electrodes when the power supply was turned on. The arc could be sustained with an input voltage to the primary coil of the transformer of about 60 volts or higher. Since the 4 amp fuse in the variac that supplied the primary coil of the high voltage transformer lasted for over two months, the maximum current drawn by the arc was less than 4 amps, and the power consumed by the arc was estimated to vary between 100–300 watts, depending on the input voltage from the variac.

In order to ensure complete mixing of the analytes with the arc gases, a 1/4" OD, 3/16" ID, 6" length ceramic tubing (APR-0645, McDanel Refractory Company, Beaver Falls, Pa.) enclosed the ground electrode. Nitrogen, used to form the active gas in the arc, was introduced through the ceramic tubing that surrounded the outside of the copper electrode. Analyte was introduced through the inside of the copper tubing. The flow of nitrogen and analyte also served to cool and protect the inner copper electrode. The tip of the copper electrode was located inside the ceramic tube about 7 mm from the end of the ceramic tube. The high-voltage electrode was located about 3 mm over the top of the ceramic tube. This arrangement was chosen so that the arc was easily maintained and the ceramic tubing was heated to a dull red color at the tip. With the tip of the upper electrode located directly above the top edge of the ceramic tubing, hot excited gas flows out of the ceramic tubing without touching the upper electrode. This arrangement also places the upper electrode out of the field of view of the optical detection system. Although the upper electrode is not protected with this arrangement, corrosion of the electrode was not a problem unless corrosive compounds were introduced or were formed in the arc as discussed below. The observations reported herein was done with this arrangement unless otherwise specified.

Spectroscopic Instrumentation.

A computer-controlled scanning monochromator (Zhang, et al., 1992) was used to obtain all the spectral data reported herein. The instrument was equipped with a lead selenide detector and, with this detector, could access wavelengths from 2–5 µm. The monochromator was equipped with a 150 groove $mm^{-1}$ grating blazed for 4.0 µm. Calcium fluoride optics were used to form an image of the arc onto the entrance slit of the monochromator. This instrument was used to obtain all the spectral data reported herein.

$CO_2$ Emission from $N_2$ Discharge Arc Excitation.

Figure 38:
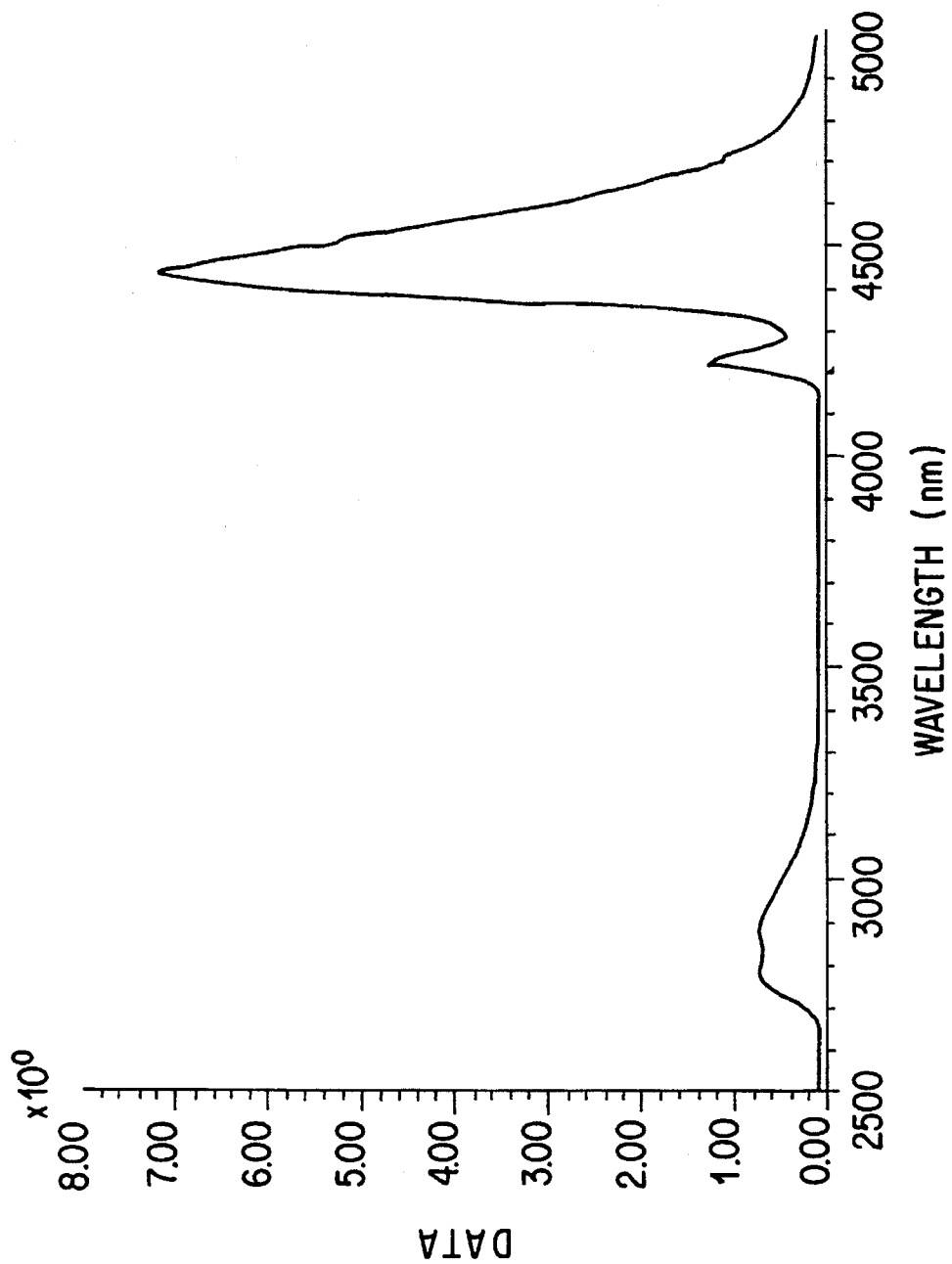
FIG. 38 shows the emission spectrum of $CO_2$ when introduced into the arc at a flow rate of about 6 ml/min.

Since almost all organic compounds can be converted easily into $CO_2$, excitation of $CO_2$ by active $N_2$ allows highly sensitive detection for organic compounds in general. FIG. 38 shows the emission spectrum observed from the arc when $CO_2$ when introduced at a flow rate of 6 mL $min^{-1}$. Compared with other forms of gas-phase infrared emission excitation used previously, nitrogen arc excitation shows only the strong emission from carbon dioxide. FIG. 38 shows that a very strong signal was observed at 4.4 µm and even the relatively weak combination band at 2.8 µm was observed. The spectrum obtained by nitrogen arc excitation was rather like that observed from combustion flames without any background but differed from that observed with electric furnace excitation (which produces a much narrower emission band at 4.4 µ m). The pink afterglow of the $N_2$ arc plume changed to a bluish color upon addition of $CO_2$ and the ceramic tubing changed to a slightly darker color, indicating a temperature decrease in the arc. Moreover, the arc shape became more diffuse when $CO_2$ was added to the nitrogen and the discharge became more uniform. The broadness of the $CO_2$ band shown in FIG. 38 indicates that higher vibrational levels of $v_3$ (which are closer together because of anharmonicity and therefore emit at longer wavelengths) are being populated. The significant splitting of the band due to self absorption indicates that most of the infrared emission is produced from the inner portion of the hot plume.

Figure 39:
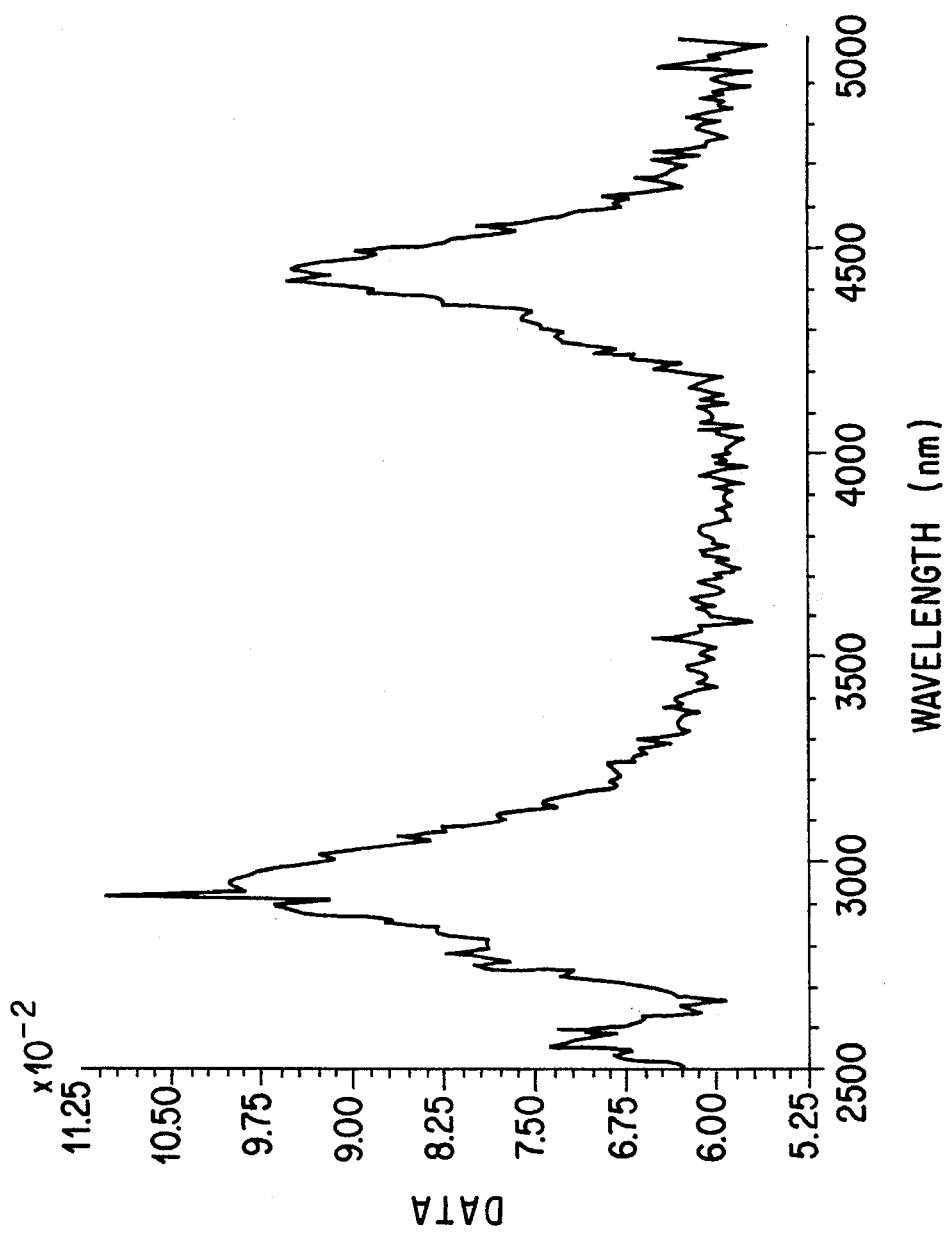
FIG. 39 shows a background spectrum of $N_2$ arc discharge.

FIG. 39 shows the background spectrum of the $N_2$ arc itself with an amplifier gain setting 100 times that used in FIG. 38 in order to observe the relatively weak background. This spectrum was obtained with an observation point about 3 mm above the top electrode. Because the arc plume is surrounded by ambient air, emission bands characteristic of water (3.0 µm) and carbon dioxide (4.4 µm) are observed because of entrainment of these molecules from the surrounding air into the arc plume. The presence of these bands confirms the effectiveness of the excitation from the afterglow of the arc; such background emission from ambient air is not generally seen with electrical furnace excitation, for example.

Discharges in Other Gases.

All homonuclear diatomic gases are infrared inactive and are therefore potentially useful in place of nitrogen as support gases for the AC arc. The energy level of $N_2$ is resonant with that of $CO_2$, in a like manner, the energy level of other diatomic gases may be resonant with other molecules. Energy levels of diatomic gases and various molecules may be found in Herzberg (1950). In addition, other diatomic and triatomic gases with very simple IR emission spectra have potential use as plasma support gases. Because of its availability, air was the second plasma gas studied in this example. Air contains about 21% oxygen and has a lower ionization potential compared with pure nitrogen. Because of the lower ionization potential, the arc was easily formed at a slightly lower input voltage than required when pure nitrogen was used. The air arc plume was a straw color and was larger and stronger in appearance compared with the $N_2$ arc. Significant $CO_2$ emission at 4.4 µm was observed when carbon dioxide was introduced into the air arc, and, as might be expected, the air arc background spectrum also showed significant IR emission at 4.4 µm from carbon dioxide (air contains 0.4% carbon dioxide). A pure oxygen arc was also investigated because of its potential for converting organic compounds into $CO_2$. The oxygen arc was observed to be more diffuse and exhibited a stronger visible plume.

Figure 40:
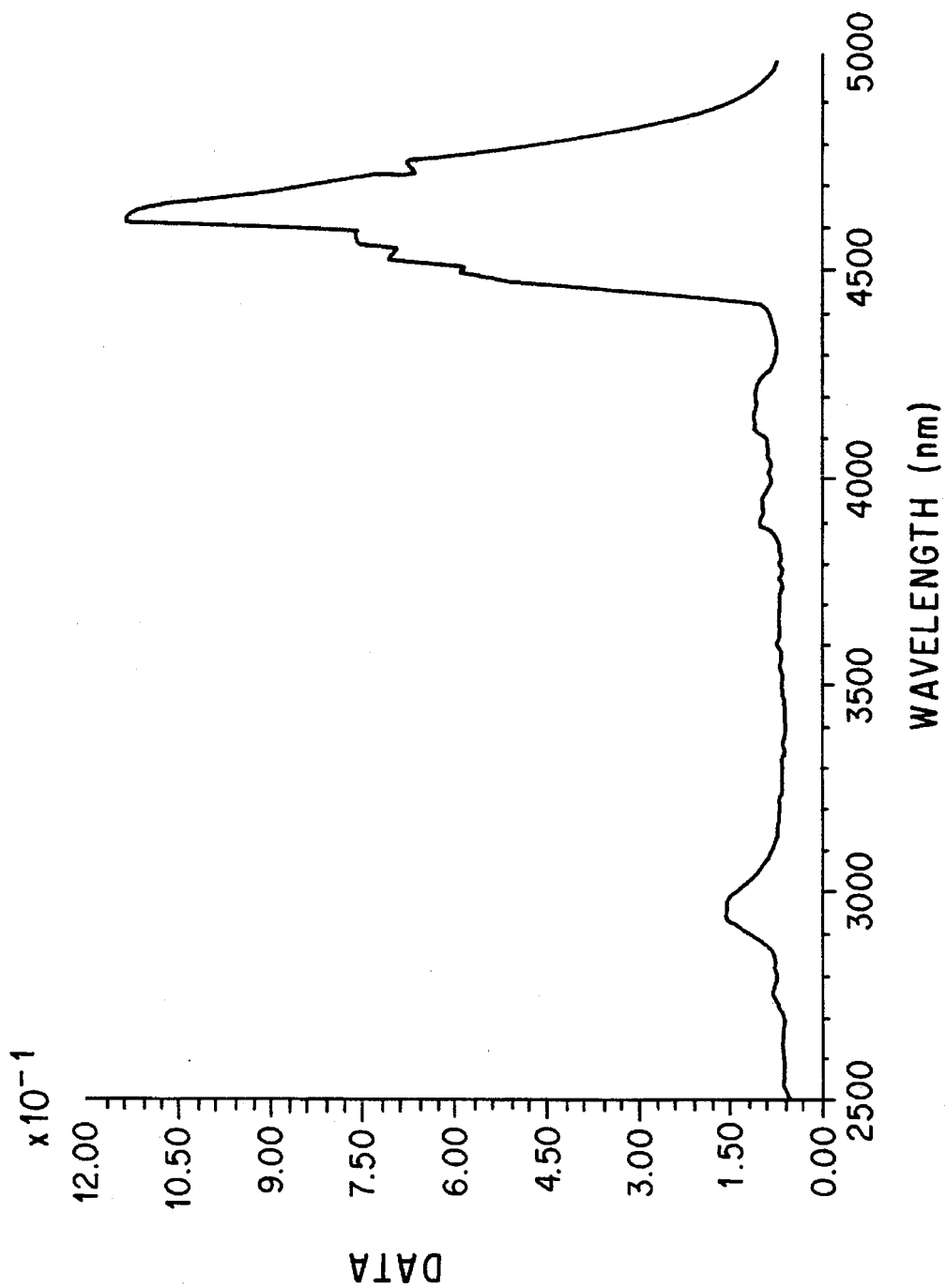
FIG. 40 shows a background spectrum of $N_2O$ emission.

An arc was also formed using the triatomic gas, nitrous oxide ($N_2O$), as the support gas. FIG. 40 shows the background spectrum obtained with the $N_2O$ arc. This spectrum shows the strong emission from $N_2O$ at 4.45–4.75 µm as well as weaker emissions at 2.9–3.1 µm and 3.9–4.25 µm. Compared with the background spectra observed with the other aforementioned gases, the background spectrum of the nitrous oxide arc does not show any background carbon dioxide emission from entrained ambient air. This may imply that carbon dioxide is not readily excited in the nitrous oxide arc, perhaps because of inefficient vibrational energy transfer from $N_2O$ to $CO_2$. The $N_2O$ arc was also the most corrosive to the copper electrodes, with visible corrosion observed after a few hours of operation. No IR emission from corrosion products was observed over the wavelength range from 2.5 µm to 5.0 µm.

Figure 41:
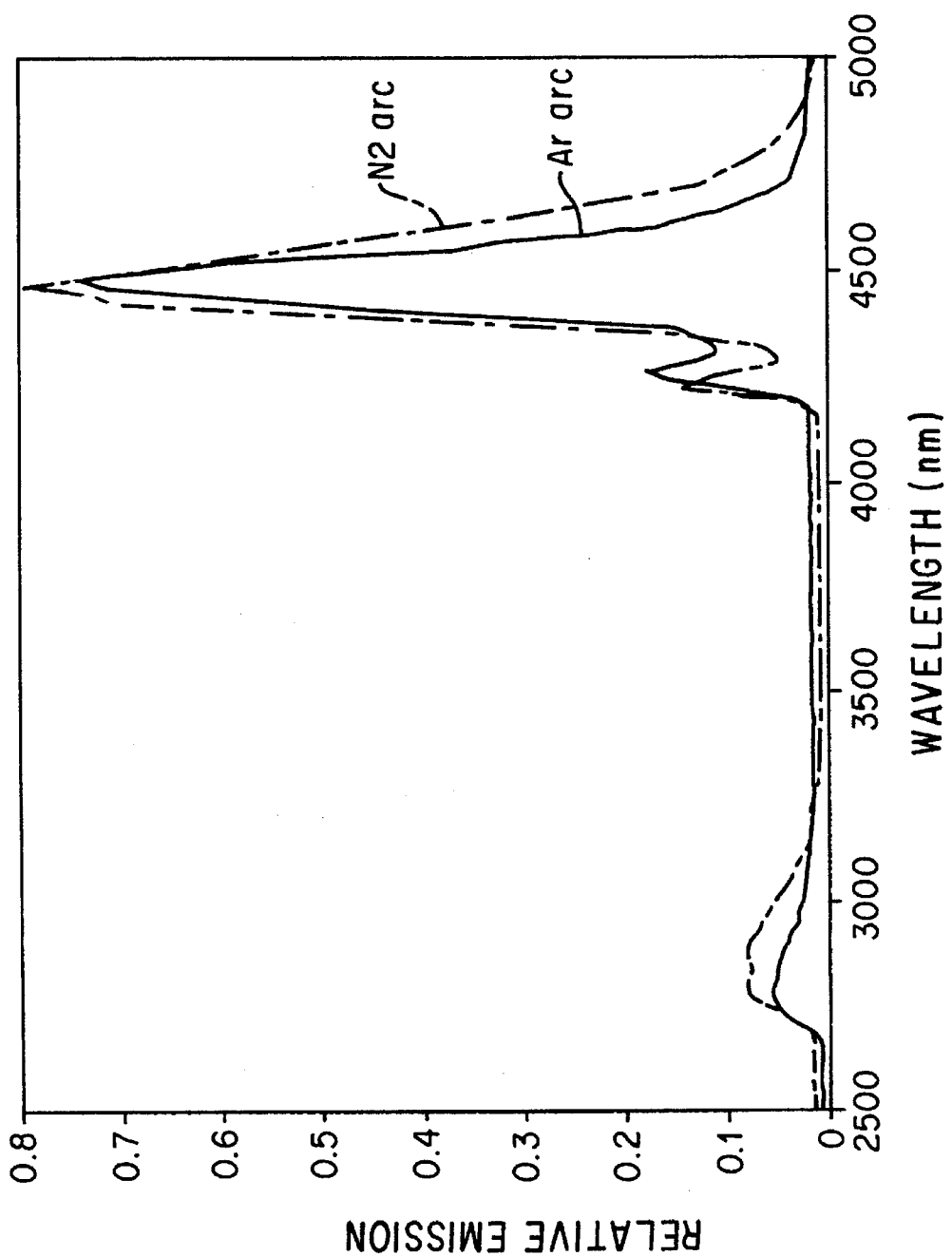
FIG. 41 shows a $CO_2$ emission spectrum in argon arc discharge compared with $N_2$ discharge arc.

In addition to the molecular gases mentioned, the inert atomic gas argon was also used as a support gas for the discharge. The discharge in argon showed a distinct streamer profile with the arc appearing as a threadlike form near the center of the ceramic tubing. With the limited input power available from the transformer, no visible plume was observed when argon was used as a support gas. Moreover, no trace of background $CO_2$ and $H_2O$ emission was observed with the argon arc, indicating poor efficiency in exciting vibrational levels of these molecules. FIG. 41 compares the emission spectrum from the argon arc with that from the nitrogen arc when carbon dioxide is introduced in both. The intensity scale of the emission spectrum from the argon arc has been doubled to facilitate comparison of the two spectra. Compared with the nitrogen arc, the $CO_2$ emission at 4.4 µm from the nitrogen arc is twice as intense and broader than that from the argon arc. Emission band broadening in gas-phase infrared emission arises from population of higher rotational levels as well as population of higher vibrational levels. The observations suggest that the $N_2$ arc discharge is considerably more efficient in the excitation of $CO_2$ than the corresponding argon arc discharge. Addition of $CO_2$ to the argon arc discharge caused the arc column to become more diffuse. Since argon is an atomic gas (with no vibrational levels), most of the $CO_2$ excitation in the argon arc must be due to thermal and direct electrical excitation of the $CO_2$ rather than indirectly by vibrational energy transfer from excited molecules.

Argon was found to be much less efficient than molecular gases in acting as a medium for converting electrical energy into vibrational energy. The most significant advantage of argon and helium in atomic emission spectroscopy is the simplicity of their atomic emission spectra which reduces potential interferences. As a medium for exciting gas-phase infrared emission, however, molecular gases clearly surpass the noble gases.

Ultrahigh purity nitrogen ($CO_2$ content less than 0.1 ppm, $H_2O$ content less than 0.2 ppm) was also used as a support gas to determine the origin of the water and carbon dioxide emissions observed in FIG. 39. Even with ultrahigh purity nitrogen, the water and carbon dioxide emissions shown in FIG. 39 were still present, indicating that the background $CO_2$ and $H_2O$ emissions observed with nitrogen, $O_2$, and ultrapure nitrogen did indeed arise from the surrounding ambient air rather than impurities in the support gases themselves.

Figure 48:
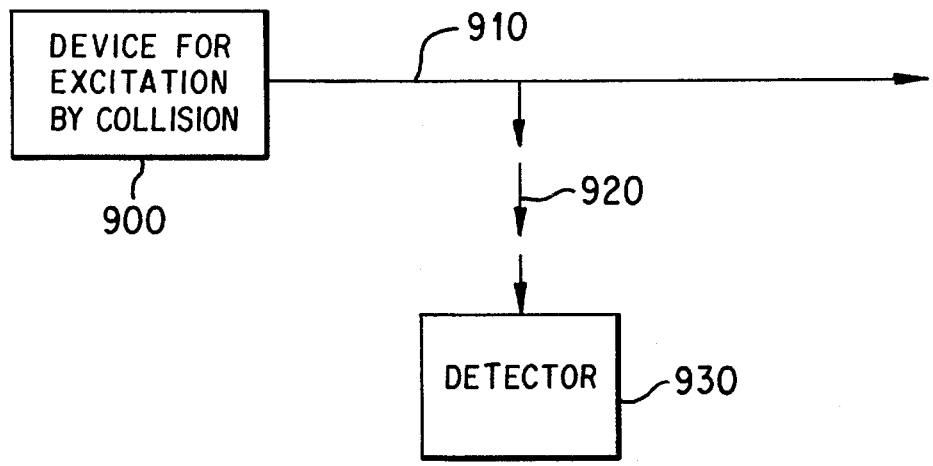
FIG. 48 shows a detection and measurement apparatus of this invention including a means for excitation by collisions with a vibrationally excited diatomic molecule.

In FIG. 48 there is shown an apparatus for detecting infrared radiation and making quantitative measurements, including device for excitation by collisions with a vibrationally excited diatomic molecule 900 wherein molecules to be excited are excited by collision with vibrationally excited diatomic molecules. Excited molecules exit device 900 as a stream of molecules 910 which emits infrared radiation 920. Infrared radiation 920 is detected by infrared radiation detector 930.

Introduction of Hexane into Arc Discharge.

The present inventors also studied gas-phase infrared emission produced when organic compounds were introduced directly into the arc discharge. Helium saturated with hexane was introduced into the arc through the ⅛" copper tubing ground electrode as was described previously for $CO_2$. Upon introduction of the hexane-saturated helium into the arc, a strong purple color was observed. When air or oxygen was used as the arc support gas, strong infrared emission from $CO_2$ (4.4 μm) and $H_2O$ (3.0 μm) was observed when hexane was introduced into the arc. As might be expected, the nitrogen arc gave a weaker, less reproducible infrared emission from $CO_2$ (4.4 μm) and $H_2O$ (3.0 μm) when hexane was introduced than either the air or oxygen arcs. Under the same conditions, the argon arc produced only very weak infrared emission from $CO_2$ (4.4 μm). No hexane CH emission (3.5 μm) or emission from other intermediate products was observed in any of the arcs over the spectral range from 2.5 to 5.0 μm. These studies show that when either air or oxygen is used as an arc support gas, the organic analyte is converted, at least in part, into $CO_2$, which can be detected as was done with flame excitation.

Figure 42A:
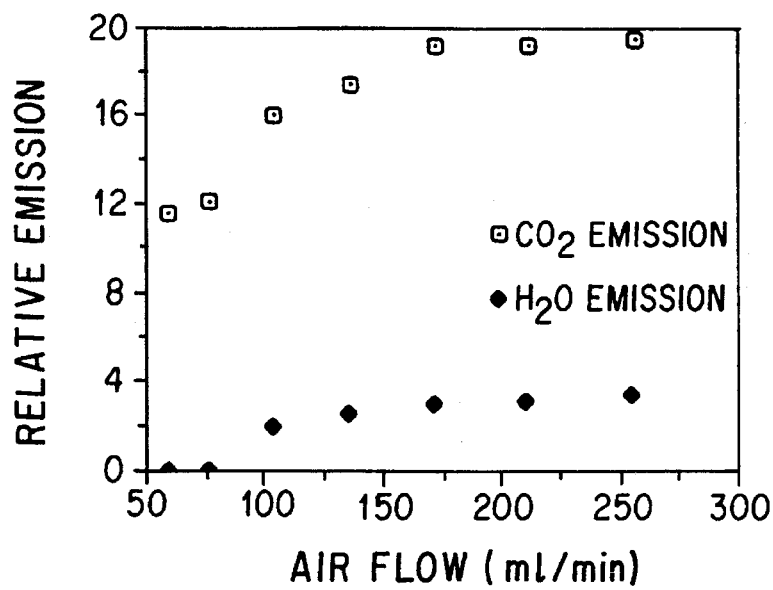
FIGS. 42A and 42B show the effect of air flow rate on emission from hexane in air arc discharge (31A) and the effect of air flow rate on background emission (31B).
Figure 42B:
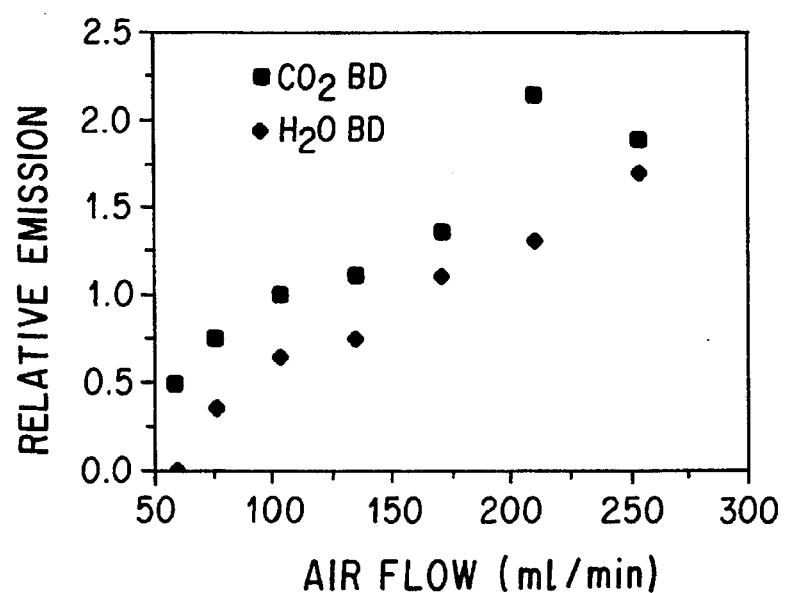

Infrared emission from $CO_2$ and $H_2O$ was studied in the air arc discharge as a function of applied input voltage and support gas (air) flow rate in an effort to determine the optimum excitation conditions for a common hydrocarbon like hexane. The emission intensity at 4.4 μm ($CO_2$) and 3.0 μm ($H_2O$ and the combination band of $CO_2$) was studied as a function of support gas (air) flow rate with and without the introduction of hexane. FIGS. 42A and 42B show plots of the results and Table 14 gives the numerical data used in FIGS. 42A and 42B. In FIGS. 42A and 42B and Table 14, BD stands for background and represents the intensities observed for $CO_2$ (4.4 μm) and $H_2O$ (3.0 μm) in the arc in the absence of hexane introduction. These background levels of $CO_2$ and $H_2O$ are presumed to arise from the support gas itself (which contains 0.4% $CO_2$) as well as entrainment of ambient air into the arc.

TABLE 14

| | Data for FIGS. 42A and 42B; Air Flow d | | | |
|---|---|---|---|---|
| Air Flow mL min$^{-1}$ | $CO_2$ BD | $H_2O$ BD | $CO_2$ Emission | $H_2O$ Emission |
| 1 | 60.00 | 0.50 | 0.00 | 11.60 | 0.12 |
| 2 | 77.00 | 0.75 | 0.35 | 12.20 | 0.12 |
| 3 | 104.00 | 1.00 | 0.65 | 16.00 | 2.00 |
| 4 | 135.00 | 1.10 | 0.75 | 17.45 | 2.50 |
| 5 | 171.00 | 1.35 | 1.10 | 19.25 | 3.00 |
| 6 | 210.00 | 2.15 | 1.30 | 19.25 | 3.20 |
| 7 | 255.00 | 1.90 | 1.70 | 19.40 | 3.50 |

From FIG. 42B, it can be seen that the background intensities at 4.4 μm ($CO_2$) and 3.0 μm ($H_2O$) both increase steadily as the support gas (air) flow rate increases with an apparent maximum in $CO_2$ intensity at about 210 mL min$^{-1}$. Since the air used as a support gas contains both $CO_2$ and water vapor, increasing the support gas flow rate should cause the infrared emission from both emitters to increase. However, it might be expected that the infrared emission intensity from $CO_2$ and $H_2O$ might begin to decrease with increasing flow rate at some point (i.e., go through a maximum) as a result of insufficient residence time in the arc for efficient excitation.

FIG. 42A shows the emission intensities at 4.4 μm ($CO_2$) and 3.0 μm ($H_2O$) as a function of support gas (air) flow rate when hexane is introduced into the air arc. It can be seen from FIG. 42A that the infrared emission at 4.4 μm ($CO_2$) increases initially at low flow rates and then reaches a plateau at flow rates greater than 170 mL min$^{-1}$. Water emission (3.0 μm) shows a similar trend leveling off at flow rates greater than 100 mL min$^{-1}$.

Measurement of emission intensities at 4.4 μm ($CO_2$) and 3.0 μm ($H_2O$) were conducted with the air arc as a function of input voltage to the primary coil of the discharge transformer. These measurements, shown in FIGS. 43A and 43B and Table 15, were all made with a support gas (air) flow rate of 210 mL min$^{-1}$. Once again measurements labelled BD represent the background intensities at 4.4 μm ($CO_2$) and 3.0 μm ($H_2O$) in the absence of hexane introduction into the arc.

The data in FIG. 43B show that both background intensities (4.4 μm and 3.0 μm) increase gradually with applied voltage to the primary coil of the transformer, leveling out after about 88 V. In the case of hexane introduction, the $CO_2$ intensity (4.4 μm) increases at low applied voltages but levels off after an applied voltage of 70 V is reached. By contrast, the $H_2O$ emission intensity (3.0 μm) seemed to show a very gradual increase over the entire range of applied voltages studied (up to 110 V). The introduction of hexane into the arc lowered the minimum voltage needed to sustain the air arc to 55 V (50% of the line voltage). Without the introduction of hexane, an air arc could not be maintained at this input voltage.

TABLE 15

Data for FIGS. 43A and 43B; Volt d

| Voltage | $H_2O$ BD | $CO_2$ BD | $H_2O$ | $CO_2$ |
|---|---|---|---|---|
| 1 | 55.000 | | | 1.200 | 11.200 |
| 2 | 66.000 | 2.000 | 2.000 | 2.200 | 15.950 |
| 3 | 77.000 | 2.400 | 2.600 | 2.650 | 16.550 |
| 4 | 88.000 | 2.800 | 2.800 | 3.000 | 16.500 |
| 5 | 99.000 | 2.700 | 2.700 | 3.350 | 16.500 |
| 6 | 110.000 | 2.900 | 2.900 | 3.850 | 16.650 |

Excitation of $CH_2Cl_2$ and $Cl_2/H_2$ Mixtures in an Air Arc Discharge.

Methylene chloride ($CH_2Cl_2$) was introduced into the arc to determine whether HCl would form in the arc and emit infrared emission at 3.8 µm as occurs with hydrogen-based combustion flames (Kubala, et al., 1989). When significant levels of methylene chloride ($CH_2Cl_2$) were introduced into the air arc, strong $CO_2$ emission (4.4 µm) was observed and a black deposit formed quickly around the ceramic tubing. This deposit caused the ceramic tubing to become conductive in the arc region, and the arc suddenly terminated at a certain spot in the ceramic tubing rather than at the internal copper electrode. It was also observed that the copper electrodes were corroded rapidly when methylene chloride was introduced into the arc.

To test the sensitivity of the arc for HCl detection, a mixture of $Cl_2$ and $H_2$ was introduced into the arc. Chlorine gas was generated chemically by acidifying a commercial bleaching solution. A 100 mL volume of commercial liquid bleach (5.5% NaOCl) was diluted to about 1900 mL in a 2 L HPLC solvent bottle and subsequently acidified with 48 mL of concentrated HCl. The bottle was wrapped with an aluminum film to avoid direct exposure of the solution to light (to prevent possible explosion of the mixture when $H_2$ was introduced). A glass dispersion tube was connected to the degassing port of the solvent bottle and $H_2$ was used to purge the $Cl_2$ out of the mixture. (Note: $Cl_2/H_2$ gas mixtures are explosive and care should be taken to avoid accidents with this experiment). The mixture was then dried by passing it through a trap containing concentrated $H_2SO_4$ to minimize corrosion of the copper tubing and fittings by moist $Cl_2$. Upon introducing the dry $Cl_2/H_2$ mixture into the arc, an HCl emission spectrum similar to that observed with a hydrogen combustion flame was observed (Kubala, et al., 1989).

Once again, the ceramic tubing gradually became conductive with the introduction of the $Cl_2/H_2$ mixture into the arc. Since both methylene chloride and $Cl_2$ caused the ceramic tube surrounding the copper electrode to become conductive, it may be supposed that $Cl_2$ was the cause in both cases. The most likely explanation for the increase in the conductivity of the ceramic tubing (and the black deposit observed when methylene chloride was added) is that a thin film of copper metal from the electrode is deposited on the ceramic in the presence of $Cl_2$. Copper reacts with $Cl_2$ to form volatile copper chlorides that decompose thermally on the surface of the hot ceramic tube, leaving a thin layer of metallic copper (which appears black). If this explanation is true, the problem can be solved by using a less reactive electrode.

Excitation of $CS_2$ in the Arc Discharge.

Introduction of organosulfur compounds into combustion flames has been shown to result in infrared emission at 7.5 µm due to $SO_2$ formation in the flame (Tilotta, et al., 1989). In an effort to determine whether any useful gas-phase, infrared-active sulfur compounds would be formed in the arc, the infrared emission spectrum of the arc was studied when carbon disulfide ($CS_2$) was introduced. (Note: Carbon disulfide has a flashpoint almost at room temperature and great care should be exercised in handling this compound, particularly in the presence of sparks).

Introduction of $CS_2$ into the arc also resulted in the formation of a conductive deposit on the ceramic tubing. This was avoided by arranging the ground electrode so that it protruded from the ceramic tube (instead of being recessed inside the tube). A very diffuse arc was observed when $CS_2$ was introduced and strong $CO_2$ emission. (4.4 µm) was observed.

To observe any possible $SO_2$ emission at 7.5 µm, a pyroelectric detector was used in place of the PbSe detector to observe the spectral region from 5 µm to about 9.0 µm. The long wavelength limit was imposed by the transmission cutoff of the $CaF_2$ collection optics. The short wavelength limit was imposed by a long pass filter (cut-on wavelength 5.0 µm) required to remove interference from the second-order spectrum produced by the diffraction grating. The 150 groove $mm^{-1}$ grating was replaced by one with 75 grooves $mm^{-1}$ that was blazed for 8.0 µm.

When $CS_2$ saturated helium was introduced into the air arc under conditions of low flow, no $SO_2$ emission was observed at 7.5 µm. With high flow rates of $CS_2$ saturated helium, the cool gas entering the arc tended to blow the arc discharge away, resulting in poor mixing of the analyte with the arc discharge gases. The failure to observe $SO_2$ emission at 7.5 µm may be due to a combination of factors: 1) only a small percentage of the $CS_2$ may be converted into $SO_2$ in the arc; 2) vibrational excitation of $SO_2$ may not be efficient in this arc; 3) the lifetime of the $SO_2$ vibrational excited state may be so long that collisional deactivation takes preference over radiative decay as the preferred mode of vibrational relaxation. Excitation through energy transfer with the air discharge plume is expected to be less efficient for $SO_2$ compared with $CO_2$ because of the larger energy difference between the vibrational levels of $N_2$ and $SO_2$.

Further Approaches on Effective Excitation: Sample Introduction with Corrosive Samples.

The problems of electrode corrosion and deposit formation on the ceramic tubing encountered with $CH_2Cl_2$ and $CS_2$ may be addressed by separating the arc body where the discharge current flows from the sample excitation region. If the sample flow is introduced only into the plume region, the discharge will not be disturbed by the sample introduction and the sample will not be directly exposed to electrically induced ionization. Corrosion of the electrodes will be avoided because the sample flow will not be in direct contact with the electrodes. Decomposition of the analyte in the plume region may be much less intense and vibrational excitation may become dominant upon suitable control of the pressure and active gas composition.

Figure 44:
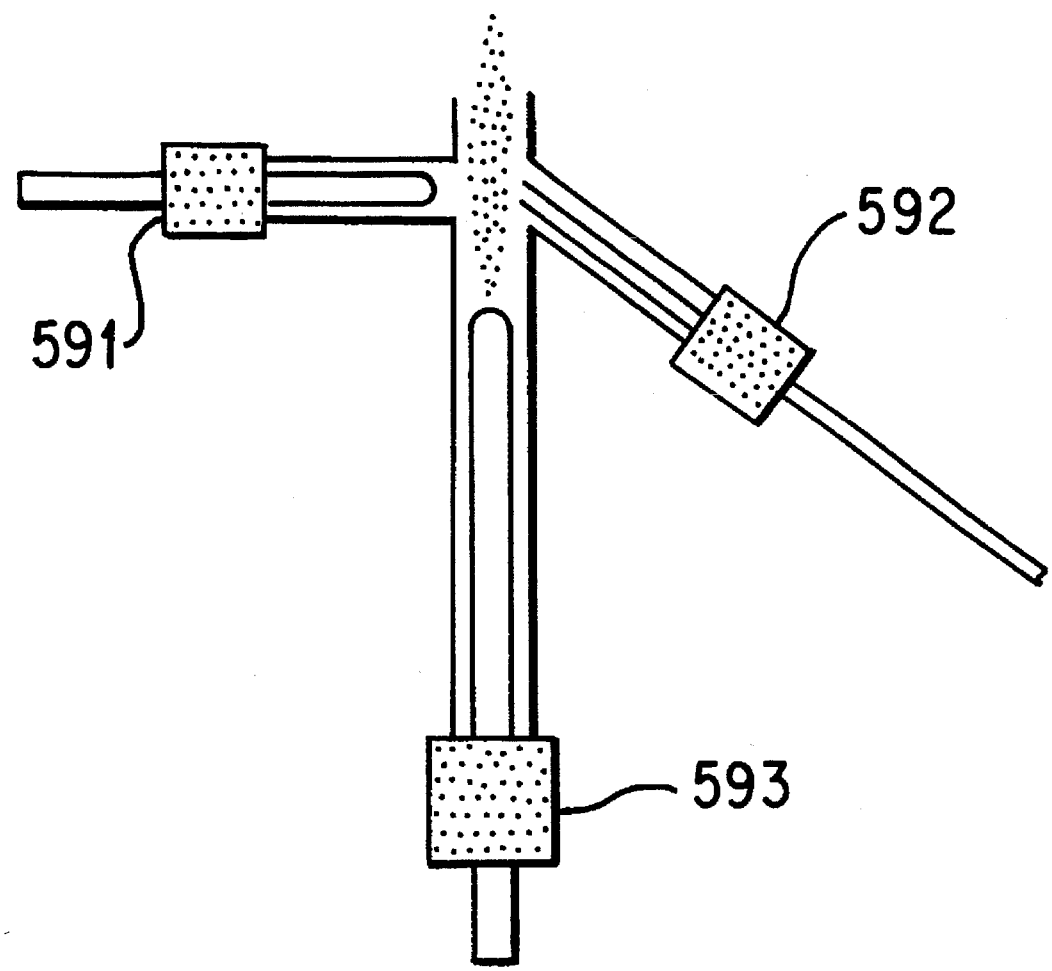
FIG. 44 shows a sketch of an arc discharge apparatus. Arm 593 holds the ground electrode connected to nitrogen flow. Arm 591 holds the active electrode and arm 592 is for sample introduction.

This new arrangement is shown in FIG. 44 and may be made from either silica or sapphire tubing. These materials may be preferred over the ceramic tubing for their ease of shaping into the desired arrangement, their high dielectric strength (which will provide better insulation), and their ability to withstand high temperature. To avoid interference from blackbody radiation, the gas-phase infrared emission will be observed above the top of the vertical tube. Arm 593 of the device will be used to hold the ground electrode, arm 591 holds the high voltage electrode, and arm 592 is for sample introduction. Nitrogen will flow from arm 593 as with the ceramic tubing. The length of the afterglow region is optimized by experiment.

Using Pressure Control to Increase Emission Intensity.

For molecules such as $SO_2$ that have a long radiative lifetime compared with the rate of collisional deactivation and no near-resonance IR inactive gas for its efficient excitation, pressure control may improve sensitivity. The importance of pressure control has been demonstrated in the laser excitation of gas-phase samples where sensitive detection is achieved at reduced pressure with species that showed no fluorescence at atmospheric pressure (Belz et al., 1987). Unlike other techniques of excitation, where decreasing the pressure may reduce the excitation efficiency (such as encountered with low pressure flames where the combustion efficiency is decreased) or increase the cost of the excitation source (such may be encountered with both the flame and the electrical furnace), electronic excitation is most efficient at reduced or relatively low pressure.

The formation of a uniform, stable discharge is more easily achieved at lower pressure than at atmospheric pressure. Indeed, a uniform, highly efficient discharge, without arc streamer formation is readily achieved at a low pressure because molecular diffusion is increased (i.e., the mean free path of gas molecules increases) and the plasma electron density is decreased. Both of these factors favor the formation of a uniform discharge by suppressing the tendency to form a condensed arc caused by attractive magnetic forces produced by movement of charged particles. Since the collision number decreases as the square of the pressure, collisional deactivation will be much less significant at reduced pressures. The combination of these factors will result in a much greater sensitivity for infrared emission measurements. The optimum pressure of the excitation source discharge will need to be determined experimentally. At very low pressures, collisions with the container walls will become significant and a large vacuum chamber will be required which would increase the cost of the system.

Stable, uniform gas discharges at reduced pressure have bene produced by the present inventors in the laboratory using the high voltage transformer described earlier. In these experiments, a simple rotary vacuum pump was used to evacuate a 30 cm long by 6 mm diameter length of glass tubing. The high voltage terminal of the transformer was connected to a brass electrode at one end of the tube and the ground electrode of the transformer was connected to a brass electrode at the other end of the tube. When the tube was evacuated to the limit of the rotary vacuum pump (about 1–5 torr) and the primary coil of the transformer was supplied with 110 V, a uniform plasma filled the entire length of the glass tube. The pink color of the discharge was indicative of excited nitrogen. A uniform discharge could also be maintained with the transformer (7500 V) even when various gases were leaked from a valve into the tube. Uniform, stable plasmas were obtained while leaking nitrogen, carbon dioxide, and hydrogen into the tube. When carbon dioxide was introduced into the reduced pressure plasma, the color of the plasma changed from pink (nitrogen) to an intense pale blue. This blue color has been observed in both flames and the atmospheric arc described previously when carbon dioxide was introduced. In all previous cases to date, this blue visible emission from carbon dioxide has been associated with $CO_2$ infrared emission at 4.4 μm. Because the glass tube does not transmit infrared radiation at 4.4 μm, the emission of $CO_2$ radiation at 4.4 μm has not been verified experimentally. Previous experience with other discharges, however, indicates that this discharge will produce intense infrared emission from $CO_2$. To observe the infrared emission from a low-pressure gas discharge of the type described here, a sapphire tube will need to be used.

Figure 45:
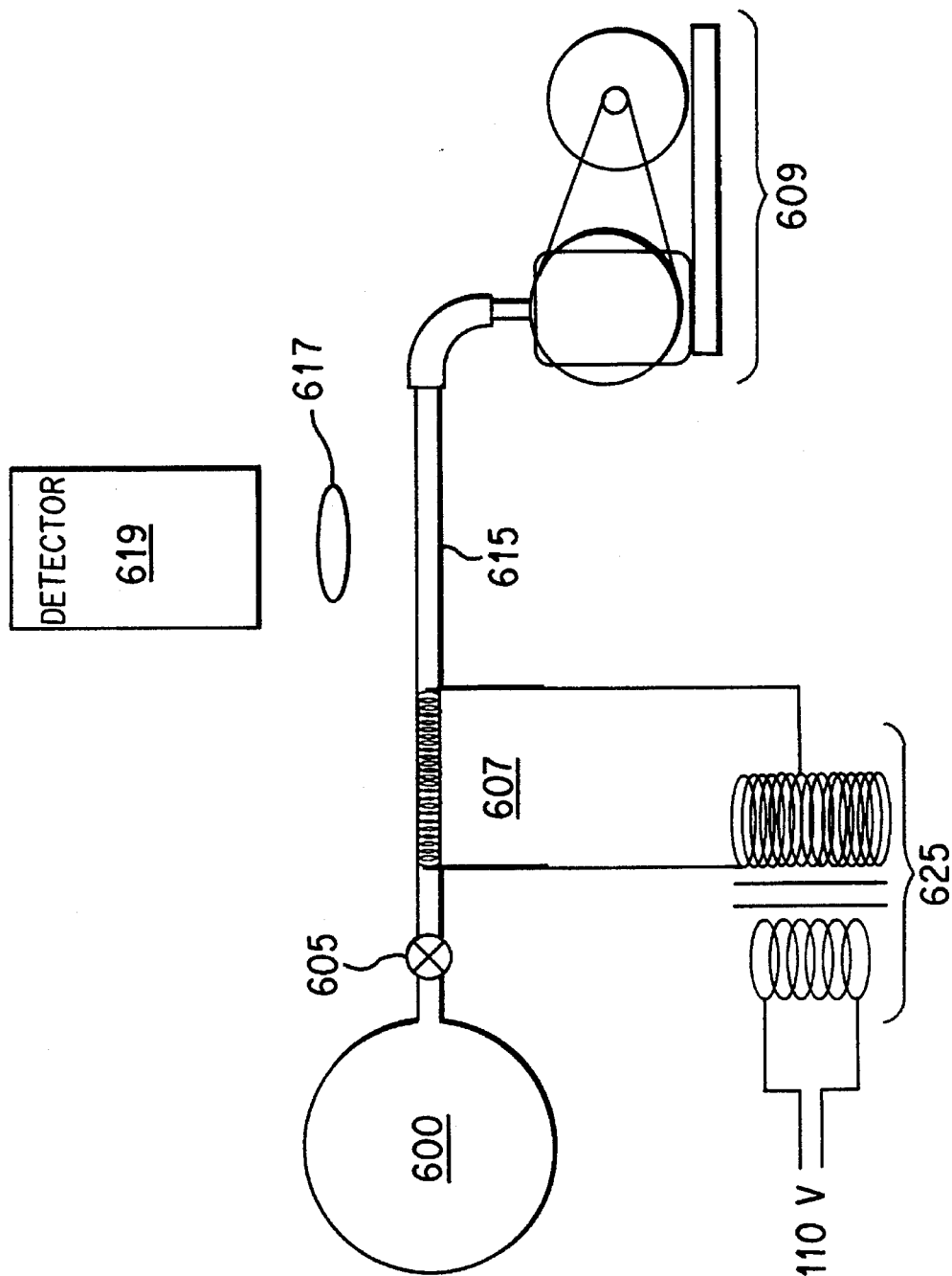
FIG. 45 shows the arrangement that would be used to observe gas-phase infrared emission from a reduced pressure discharge.

FIG. 45 shows the arrangement that would be used to observe gas-phase infrared emission from a reduced pressure discharge. A length of sapphire tubing (615) would be connected to a vacuum pump (609) at one end while the other end would be connected through a valve (605) to a vessel (600) that contains the gas to be analyzed. Electrodes (607) would be inserted into the walls of the sapphire tube at some distance apart. These electrodes would be connected to the secondary coil of a high voltage transformer (625) capable of supplying several thousand volts. The primary coil of the high transformer would be connected to the line voltage (110 V, 60 Hz). An infrared radiometer (619) with the associated collection optics (617) of the type described in Example 2 would be used to detect the infrared emission produced by the gas discharge. The observation point of the infrared radiometer would be located along the sapphire tube at a position that gives the maximum gas-phase infrared emission signal from the analyte gas.

This example has presented a study on gas-phase infrared emission based on electrical excitation. Conditions for effective excitation in atmospheric and reduced pressure discharges have been presented. IR emission from $CO_2$ and hydrocarbon detection based on $CO_2$ generation in an atmospheric pressure arc discharge have been presented.

REFERENCES

The following references are cited as of interest

U.S. Pat. No. 3,836,255.
U.S. Pat. No. 3,516,745.
U.S. Pat. No. 3,749,495.
Belz, H. H. et al., "Continuous-Wave $CO_2$ Laser-Excited Infrared Emission Spectroscopy," *Applied Spectroscopy*, 41:1009–1019, 1987.
Bernard, B. B., "A Summary of TOC Developments", O.I. Corporation College Station, Tex., 1985.
Boyd, R. W.; *Radiometry and the Detection of Optical Radiation*; John Wiley: New York, Chapter 10, 1983.
Busch, K. W.; Howell, N. G.; Morrison, G. H.; *Anal. Chem.* 46:1231, 1974.
Busch, K. W. et al., "Flame/Furnace Infrared Emission Spectroscopy: New Ways of Playing with FIRE," *Spectroscopy*, 4(8):22–36, 1989.
Busch, K. W. et al., "A High-Efficiency Light Collection System for Energy-Limited Infrared Emission Radiometers," *Applied Spectroscopy* 45:964–968, 1991.
Busch, M. A. & Busch, K. W., "Flame Infrared Emission (FIRE): A Versatile, New Element-Specific Detector for Gas Chromatography," *American Laboratory*, 23(11):18–24, 1991a.
Busch, M. A. & Busch, K. W., "A Signal-to-Noise Comparison of Flame/Furnace Infrared Emission (FIRE) Spectrometry with Room Temperature, Non-Dispersive Infrared Absorption Spectrophotometry," *Applied Spectroscopy*, 47:912–921, 1993.
Busch, M. A. & Busch, K. W., "Analytical Applications of Flame/Furnace Infrared Emission Spectrometry," *Spectrochimica Acta Reviews*, 14:303–336, 1991b.
Busch, M. A. & Busch, K. W., "Signal-to-Noise Considerations in Flame/Furnace Infrared Emission Spectroscopy," *Applied Spectroscopy*, 45:546–554, 1991c.
Christensen, C. P., "Pulsed Transverse Electrodeless Discharge Excitation of a $CO_2$ Laser," *App. Phys. Lett*, 34(3):211–213, 1979.
Curcio, J. A.; Buttrey, D. V. E.; *Appl. Opt.*, 5:231, 1966.
Garrett, R. L., *J. Pet. Tech.*, p. 860, June, 1978.
Gaydon, A. G.; *The Spectroscopy of Flames*; Chapman and Hall: London, pp. 221–243, 1974.
Gaydon, A. G.; Wolfhard, H. G.; *Flames, Their Structure, Radiation and Temperature*, 4th ed.; Chapman and Hall: London, pp. 238–259, 1979.

*Handbook of Chemistry and Physics*, CRC Press, Boca Raton, Fla., 72nd ed., Section 3, pp. 191, 519 and 520, 1991.

*Handbook of Chemistry and Physics*, CRC Press, Boca Raton, Fla., 72nd ed., Section 3, pp. 273, 321 and 363, 1991.

Herzberg, Gerhard, "Spectra of Diatomic Molecules," *Molecular Spectra and Molecular Structure*, Van Nostrand, Vol. 1, 1950.

Hudson, M. K. & Busch, K. W., "Infrared Emission from a Flame as the Basis for Chromatographic Detection of Organic Compounds," *Analytical Chemistry*, 59:2603–2609, 1987.

Hudson, M. K. & Busch, K. W., "Flame Infrared Emission Detector for Gas Chromatography," *Analytical Chemistry*, 60:2110–2115, 1988.

Jurgensen, H. and Winefordner, J. D., "Use of Active Nitrogen in Analytical Chemiluminescence Spectroscopy," *Talanta*, 31:777–782, 1984.

Karger, B. L. et al., *An Introduction to Separation Science*, Wiley, New York, pp. 232–236, 1973.

Kishman, J. et al., "The Dielectric Discharge as an Efficient Generator of Active Nitrogen for Chemiluminescence and Analysis," *Applied Spectroscopy*, 37:545–552, 1983.

Kubala, S. W. et al., "Determination of Total Inorganic Carbon in Aqueous Samples with a Flame Infrared Emission Detector," *Analytical Chemistry*, 61:1841–1846, 1989a.

Kubala, S. W. et al., "Determination of Chloride and Available Chlorine in Aqueous Samples by Flame Infrared Emission," *Analytical Chemistry*, 61:2785–2791, 1989b.

Kubala, S. W. et al., "Design and Performance of a Direct-Reading, Multichannel Spectrometer for the Determination of Chlorinated Purgeable Organic Compounds by Flame Infrared Emission Spectroscopy," *Talanta*, 38:589–602, 1991.

Lam, K. Y. et al., "Design and Performance of a New Continuous Flow Sample-Introduction System for Flame Infrared—Emission Spectrometry: Applications in Process Analysis, Flow Injection Analysis, and Ion-Exchange High-Performance Liquid Chromatography," *Talanta*, 40:867–878, 1993.

Lam, C. K. Y. et al., "An Investigation of the Signal Obtained from a Flame Infrared Emission (FIRE) Detector," *Applied Spectroscopy*, 44:318–325, 1990.

Manahan, S. E., *Environmental Chemistry*, 3rd. Ed., Willard Grant Press: Boston, Mass. 1979.

McNair, H. M., Bonelli, E. J., *Basic Gas Chromatography*, 5th ed., Varian Instrument Division, Palo Alto, Calif., pp. 81–5, 1969.

Nakamoto, K., *Infrared Spectra of Inorganic and Coordination Compounds*; John Wiley: New York, p. 77, 1963.

Plyler, E. K., J. Res. Nat. Bur. Stand., 40:113, 1948.

Putley, E. H. In: *Optical and Infrared Detectors*, Keyes, R. J., Ed.; Springer-Verlag: Berlin, Chapter 3, 1980.

Ravishankar, S. et al., "An Element-Specific, Dual-Channel Flame Infrared Emission, Gas Chromatography Detector for Chlorinated and Fluorinated Hydrocarbons," *Applied Spectroscopy*, 44:1247–1258, 1990a.

Ravishankar, S. et al., "Dual-Channel Flame Infrared Emission Detector for Gas Chromatography," *Analytical Chemistry*, 62:1604–1610, 1990b.

Ravishankar, S. et al., "Spatial Emission Characteristics of a Capillary-Burner Excitation Source for a Flame Infrared Emission (FIRE) Radiometer," *Applied Spectroscopy*, 45:1684–1694, 1991.

Skoog, D. A., "Principles of Instrumental Analysis," 3rd Ed., p. 297, Saunders College Publishing, 1985.

Small, R. A. et al., *International Laboratory*, May, 1986.

*Standard Methods for the Examination of Water and Wastewater*, Greenburg, A. E., Trussel, R. R., Clesceri, L. S., Franson, M. A. H., Eds., American Public Health Association, 16th Ed., Washington, D.C. pp. 286–294, 1985.

Tilotta, D. C. et al., "A Miniature Electrical Furnace as an Excitation Source for Low-Temperature, Gas-Phase, Infrared Emission Spectroscopy," *Applied Spectroscopy*, 45:178–185, 1991.

Tilotta, D. C. et al., "Evaluation of Thermospray and Cross-Flow Pneumatic Nebulization as a Means of Interfacing a Flame Infrared Emission (FIRE) Radiometer to a High-Performance Liquid Chromatograph," *Applied Spectroscopy*, 47:192–200, 1993.

Tilotta, D. C. et al., "Fourier-Transform Flame Infrared Emission Spectroscopy," *Applied Spectroscopy*, 43:704–709, 1989.

Whitlock, W. H. et al., *Microcontamination*, May, 1988.

Zhang, Y. et al., "Pre-excitation, Catalytic Oxidation of Analytes over Hopcalite in Flame/Furnace Infrared Emission (FIRE) Spectrometry," Applied Spectroscopy, 46:631–639, 1992a.

Zhang, Y. et al., "Evaluation of an Improved Burner Design for a Flame Infrared Emission (FIRE) Gas Chromatography Detector," *Applied Spectroscopy*, 46:930–939, 1992b.

Zhang, Y. et al., "Terminal and Intermediate Combustion Products Observed from 2.0–5.0 µm in Flame/Furnace Infrared Emission Spectrometry," *Applied Spectroscopy*, 46:1673–1684, 1992c.

Although the invention has been described by reference to some preferred embodiments, it is not intended that the novel infrared detection means and method be limited thereby but various modifications are intended to be included as falling within the spirit and broad scope of the foregoing disclosure, the attached drawings and the following claims.

What is claimed is:

1. An apparatus for detecting and making quantitative measurements of at least one selected component in a sample, in which at least one selected component of the sample, or at least one selected substance produced from the at least one selected component in the sample and characteristic of the at least one selected component, is introduced into an exciting means, and when the at least one selected component is present in the sample, gas-phase infrared-active molecules emit infrared radiation at at least one characteristic wavelength in proportion to the quantity of the at least one selected component in the sample, comprising:

means for exciting the gas-phase, infrared-active molecules to emit radiation over a given path, wherein when the at least one selected component is present in the sample, the gas-phase infrared-active molecules emit radiation at the at least one characteristic wavelength with an intensity proportional to the quantity of the at least one selected component in the sample and wherein the means for exciting the gas-phase, infrared-active molecules is by furnace excitation, excitation by electron impact in a gas discharge or excitation by collisions with a vibrationally excited diatomic molecule;

infrared discriminating and detector means located on said given path for detecting infrared radiation at the at least one characteristic wavelength and for generating an output signal representative thereof, and thereby determining the quantity of the at least one selected component in the sample.

2. The apparatus according to claim 1, wherein said infrared discriminating and detector means includes wavelength discriminating means located on said path, between the exciting means and the infrared detector means, for allowing the at least one characteristic wavelength to pass from the exciting means to the detector means while inhibiting the passage of other wavelengths.

3. The apparatus according to claim 1, wherein said infrared discriminating and detector means includes means for separating the wavelengths of the emitted radiation into an infrared spectrum.

4. The apparatus according to claim 1, wherein said infrared discriminating and detector means includes a monochromator.

5. The apparatus according to claim 1, further including a computer means, responsive to an output signal from the infrared detector means, for performing signal processing thereon to provide an output indicative of the quantity of the at least one selected component present in the sample.

6. The apparatus according to claim 1, wherein said infrared discriminating and detector means includes an interferometer.

7. The apparatus according to claim 6, further comprising a computer means, coupled to the interferometer, for performing a Fourier transform analysis on an output signal from the interferometer to thereby obtain a spectral analysis characteristic of the sample.

8. The apparatus according to claim 1, further including vaporizing means for vaporizing a liquid sample and for conducting the resultant vapors into said exciting means.

9. The apparatus according to claim 1, wherein the means for exciting the gas-phase, infrared-active molecules is by furnace excitation.

10. The apparatus according to claim 1, wherein said infrared detector means includes a thermal infrared detector.

11. The apparatus according to claim 1, wherein said infrared detector means includes a quantum detector.

12. The apparatus according to claim 1, wherein the at least one selected component or the at least one selected substance contains carbonates or calcinates, further including means for acidifying the at least one selected component or the at least one selected substance to generate $CO_2$ therefrom, wherein the $CO_2$ so generated is introduced into the exciting means.

13. The apparatus according to claim 1, wherein the at least one selected component or the at least one selected substance contains carbon-containing compounds, further including means for oxidizing the at least one selected component or the at least one selected substance to generate $CO_2$ therefrom, wherein the $CO_2$ so generated is introduced into the exciting means.

14. The apparatus according to claim 1, wherein the at least one selected component or the at least one selected substance contains hypochlorous acid or hypochlorite ions, further including means for acidifying the at least one selected component or the at least one selected substance with HCl to generate $Cl_2$ therefrom, wherein the $Cl_2$ so generated is introduced into the exciting means.

15. The apparatus according to claim 1, wherein the at least one selected component or the at least one selected substance contains chloride ions, further including means for oxidizing and acidifying the at least one selected component or the at least one selected substance to generate chlorine $Cl_2$ therefrom, wherein the $Cl_2$ so generated is introduced into the exciting means.

16. The apparatus according to claim 1, wherein the at least one selected component of the sample or the at least one selected substance includes carbon-containing compounds, and said exciting means includes a means for oxidizing the at least one selected component of the sample or the at least one selected substance to generate $CO_2$ therefrom, wherein the $CO_2$ so generated is introduced into the exciting means.

17. The apparatus according to claim 1, wherein the at least one selected component or the at least one selected substance includes chlorine-containing organic compounds, and said exciting means includes a means for combusting the at least one selected component or the at least one selected substance to thereby generate HCl therefrom, wherein the HCl so generated is introduced into the exciting means.

18. The apparatus according to claim 1, wherein the at least one selected component or the at least one selected substance includes fluorine-containing organic compounds, and said exciting means includes a means for combusting the at least one selected component or the at least one selected substance to thereby generate HF therefrom, wherein the HF so generated is introduced into the exciting means.

19. A method for detecting and making quantitative measurements of at least one selected component in a sample, in which at least one selected component of the sample, or at least one selected substance produced from the at least one selected component in the sample and characteristic of the at least one selected component, is introduced into an exciting means, and when the at least one selected component is present in the sample, gas-phase infrared-active molecules emit infrared radiation at at least one characteristic wavelength in proportion to the quantity of the at least one selected component in the sample, comprising the steps of:

exciting the gas-phase, infrared-active molecules to emit radiation, wherein when the at least one selected component is present in the sample, the gas-phase infrared-active molecule emit radiation at the at least one characteristic wavelength with an intensity proportional to the quantity of the at least one selected component in the sample; and selectively detecting infrared radiation emitted at the at least one characteristic wavelength and generating an output signal representative thereof, and thereby determining the quantity of the at least one selected component in the sample and wherein said exciting step is by thermal excitation using an electric furnace, excitation by electron impact in a gas discharge or excitation by collisions with a vibrationally excited diatomic molecule.

20. The method according to claim 19, including the step of discriminating the at least one characteristic wavelength by allowing only the at least one characteristic wavelength to be detected in the detecting step while inhibiting the detection of other wavelengths.

21. The method according to claim 20, wherein said discriminating step includes separating the wavelengths of the emitted radiation into an infrared spectrum.

22. The method according to claim 20, wherein said discriminating step includes utilizing a monochromator.

23. The method according to claim 20, wherein said discriminating step includes utilizing an interferometer.

24. The method according to claim 23, wherein said discriminating step includes utilizing a computer coupled to the interferometer for performing a Fourier transform analysis on an output signal from the interferometer to thereby obtain a spectral analysis characteristic of the sample.

25. The method according to claim 19, further including utilizing a computer for performing signal processing on the output signal produced by said detecting step to provide an output indicative of the quantity of the at least one selected component present in the sample.

26. The method according to claim 19, including vaporizing a liquid sample and utilizing the resultant vapors in said exciting step.

27. The method according to claim 19, wherein said exciting step is by thermal excitation using an electric furnace.

28. The method according to claim 19, wherein the at least one selected component or the at least one selected substance contains carbonates or calcinates, further including acidifying the at least one selected component or the at least one selected substance to generate $CO_2$ therefrom, and utilizing the $CO_2$ so generated in the exciting step.

29. A method according to claim 19, wherein the at least one selected component or the at least one selected substance contains carbon-containing compounds, further including oxidizing the at least one selected component or the at least one selected substance to generate $CO_2$ therefrom, and utilizing the $CO_2$ so generated in the exciting step.

30. The method according to claim 19, wherein the at least one selected component or the at least one selected substance contains hypochlorous acid or hypochlorite ions, further including acidifying the at least one selected component or the at least one selected substance with HCl to generate $Cl_2$ therefrom, and utilizing the $Cl_2$ so generated in the exciting step.

31. The method according to claim 19, wherein the at least one selected component or the at least one selected substance contains chloride ions, further including oxidizing and acidifying the at least one selected component or the at least one selected substance to generate chlorine $Cl_2$ therefrom, and utilizing the $Cl_2$ so generated in the exciting step.

32. The method according to claim 19, wherein the at least one selected component of the sample or the at least one selected substance includes carbon-containing compounds and oxidizing the at least one selected component of the sample or the at least one selected substance to generate $CO_2$ therefrom, and utilizing the $CO_2$ so generated in the exciting step.

33. The method according to claim 19, wherein the at least one selected component or the at least one selected substance includes chlorine-containing organic compounds and combusting the at least one selected component or the at least one selected substance to generate HCl therefrom, and utilizing the HCl so generated in the exciting step.

34. The method according to claim 19, wherein the at least one selected component or the at least one selected substance includes fluorine-containing organic compounds and combusting the at least one selected component or the at least one selected substance to generate HF therefrom, and utilizing the HF so generated in the exciting step.

* * * * *

UNITED STATES PATENT AND TRADEMARK OFFICE
CERTIFICATE OF CORRECTION

PATENT NO.   :   5,473,162

DATED        :   December 5, 1995

INVENTOR(S)  :   Busch *et al.*

It is certified that error appears in the above-identified patent and that said Letters Patent is hereby corrected as shown below:

Title page Item No. [75], delete "Zhand" and insert --Zhang-- therefor.

Signed and Sealed this

Twenty-sixth Day of March, 1996

Attest:

BRUCE LEHMAN

Attesting Officer          Commissioner of Patents and Trademarks